United States Patent
Avner et al.

(10) Patent No.: US 12,402,609 B2
(45) Date of Patent: Sep. 2, 2025

(54) METHODS FOR PRODUCING HYPO-ALLERGENIC CATS USING GENE EDITING TECHNOLOGY

(71) Applicant: FELIX PETS, LLC, Highlands Ranch, CO (US)

(72) Inventors: David B. Avner, Highlands Ranch, CO (US); Sven Bocklandt, Los Angeles, CA (US); James Kehler, Silver Spring, MD (US)

(73) Assignee: FELIX PETS, LLC, Highlands Ranch, CO (US)

( * ) Notice: Subject to any disclaimer, the term of this patent is extended or adjusted under 35 U.S.C. 154(b) by 1234 days.

(21) Appl. No.: 16/069,998

(22) PCT Filed: Jan. 13, 2017

(86) PCT No.: PCT/US2017/013540
§ 371 (c)(1),
(2) Date: Jul. 13, 2018

(87) PCT Pub. No.: WO2017/124022
PCT Pub. Date: Jul. 20, 2017

(65) Prior Publication Data
US 2020/0008405 A1  Jan. 9, 2020

Related U.S. Application Data

(60) Provisional application No. 62/278,293, filed on Jan. 13, 2016.

(51) Int. Cl.
*A01K 67/0275* (2024.01)
*C12N 5/074* (2010.01)
*C12N 15/87* (2006.01)

(52) U.S. Cl.
CPC ........ *A01K 67/0275* (2013.01); *C12N 5/0696* (2013.01); *C12N 15/87* (2013.01); *A01K 2217/00* (2013.01); *A01K 2227/10* (2013.01); *A01K 2267/02* (2013.01)

(58) Field of Classification Search
CPC ............ A01K 67/0275; A01K 2217/00; A01K 2227/10; A01K 2267/02; C12N 5/0696; C12N 15/87

See application file for complete search history.

(56) References Cited

U.S. PATENT DOCUMENTS

| 2009/0002946 | A1  | 1/2009  | Choo et al. | |
|---|---|---|---|---|
| 2009/0029816 | A1  | 1/2009  | Gramby et al. | |
| 2009/0298168 | A1* | 12/2009 | Avner | C12N 9/16 |
| | | | | 435/351 |
| 2010/0009305 | A1  | 1/2010  | Braga et al. | |
| 2011/0002315 | A1  | 1/2011  | Bedell et al. | |
| 2011/0023156 | A1† | 1/2011  | Bedell | |
| 2012/0142110 | A1* | 6/2012  | Avner | A01K 67/0276 |
| | | | | 435/463 |
| 2012/0192298 | A1† | 7/2012  | Weinstein | |
| 2013/0023696 | A1  | 1/2013  | Hagiya | |
| 2014/0134739 | A1† | 5/2014  | Avner | |
| 2015/0044192 | A1* | 2/2015  | Liu | C12Q 1/6869 |
| | | | | 424/94.6 |

FOREIGN PATENT DOCUMENTS

WO  2010053472 A1 †  5/2010

OTHER PUBLICATIONS

Verma et al. "Inducing pluripotency in somatic cells from the snow leopard (Panthera uncia), an endangered felid."Theriogenology . Jan. 1, 2012;77(1):220-8, 228.e1-2. (Year: 2012).*
Li et al. "Excision of Expanded GAA Repeats Alleviates the Molecular Phenotype of Friedreich's Ataxia."Mol Ther. Jun. 2015; 23(6):1055-1065. (Year: 2015).*
International Search Report and Written Opinion from parent application PCT/US2017/013540, dated Aug. 4, 2017, 13 pages.
Chen, Y. et al., Engineering Human Stem Cell Lines with Inducible Gene Knockout using CRISPR/Cas9, 13 pages, Aug. 6, 2015, US.†
Gómez, M.C., et al., Birth of African Wildcat Cloned Kittens Born from Domestic Cats, 12 pages, Feb. 2004, US.†
Gomez, M.C.et al., Generation of Domestic Transgenic Cloned Kittens Using Lentivirus Vectors, 9 pages, Mar. 2009, US.†
Cui, C. et al., Gene targeting by TALEN-induced homologous recombination in goats directs production of beta-lactoglobulin-free, high-human lactoferrin milk, 11 pages, May 21, 2015.†
Ezashi, T. et al., Pluripotent Stem Cells from Domesticated Mammals, 31 pages, Nov. 3, 2015, US.†
Gómez, M.C. et al., Derivation of cat embryonic stem-like cells from in vitro-produced blastocysts on homologous and heterologous feeder cells, 18 pages, 2010, US.†
Ni, W. et al., Efficient Gene Knockout in Goats Using CRISPR/Cas9 System, 7 pages, Sep. 4, 2014, US.†
Pope, C.E. et al., In vitro production and transfer of cat embryos in the 21st century, 14 pages, Apr. 18, 2006, US.†
Verma, R. et al., Inducing pluripotency in somatic cells from the snow leopard (Panthera uncia) an endangered felid, 11 pages, 2012, US.†

(Continued)

*Primary Examiner* — Titilayo Moloye

(74) *Attorney, Agent, or Firm* — Quarles & Brady, LLP

(57) ABSTRACT

A genetically modified cat produced through gene editing with a phenotype characterized by the substantial absence of the major cat allergen, Fel d I. The phenotype is conferred in the genetically modified cat by targeting either the gene sequence of the Fel d I locus or sequences flanking the coding sequence of the two contiguous Fel d I genes with specialized gene editing constructs. The genotype and phenotype of the genetically modified cat is transmissible to its offspring.

17 Claims, 30 Drawing Sheets

Specification includes a Sequence Listing.

(56) References Cited

OTHER PUBLICATIONS

Verma, R. et al., Nanog is an Essential Factor for Induction of Pluripotency in Somatic Cells from Endangered Felids, 5 pages, Feb. 2013, US.†

Yin et al., X J, Cats cloned from fetal and adult somatic cells by nuclear transfer, 5 pages, 2005, US.†

\* cited by examiner
† cited by third party

Female Kitten, Chain 1

CRISPR/Cas9 Target sequence in WT: 5' GT GGC CGC AAC AGT AGG GCA GGG T 3'
1 nucleotide insertion in chain 1: 5' GT GGC CGC AAC AGT AGG GCA GGG G 3'

FIG. 26

Male Kitten, Chain 2

CRISPR/Cas9 Target sequence in WT: 5' GAG GGG GGC ACT GCT TGT GCT GG 3'
1 nucleotide insertion in chain 2: 5' GAG GGG GGC ACT GCT TGG TGC TGG 3'

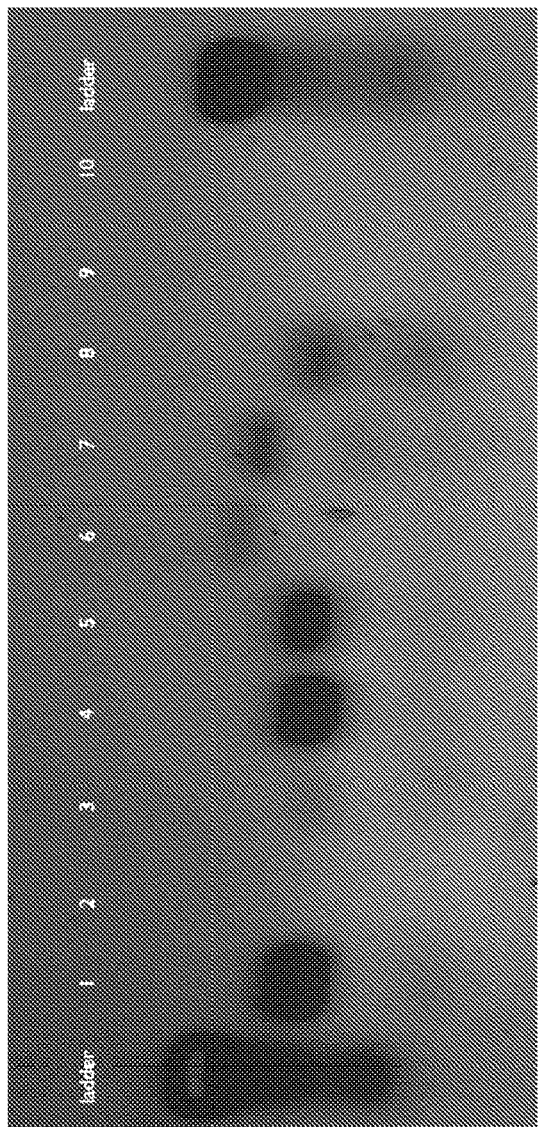

NNNNNNNNNGCANNNCNNNNCTGGTGGCCAAGCAGGCGTTGAGCAGCCTGGGCCAGCCCCAAAGCTTGAGGGGTAGGCTGAATCTTCCCACATGATCC
CCTCTACTTCCCACATGATCCCAGCCATGGCGTCTTTTCTCCAGATTCCCAGGAAGGCCATGGTTGGAGAACATGAGCAACCCCCTCCTGCACTGCCCTGAG
CAGACCCCCGGGGACATGGCCAGGTAAGAGCTATAAAAAATCAAGCACATAAACCTTTGTTCCGNCTATAAAACACAGAAACGCACCCTCACGCACCATGTGCCG
CCCCACCCTGTTCTACCACACGTGTCCCCTGAGTGCGAATTACCTTACGCACAGTTGGAAAAAAGGGGACTAATATCGGTGTGNGATACAAAGGCGTGTGGACTC
ATGAGTTTTTTCTTTTTCTAGGTTCGGGGGGNCAGNNNNNNNNTNNNNNGATTTTTTTCTTTNNNNNNNGNGNN

SEQUENCE LISTING

```
<160> NUMBER OF SEQ ID NOS: 52

<210> SEQ ID NO 1
<211> LENGTH: 37
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(37)
<223> OTHER INFORMATION: n is a, t, c, or g

<400> SEQUENCE: 1
nnnnnnnnnn nnnnnnnnnn nnnnnnnnnn nnnnnnn                        37

<210> SEQ ID NO 2
<211> LENGTH: 60
<212> TYPE: DNA
<213> ORGANISM: Artificial Sequence
<220> FEATURE:
<223> OTHER INFORMATION: synthetic construct

<400> SEQUENCE: 2
ccgactacgt ggtccagtgt caccacgtaa tgcacgcggt gattaccacc cctagcaagg    60

<210> SEQ ID NO 3
```

```
<211> LENGTH: 60
<212> TYPE: DNA
<213> ORGANISM: Artificial Sequence
<220> FEATURE:
<223> OTHER INFORMATION: synthetic construct

<400> SEQUENCE: 3
ccttgctagg ggtggtaatc accgcgtgca ttacgtggtg acactggacc acgtagtcgg    60

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
gtgtcaccac gtaatgcacg                                                20

<210> SEQ ID NO 5
<211> LENGTH: 33
<212> TYPE: DNA
<213> ORGANISM: Artificial Sequence
<220> FEATURE:
<223> OTHER INFORMATION: synthetic construct

<400> SEQUENCE: 5
ccgactacgt ggtccagtgt caccacgtaa tgc                                 33

<210> SEQ ID NO 6
<211> LENGTH: 27
<212> TYPE: DNA
<213> ORGANISM: Artificial Sequence
<220> FEATURE:
<223> OTHER INFORMATION: synthetic construct

<400> SEQUENCE: 6
acgcggtgat taccacccct agcaagg                                        27

<210> SEQ ID NO 7
<211> LENGTH: 33
<212> TYPE: DNA
<213> ORGANISM: Artificial Sequence
<220> FEATURE:
<223> OTHER INFORMATION: synthetic construct

<400> SEQUENCE: 7
gcattacgtg gtgacactgg accacgtagt cgg                                 33

<210> SEQ ID NO 8
<211> LENGTH: 27
<212> TYPE: DNA
<213> ORGANISM: Artificial Sequence
<220> FEATURE:
<223> OTHER INFORMATION: synthetic construct

<400> SEQUENCE: 8
ccttgctagg ggtggtaatc accgcgt                                        27

<210> SEQ ID NO 9
<211> LENGTH: 20
<212> TYPE: DNA
<213> ORGANISM: Artificial Sequence
<220> FEATURE:
<223> OTHER INFORMATION: synthetic construct

<400> SEQUENCE: 9
```
tgatgcacca ggtcacagtg                                              20

<210> SEQ ID NO 10
<211> LENGTH: 60
<212> TYPE: DNA
<213> ORGANISM: Artificial Sequence
<220> FEATURE:
<223> OTHER INFORMATION: synthetic construct

<400> SEQUENCE: 10
ggaacgatcc ccaccattag tggcgcacgt aatgcaccac tgtgacctgg tgcatcagcc    60

<210> SEQ ID NO 11
<211> LENGTH: 60
<212> TYPE: DNA
<213> ORGANISM: Artificial Sequence
<220> FEATURE:
<223> OTHER INFORMATION: synthetic construct

<400> SEQUENCE: 11
ggctgatgca ccaggtcaca gtggtgcatt acgtgcgcca ctaatggtgg ggatcgttcc    60

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
acgatcccca ccattagtgg                                              20

<210> SEQ ID NO 13
<211> LENGTH: 60
<212> TYPE: DNA
<213> ORGANISM: Artificial Sequence
<220> FEATURE:
<223> OTHER INFORMATION: synthetic construct

<400> SEQUENCE: 13
ccgactacgt ggtccagtgt caccacgtaa tgcacgcggt gattaccacc cctagcaagg    60

<210> SEQ ID NO 14
<211> LENGTH: 60
<212> TYPE: DNA
<213> ORGANISM: Artificial Sequence
<220> FEATURE:
<223> OTHER INFORMATION: synthetic construct

<400> SEQUENCE: 14
ccttgctagg ggtggtaatc accgcgtgca ttacgtggtg acactggacc acgtagtcgg    60

<210> SEQ ID NO 15
<211> LENGTH: 20
<212> TYPE: DNA
<213> ORGANISM: Artificial Sequence
<220> FEATURE:
<223> OTHER INFORMATION: synthetic construct

<400> SEQUENCE: 15
tgatgcacca ggtcacagtg                                              20

<210> SEQ ID NO 16
<211> LENGTH: 60
<212> TYPE: DNA

```
<213> ORGANISM: Artificial Sequence
<220> FEATURE:
<223> OTHER INFORMATION: synthetic construct

<400> SEQUENCE: 16
ggaacgatcc ccaccattag tggcgcacgt aatgcaccac tgtgacctgg tgcatcagcc    60

<210> SEQ ID NO 17
<211> LENGTH: 60
<212> TYPE: DNA
<213> ORGANISM: Artificial Sequence
<220> FEATURE:
<223> OTHER INFORMATION: synthetic construct

<400> SEQUENCE: 17
ggctgatgca ccaggtcaca gtggtgcatt acgtgcgcca ctaatggtgg ggatcgttcc    60

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
acgatcccca ccattagtgg                                                20

<210> SEQ ID NO 19
<211> LENGTH: 60
<212> TYPE: DNA
<213> ORGANISM: Artificial Sequence
<220> FEATURE:
<223> OTHER INFORMATION: synthetic construct

<400> SEQUENCE: 19
ccgactacgt ggtccagtgt caccacgtaa tgcacgcggt gattaccacc cctagcaagg    60

<210> SEQ ID NO 20
<211> LENGTH: 60
<212> TYPE: DNA
<213> ORGANISM: Artificial Sequence
<220> FEATURE:
<223> OTHER INFORMATION: synthetic construct

<400> SEQUENCE: 20
ccttgctagg ggtggtaatc accgcgtgca ttacgtggtg cactggacc acgtagtcgg     60

<210> SEQ ID NO 21
<211> LENGTH: 24
<212> TYPE: DNA
<213> ORGANISM: Felis catus

<400> SEQUENCE: 21
gtggccgcaa cagtagggca gggt                                           24

<210> SEQ ID NO 22
<211> LENGTH: 24
<212> TYPE: DNA
<213> ORGANISM: Artificial Sequence
<220> FEATURE:
<223> OTHER INFORMATION: synthetic construct

<400> SEQUENCE: 22
gtggccgcaa cagtagggca gggg                                           24
```

```
<210> SEQ ID NO 23
<211> LENGTH: 32
<212> TYPE: DNA
<213> ORGANISM: Artificial Sequence
<220> FEATURE:
<223> OTHER INFORMATION: synthetic construct

<400> SEQUENCE: 23
tgctgtggcc gcaacagtag ggcaggggtg gg                             32

<210> SEQ ID NO 24
<211> LENGTH: 23
<212> TYPE: DNA
<213> ORGANISM: Felis catus

<400> SEQUENCE: 24 gagggggggca ctgcttgtgc tgg                                      23

<210> SEQ ID NO 25
<211> LENGTH: 24
<212> TYPE: DNA
<213> ORGANISM: Artificial Sequence
<220> FEATURE:
<223> OTHER INFORMATION: synthetic construct

<400> SEQUENCE: 25 gagggggggca ctgcttgttg ctgg                                     24

<210> SEQ ID NO 26
<211> LENGTH: 31
<212> TYPE: DNA
<213> ORGANISM: Artificial Sequence
<220> FEATURE:
<223> OTHER INFORMATION: synthetic construct

<400> SEQUENCE: 26
aatgccagca acaagcagtg ccccccctcat c                             31

<210> SEQ ID NO 27
<211> LENGTH: 23
<212> TYPE: DNA
<213> ORGANISM: Felis catus

<400> SEQUENCE: 27
gtggccgcaa cagtagggca ggg                                       23

<210> SEQ ID NO 28
<211> LENGTH: 22
<212> TYPE: DNA
<213> ORGANISM: Artificial Sequence
<220> FEATURE:
<223> OTHER INFORMATION: synthetic construct

<400> SEQUENCE: 28
gtggccgcaa cagtaggcag gg                                        22

<210> SEQ ID NO 29
<211> LENGTH: 41
<212> TYPE: DNA
<213> ORGANISM: Artificial Sequence
<220> FEATURE:
<223> OTHER INFORMATION: synthetic construct

<400> SEQUENCE: 29
tgctgtggcc gcaacagtag gcagggtggg gagggctgcg t                   41
```

-continued

```
<210> SEQ ID NO 30
<211> LENGTH: 23
<212> TYPE: DNA
<213> ORGANISM: Felis catus

<400> SEQUENCE: 30 gagggggggca ctgcttgtgc tgg                                              23

<210> SEQ ID NO 31
<211> LENGTH: 24
<212> TYPE: DNA
<213> ORGANISM: Artificial Sequence
<220> FEATURE:
<223> OTHER INFORMATION: synthetic construct

<400> SEQUENCE: 31 gagggggggca ctgcttggtg ctgg                                             24

<210> SEQ ID NO 32
<211> LENGTH: 31
<212> TYPE: DNA
<213> ORGANISM: Artificial Sequence
<220> FEATURE:
<223> OTHER INFORMATION: synthetic construct

<400> SEQUENCE: 32
gatgaggggg gcactgcttg gtgctggcat t                                      31

<210> SEQ ID NO 33
<211> LENGTH: 482
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(10)
<223> OTHER INFORMATION: n is a, g, c, or t
<220> FEATURE:
<221> NAME/KEY: misc_feature
<222> LOCATION: (14)..(16)
<223> OTHER INFORMATION: n is a, g, c, or t
<220> FEATURE:
<221> NAME/KEY: misc_feature
<222> LOCATION: (18)..(21)
<223> OTHER INFORMATION: n is a, g, c, or t
<220> FEATURE:
<221> NAME/KEY: misc_feature
<222> LOCATION: (267)..(267)
<223> OTHER INFORMATION: n is a, g, c, or t
<220> FEATURE:
<221> NAME/KEY: misc_feature
<222> LOCATION: (390)..(390)
<223> OTHER INFORMATION: n is a, g, c, or t
<220> FEATURE:
<221> NAME/KEY: misc_feature
<222> LOCATION: (442)..(442)
<223> OTHER INFORMATION: n is a, g, c, or t
<220> FEATURE:
<221> NAME/KEY: misc_feature
<222> LOCATION: (446)..(452)
<223> OTHER INFORMATION: n is a, g, c, or t
<220> FEATURE:
<221> NAME/KEY: misc_feature
<222> LOCATION: (454)..(457)
<223> OTHER INFORMATION: n is a, g, c, or t
<220> FEATURE:
<221> NAME/KEY: misc_feature
<222> LOCATION: (470)..(477)
<223> OTHER INFORMATION: n is a, g, c, or t
<220> FEATURE:
<221> NAME/KEY: misc_feature
```

```
<222> LOCATION: (479)..(479)
<223> OTHER INFORMATION: n is a, g, c, or t
<220> FEATURE:
<221> NAME/KEY: misc_feature
<222> LOCATION: (481)..(482)
<223> OTHER INFORMATION: n is a, g, c, or t

<400> SEQUENCE: 33
nnnnnnnnnn gcannncnnn nctggtggcc aagcagcgtt gagcagcctg ggccagcccc      60
aaagcttgag gggtaggctg aatcttcccc acatgatccc ctctacttcc ccagccatgg     120
cgtctttctc ctcccagatt cccagggaag ggccatggtg gagaacaaac atgagcaacc     180 ccctcctgc actgccctga gcagaccccc cggggacatg gcaggtaaga gctataaaaa      240
atcaagcaca taaacctttg ttccgcncta taaaacacag aaaacgcacc ctcacgccat     300
gtgcgccccc accctgttct accacacgtg tccctgagt gcgaattacc ttacgcacag      360
ttggaaaaaa ggggactaat atcggtgtgn gatacaaagc gtgtggactc atatgagttt     420
tttctttcta ggttcggggg gncagnnnnn nntnnnngat ttttttcttt nnnnnnngng     480 nn                                                                   482

<210> SEQ ID NO 34
<211> LENGTH: 49
<212> TYPE: DNA
<213> ORGANISM: Felis catus

<400> SEQUENCE: 34
tcctgcactg ccctgagcag acccccaga caggcgtcag aggcacaga                  49

<210> SEQ ID NO 35
<211> LENGTH: 53
<212> TYPE: DNA
<213> ORGANISM: Felis catus

<400> SEQUENCE: 35
tgccctgagc agaccccca gacaggcgtc agaggcacag acacagagct aga              53

<210> SEQ ID NO 36
<211> LENGTH: 51
<212> TYPE: DNA
<213> ORGANISM: Felis catus

<400> SEQUENCE: 36 tcagggggttc ccatcaggaa taggtcaaca tccctcttca cggctgggca a              51

<210> SEQ ID NO 37
<211> LENGTH: 47
<212> TYPE: DNA
<213> ORGANISM: Felis catus

<400> SEQUENCE: 37
tattccacat acagaccatg cagtcagggg ctacatggca ggtaaga                    47

<210> SEQ ID NO 38
<211> LENGTH: 54
<212> TYPE: DNA
<213> ORGANISM: Felis catus

<400> SEQUENCE: 38
ttcacgttgc gcgtgcagca gattgtaata ttccacatac agaccatgca gtca            54

<210> SEQ ID NO 39
```

```
<211> LENGTH: 54
<212> TYPE: DNA
<213> ORGANISM: Felis catus

<400> SEQUENCE: 39
tcagcggaaa cttgccccat tttttatgac gtctttttg cggtggccaa tgga          54

<210> SEQ ID NO 40
<211> LENGTH: 19
<212> TYPE: DNA
<213> ORGANISM: Artificial Sequence
<220> FEATURE:
<223> OTHER INFORMATION: synthetic construct

<400> SEQUENCE: 40
actgaggcca agtgatgcc                                                19

<210> SEQ ID NO 41
<211> LENGTH: 20
<212> TYPE: DNA
<213> ORGANISM: Artificial Sequence
<220> FEATURE:
<223> OTHER INFORMATION: synthetic construct

<400> SEQUENCE: 41
ctgacacccc gaacctagaa                                               20

<210> SEQ ID NO 42
<211> LENGTH: 20
<212> TYPE: DNA
<213> ORGANISM: Artificial Sequence
<220> FEATURE:
<223> OTHER INFORMATION: synthetic construct

<400> SEQUENCE: 42
cctgtggaag gctaaaatcc                                               20

<210> SEQ ID NO 43
<211> LENGTH: 20
<212> TYPE: DNA
<213> ORGANISM: Artificial Sequence
<220> FEATURE:
<223> OTHER INFORMATION: synthetic construct

<400> SEQUENCE: 43
ggctgccttg ctcttgatct                                               20

<210> SEQ ID NO 44
<211> LENGTH: 20
<212> TYPE: DNA
<213> ORGANISM: Artificial Sequence
<220> FEATURE:
<223> OTHER INFORMATION: synthetic construct

<400> SEQUENCE: 44
gatgttgacc tattcctgac                                               20

<210> SEQ ID NO 45
<211> LENGTH: 23
<212> TYPE: DNA
<213> ORGANISM: Artificial Sequence
<220> FEATURE:
<223> OTHER INFORMATION: synthetic construct

<400> SEQUENCE: 45
ccatcaggaa taggtcaaca tcc                                           23
```

<210> SEQ ID NO 46
<211> LENGTH: 20
<212> TYPE: DNA
<213> ORGANISM: Artificial Sequence
<220> FEATURE:
<223> OTHER INFORMATION: synthetic construct

<400> SEQUENCE: 46 gagggggggca ctgcttgtgc                                              20

<210> SEQ ID NO 47
<211> LENGTH: 24
<212> TYPE: DNA
<213> ORGANISM: Artificial Sequence
<220> FEATURE:
<223> OTHER INFORMATION: synthetic construct

<400> SEQUENCE: 47
gtcttttttg cggtggccaa tgga                                          24

<210> SEQ ID NO 48
<211> LENGTH: 19
<212> TYPE: DNA
<213> ORGANISM: Artificial Sequence
<220> FEATURE:
<223> OTHER INFORMATION: synthetic construct

<400> SEQUENCE: 48
actgaggcca agtgatgcc                                                19

<210> SEQ ID NO 49
<211> LENGTH: 20
<212> TYPE: DNA
<213> ORGANISM: Artificial Sequence
<220> FEATURE:
<223> OTHER INFORMATION: synthetic construct

<400> SEQUENCE: 49
ctgacacccc gaacctagaa                                               20

<210> SEQ ID NO 50
<211> LENGTH: 20
<212> TYPE: DNA
<213> ORGANISM: Artificial Sequence
<220> FEATURE:
<223> OTHER INFORMATION: synthetic construct

<400> SEQUENCE: 50
cctgtggaag gctaaaatcc                                               20

<210> SEQ ID NO 51
<211> LENGTH: 2565
<212> TYPE: DNA
<213> ORGANISM: Felis catus
<220> FEATURE:
<221> NAME/KEY: misc_feature
<222> LOCATION: (1839)..(2392)
<223> OTHER INFORMATION: n is a, g, c, or t

<400> SEQUENCE: 51
gcctttggag cttctggggg ggggggtgtg ggctgggctt aagtgctag tagtttataa    60 agcagcagaa atcctgtcct gagcagagca ttctagcagc tgacacgatg aggggggcac  120
tgcttgtgct ggcattgctg gtgacccaag agctgggcgt caagatgggt gagagcagat  180

```
ggagggacag aggaccttcc tgatccttgc cctgctctat ctcactcctt tacctcccat    240
ggtgatctcc aaacaggttc tagccacaaa gttaagcggc agctgggaga tcattgtcca    300
ggagtcctgc agaaccccc tggtgttttt agtcgtagaa tggagggaga ggtttggaga    360
tggagggatc attagttgtg cacacaatag gggagagtta gttgggggta gtggtgctta    420
tttgaaaggc cgaaacaggc aggctgggt gcccggaggc accggtcagg ggtctctccg    480
gctgctctct tctgctgaga gtgcctcata gaaaatgttc cgtctgtctg ggatgtaagc    540
agtcctggga gtgggcaggt ctctgcggaa ggtgagtcag aagaccctgg atatatgtga    600
gttgctctca gtggcgggc aaacaggaac ctcctgctct gctgattctt ttgtgaaggt    660
gttttctgtt tgtgtcttca gcggaaactt gccccatttt ttatgacgtc tttttttgcgg    720 tggccaatgg aaatgaatta ctgttggact tgtccctcac aaaagtcaat gctactgaac    780
cagagagaac agccatgaaa aaaatccagg attgctacgt ggagaacgga ctcttatcca    840
gggtcttgga tggactagtc atggtaattt ccttttcctc cccgcctccc aaccttcac    900 gttgcgcgtg cagcagattg taatattcca catacagacc atgcagtcag ggctacatg    960 gcaggtaaga gctataaaca atcgagcaca taaacctttg ctccgctcta cagcacatag   1020
aatacgcaac ctcacgccat gtgcacaccc agcctgttct tctaccacac gtgtcccttg   1080
tgtgcgaatt accttacgca cagttggaaa atagggggact aatatcggtg tggcatagaa   1140
agcgtgttga ctcgtaggat ttttttcttt ctaggttcgg ggtgtcagaa ttgcaggagt   1200
aggattttag ccttccacag gaaagagaaa gttcttcatt cagctcctgc acatgtagga   1260
gccttgtcag ttctggtgga ggaatattga aactaaggca cctgccctca gactctcttc   1320
ccaggaaggg actccctggc tttgggaagc ttctggtttt tggcttctgt tttacttccc   1380
cttgtgccca ccttgatggc tgctattcct ttggttcaga gtctcacttc cttctgtatc   1440
aattcagggt ctaaagtcag attttccact ctgttgttct ggtgcctgag ccctcgagg   1500 cagctcctag ctacgtgcag ctgcaccca gggctggtca gtgtatttct ggtgaactat   1560 cttttctgt tattttctt gttgcacagt taggtcgatt ttggttagtc tgtctcttac   1620
ctctacttgc cgttaagtgc tgattctgta aaatgagagc tttgtgaaga agtggaattt   1680
cttgcatgac tacgggcacc cagggcacat gggattgttc acaacacaca catacacatt   1740
ccatacatcc agtacacctg acagatgagt ctcaggtgag ggagacatcg catgacccca   1800
gactcagcta ccttgcccct cacccaggcc cagccccnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nngctggatc   2400
cagacacctg tcctcaccta attcactctc aatcaggctg actagaataa aataactgca   2460
tcttagcacc cccgggtgcc ccgtgtctgt gttctgtgcg ggaagcgtgg gaggcctggc   2520
aggagatcct gggacatggc aaagggaggt gacatgtgct cattg                   2565
```

<210> SEQ ID NO 52
<211> LENGTH: 2131
<212> TYPE: DNA
<213> ORGANISM: Felis catus

<400> SEQUENCE: 52

| | | | | | |
|---|---|---|---|---|---|
| aaggtagcgt | catctgttga | ctcggggact | taggatcctg | cccacacata | catctcctcc | 60 |
| ctccacagcc | cccaggcagt | tctgagaagc | agcccagaga | ggcctggcgg | tgcctcctgg | 120 |
| aaaaggatgt | tagacgcagc | cctcccaccc | tgccctactg | ttgcagccac | agcaggtata | 180 |
| aaagggttcc | aggctgggga | gggagcacct | gccactgcat | catgaagggg | gctcgtgttc | 240 |
| tcgtgcttct | ctgggctgcc | ttgctcttga | tctcgggtgg | aagtaggtgt | ctgggacatg | 300 |
| agtgtctggg | gacacagatt | ctccaggggt | tctaacacct | tcccagggca | cttctgagca | 360 |
| tggcgggaag | gggaagggaa | gaatgtgtcc | tgatgaaggt | ctttcaaaag | ggagggtcag | 420 |
| cttgtctttg | tgttccagat | tgtgaaattt | gcccagccgt | gaagagggat | gttgacctat | 480 |
| tcctgatggg | aaccctgac | aaatatgttg | agcaagtggc | acaatacaat | gcacgacctg | 540 |
| tagtattggc | aaatgccaga | aacctgaaga | actgcgttga | tgcaaaaatg | acagaagagg | 600 |
| ataaggagaa | tgctctcagc | gtgctggtgg | gtctagctct | gtgtctgtgc | ctctgacgcc | 660 |
| tgtctggggg | gtctgctcag | ggcagtgcag | gaggggggtt | gctcatgttt | gttctccacc | 720 |
| atggcccttc | cctgggaatc | tgggaggaga | aagacgccat | ggctggggaa | gtagagggga | 780 |
| tcatgtgggg | aagactcagc | ctacccctca | agctttgggg | ctggcccagg | ctgctcaacg | 840 |
| ctgcttggcc | accggcttgg | gggtctgcag | gccctcctgt | gtccctggca | tcacttggcc | 900 |
| tcagtgtcag | gccctcagct | ctggccttcc | tgactccagc | ctctccagca | cgtgagactg | 960 |
| gatcttcaaa | ctgtttgcac | taggtgcttc | ctatctccaa | acgtcagttc | cttttctctt | 1020 |
| aactcctcaa | gttccatatt | ccaccccccc | cccaaaaaaa | aaccctcatt | tgtcttcatt | 1080 |
| ccctgggtcc | cagagggcca | ttctgtgcct | caaatactga | gagagaggag | gaggggaggg | 1140 |
| gagaagaggg | gcggggcagg | gagggacgag | gggaggtgag | atgggcagc | ttccaaaagc | 1200 |
| cctcccctg | ccctgccatt | ctgtgcctca | cataccaaga | gagaggatga | tggaagggga | 1260 |
| ggggagggga | ggggagggga | ggggagggga | ggggagggga | gggagagga | gaggagagga | 1320 |
| gaggagagga | gaggagagga | gaggagagga | gaggagagga | gaggagaggc | agcttccaaa | 1380 |
| aagttctcct | gccctgccca | ggcctgggat | gccctgagtg | gagaattcca | gtgaatcctc | 1440 |
| tctctgctgt | cccaaaagta | ggaacaagct | actgcttcag | caacaagtgt | tcaaaggaca | 1500 |
| gaaggaggaa | gcaggctgga | ccagctcatt | cctggagtct | cccagatgcc | cacaggtgca | 1560 |
| tctggagccc | tgccaggacc | ttcttgccag | cctctttcta | tccaagtcta | ccacttctat | 1620 |
| ccgagactgc | cctccatccc | atcatagtca | ccctcttct | tcactctgtt | tcattggagg | 1680 |
| aagcttctag | gcacaccctg | ggattctctt | gttgtgcagt | agattgggaa | gaaccacctt | 1740 |
| ggcctgctca | gatccagaag | ccaccctcca | aacaagcctg | caggctcctc | cccacaaagt | 1800 |
| gtccagtgcg | tgctcagtag | agcttgatgt | ctcgcgtacc | cctcaaggtc | tcaccaggtc | 1860 |
| tcctgacttt | ctcttttgcag | gacaaaatat | acacaagtcc | tctgtgttaa | tggagccatc | 1920 |
| actgccagga | gccctaagga | agccactgaa | ctgattacta | agtagtctca | gcagcctgcc | 1980 |

```
atgtccaggt gtcttactag aggattccag caataaaagc cttgcaattc atggagagtg    2040
cttgctcctt gggctgggct tggggggggg ggtggagggg tgttgcagca gggggaccac    2100
cagtgtgcct tccaaccgtg gctagatttg a                                   2131
```

METHODS FOR PRODUCING HYPO-ALLERGENIC CATS USING GENE EDITING TECHNOLOGY

FIELD OF THE INVENTION

This invention relates to the production of genetically modified animals wherein a recognized gene sequence, coding for an identified allergen, is modified, inactivated, or removed so that it can no longer produce an allergic response in humans. More particularly, the invention relates to genetically modified cats wherein the gene sequence coding for the major cat allergen Fel d I has been disrupted using engineered nucleases composed of programmable, sequence-specific, DNA-binding modules fused to a non-specific DNA cleavage domain.

BACKGROUND OF THE INVENTION

Cat allergies are a significant worldwide health problem. In the US alone, nearly 10% of the population, or 33 million people, are allergic to cats. People with cat allergies struggle with rhinorrhea, facial pain, sneezing, swollen eyes, itchy throats, and difficulties breathing[i]. When evaluated, almost all of these patients will show a positive immediate hypersensitivity reaction when skin tested to extracts of cat dander and will have serum IgE antibodies against the major cat allergen, Fel d I[ii]. Further, cat allergen has been identified as a major risk factor for developing childhood allergies, and other respiratory diseases, such as bronchitis and asthma, that persist through adulthood.

To date, most treatments to cat sensitivity have focused on avoidance, immunotherapy, and pharmaceuticals. Avoidance typically means choosing to live without a pet, or making considerable alterations in the living environment to minimize exposure to cat allergen. For example, to avoid excessive exposure to indoor allergens it is recommended that carpets be removed from floors, bedding be covered with special sheets, air conditioners be cleaned regularly, and costly air filters be replaced quarterly. Some have even recommended bathing the cat regularly to reduce the amount of cat allergen in the household environment[iii]. The expense, effort and relative ineffectiveness of these strategies makes this option unappealing to allergy sufferers.

Immunization can be an effective treatment for allergies[iv]. Unfortunately, allergy shots are not always effective, and completing treatment can take several years. They are also not safe for children under the age of 5. The expense of regular allergy shots, the time involved to receive treatment, and the variability of effectiveness are considerable deterrents for most patients. Furthermore, there is risk that a person may have a severe reaction to the immunization, resulting in anaphylactic shock and possible death.

Pharmaceuticals such as nasal steroid sprays, oral antihistamines, inhaled corticosteroids, bronchodilators, and antihistamine eye drops are frequently prescribed to treat cat allergies[v]. Many of these pharmaceuticals are expensive brand name drugs with no generic equivalent and demonstrate variable effectiveness.

SUMMARY OF INVENTION

This invention describes new methods to produce Fel d I "knock-out" cats. The Fel d I locus is comprised of two genes, chain 1 and chain 2, flanked on each side by downstream sequences and sharing a common promoter. Gene editing tools that are highly efficient and specific for targeting the Fel d I locus and flanking sequences are used to disrupt the Fel d I locus and create a Fel d I "knock-out." The gene editing tools are designed to target the different regions that comprise the Fel d I locus and are used to disrupt chain 1, chain 2, the shared promoter, the flanking sequences, and/or a combination of part or all of chain 1, chain 2, the shared promoter, and the flanking sequences. Further, the gene editing tools described herein do not require complicated selection strategies to identify cells in which the Fel d I locus has been successfully targeted. The technology described herein can be used to create a breed of hypoallergenic cats that lack the major cat allergen, Fel d I. These hypoallergenic cats are fertile and can pass on the desired hypoallergenic genotype and phenotype to their offspring through traditional breeding methods.

A Fel d I gene is "disrupted" or "knocked out," as described herein, by deletion or mutation of Fel d I coding and/or regulatory sequences, so that the gene cannot be transcribed to generate functional Fel d I mRNA, and thus cannot generate functional Fel d I protein. Such a deletion or mutation results in the production of at least 50%, 75%, 80%, 85%, 90%, 95%, 99%, or 100% less Fel d I mRNA and/or Fel d I protein, as compared to a Fel d I sequence lacking the deletion or mutation. As described herein, a disrupted or knocked out Fel d I gene can be present in a cell, which optionally is in a cat, in heterozygous or homozygous form. The deletions or mutations can be present in one or more of the following elements of the Fel d I locus, or combinations thereof (e.g., all of the elements), as described elsewhere herein: the Fel d I promoter, Fel d I chain 1, Fel d I chain 2, exon 1 of Fel d I chain 1, exon 2 of Fel d I chain 1, exon 3 of Fel d I chain 1, exon 1 of Fel d I chain 2, exon 2 of Fel d I chain 2, and exon 3 of Fel d I chain 2. In various examples, one or more element is deleted in its entirety, while in other examples, a frameshift mutation, resulting in the production of nonsense mRNA, which may generate nonsense protein, is introduced into a sequence encoding one or more of the elements. In addition, a deletion can be made by making cuts within elements, as described herein, or by making cuts in flanking sequences, as would be understood by those of skill in the art. Further, in various examples, a Fel d I disruption or knock-out results in the production of no Fel d I mRNA, and thus no Fel d I protein.

This invention describes the use of programmable, sequence-specific DNA-binding modules linked to a non-specific DNA cleavage domain to efficiently and precisely "knock-out" the Fel d I locus by inducing targeted DNA double-strand breaks into one of the Fel d I genes, both of the Fel d I genes, the flanking sequences, or the shared promoter. The double-stranded breaks stimulate the cellular repair mechanism. During the cellular repair process, nucleotide insertions, nucleotide deletions, nucleotide substitutions, and/or deletions of chromosomal regions are engineered to disrupt or inactivate one of the Fel d I genes, both of the Fel d I genes, or the shared promoter, resulting in the desired Fel d I "knock-out."

A polynucleotide sequence, or vector, can also be inserted into the Fel d I coding sequence during the repair process. The vector can be engineered to disrupt or replace all or part of the DNA coding sequence resulting in a non-functional gene. Further, the polynucleotide sequence may be designed to encode for a selectable marker such as GFP or Neomycin resistance. The selectable markers aid in identifying cells in which desired gene editing has occurred. The selectable marker may be inserted into the coding sequence of the Fel d I gene or used to replace all or part of the gene.

A site-specific engineered nuclease can be introduced into a variety of cell types including embryos, stem cells, somatic cells such as fibroblasts, and induced pluripotent stem cells (iPS cells). The site-specific nucleases are introduced into the cell in the form of plasmids, DNA, RNA, or protein. This versatility facilitates rapid generation of cell lines and cats with the Fel d I null phenotype. In the case where the site-specific nuclease is injected into an embryonic stem cell, somatic cell, or iPS cell a Fel d I "knock-out" clonal cell line is identified, isolated, and expanded. A nucleus from a Fel d I modified clonal cell line is then transferred to an enucleated feline oocyte or one-cell embryo in a process referred to as reproductive cloning. The reconstructed embryos are then implanted into surrogate feline recipients. These genetically modified embryos retain the ability to support fetal development. A change in the genomic sequence of the embryos will be passed on to all other cells derived directly from the modified embryos including the germ line. The resulting offspring are heterozygous and homozygous "knock-outs" for the Fel d I genes.

Alternatively, the engineered site-specific nucleases are introduced directly into fertilized eggs or one-cell stage feline embryos. As is the case with nuclear transfer, any change in the genome of the embryo will be passed on to some or all of the cells derived directly from the modified embryos. The modified embryos are then implanted into surrogate feline recipients where they are carried to term. A proportion of the resulting offspring are Fel d I heterozygous and homozygous "knock-outs." Whether produced through nuclear transfer or direct embryo injection, the heterozygous and homozygous Fel d I "knock-out" cats are naturally bred with one another to establish lines of homozygous hypoallergenic cats with the Fel d I null mutation that is transmissible to subsequent generations.

This invention is applicable to all animals in which a specific allergen can be identified and in which the disruption of the gene sequence coding for the particular allergen results in a null mutation.

This invention is based on the production of genetically modified animals in which the gene sequence for a particular allergen has been disrupted by a specialized construct rendering the gene inactive. In a preferred embodiment the altered gene will be transmissible to the offspring.

In yet another embodiment, the present invention provides a genetically modified cat comprising a disrupted Fel d I locus. The Fel d I locus of the somatic cells, the germ line cells, or both the somatic and germ line cells of such a genetically modified cat may be disrupted. In accordance with the invention, there is provided a genetically modified cat which is heterozygous for the disrupted Fel d I gene. There also is provided a genetically modified cat which is homozygous for said disrupted Fel d I locus. Genetically modified cats comprising a disrupted Fel d I locus are provided that are fertile and capable of transmitting said disrupted Fel d I locus to their offspring are also provided.

The present invention also provides a first method for producing a genetically modified cat containing a disrupted Fel d I gene, comprising the steps of:
(a) introducing an engineered nuclease composed of programmable, sequence-specific, DNA-binding modules fused to a non-specific DNA cleavage domain designed to disrupt the coding or regulatory sequences of Fel d I locus into a feline embryo;
(b) transferring said embryo into a feline surrogate recipient; and
(c) allowing said cat embryo to mature into a cat.

The present invention also provides a second method for producing a genetically modified cat containing a disrupted Fel d I locus, comprising the steps of:
(a) introducing an engineered nuclease composed of programmable, sequence-specific, DNA-binding modules fused to a non-specific DNA cleavage domain designed to disrupt the coding sequence of the Fel d I genes or shared promoter into a feline somatic cell, embryonic stem cell, or induced pluripotent stem cell;
(b) identifying a cell in which the Fel d I locus has been successfully disrupted by the engineered nuclease:
(c) transferring the nucleus of said cell into an enucleated embryo;
(d) implanting said embryo into a feline surrogate recipient; and
(e) allowing said cat embryo to mature into a cat.

Genetically modified cats produced in accordance with these methods can be homozygous for the disrupted Fel d I gene. Homozygous genetically modified cats will not produce the Fel d I cat allergen.

In another embodiment of the present invention, there is provided a third method for producing a genetically modified cat comprising a disrupted Fel d I gene, wherein said cat does not produce the cat allergen Fel d I, and wherein said cat is heterozygous for said disrupted Fel d I gene, comprising the steps of:
(a) producing a first heterozygous genetically modified cat according to the methods described above;
(b) producing a second heterozygous genetically modified cat according to the methods described above, wherein said second cat is not the same sex as said first cat;
(c) breeding said first and second cats; and
(d) selecting genetically modified cats which are homozygous for said disrupted Fel d I gene and do not produce Fel d I antigen.

As a fourth method for producing a genetically modified cat containing a disrupted Fel d I gene, the following steps describe combining nucleases with a targeting or donor vector. In this case, the donor vector functions as a template for the double stranded break repair. The inserted sequence is used to select clones with successful integration of the vector. If desired, the inserted sequence can later be excised from the cells:
(a) introducing engineered nucleases composed of programmable, sequence-specific, DNA-binding modules fused to a non-specific DNA cleavage domain designed to disrupt the coding sequence of Fel d I into a feline embryo in addition to a vector or DNA molecule exhibiting sequence homology to the sequence surrounding the target site, which may or may not contain a selectable marker;
(b) transferring said embryo into a feline surrogate recipient; and
(c) allowing said cat embryo to mature into a cat.

These methods create heterozygous or homozygous animals for the targeted Fel d I alleles. Heterozygous cats are bred to homozygosity by breeding heterozygotes to heterozygotes. Alternatively, heterozygotes are bred to wild type cats and the resulting offspring are bred to each other or other heterozygote animals to produce homozygous Fel d I knock-outs.

The invention thus provides feline embryonic stem cells or feline induced pluripotent stem cells (iPSCs) that can be maintained in culture in a pluripotent state for more than 5 (e.g., more than 10, 15, 20, or 25) passages. The cells can optionally be maintained in a pluripotent state independently from a cytokine of the interleukin-6 family (e.g., leukemia inhibitory factor (LIF)). Optionally, the cells can be cultured in the presence of basic fibroblast growth factor (bFGF) and, further optionally, an agonist of the transforming growth factor-beta (TGF-beta) superfamily (e.g., activin, nodal, TGFb1, and TGFb3). Further, the cells may optionally express transcription factor Oct4 and/or Nanog. In addition, the cells may differentiate into multiple tissue types (e.g., tissue types of neurectodermal, mesodermal, or endodermal lineages) in vitro by forming cystic embryoid bodies and/or may form teratomas after grafting into immunocompromised mice.

Also included in the invention are methods of generating feline embryonic stem cells, the methods including: (a) isolating stem cells from the inner cell mass of a cat blastocyst; (b) culturing cells isolated in step (a) in an undifferentiated state using one or more condition selected from the group consisting of: (i) the absence of a cytokine of the interleukin-6 family, such as LIF, (ii) the presence of bFGF and, optionally, one or more agonist of the TGF-beta superfamily, such as activin, nodal, TGFb1, and/or TGFb3, (iii) the absence of homologous inactivated feline embryonic fibroblast layers, and (iv) the presence of mitotically inactivated mouse embryonic fibroblasts (MEFs) or an extracellular matrix, such as matrigel or laminin. These methods may further include passaging the cells by the use of accutase, collagenase, or dispase, but not trypsin. Optionally, the cells are passaged every three-four days, and/or the cells are or can be passaged at least 5, 10, 15, 20, or 25 times.

The invention also includes methods of maintaining feline pluripotent stem cells or feline iPSCs in an undifferentiated state in culture, the methods including culturing the cell in one or more condition selected from the group consisting of: (a) the absence of a cytokine of the interleukin-6 family, such as LIF, (b) the presence of bFGF and, optionally, one or more agonist of the TGF-beta superfamily, such as activin, nodal, TGFb1, and/or TGFb3, (c) the absence of homologous inactivated feline embryonic fibroblast layers, and (d) the presence of mitotically inactivated MEFs or an extracellular matrix such as matrigel or laminin. Optionally, the cells are passaged every three-four days, and/or the cells are or can be passaged at least 5, 10, 15, 20, or 25 times.

The invention also includes methods of generating and maintaining feline iPSCs, the methods including the steps of: (a) expressing transcription factors Oct4, Sox2, cMyc, and Klf4, optionally in combination with Lin28, in a feline fetal or adult somatic cell (e.g., a fibroblast), and (b) maintaining the cells in one or more condition selected from the group consisting of: (i) the absence of a cytokine of the interleukin-6 family, such as LIF, (ii) the presence of bFGF and, optionally, one or more agonist of the TGF-beta superfamily, such as activin, nodal, TGFb1, and/or TGFb3, (iii) the absence of homologous inactivated feline embryonic fibroblast layers, and (iv) the presence of mitotically inactivated MEFs or an extracellular matrix, such as matrigel or laminin. The expression of the transcription factors in the cell can optionally be achieved by the use of a retroviral vector, a lentiviral vector, a Sendai viral vector, plasmid DNA, mini-circle DNA, mRNA, or protein. Further, the methods can include maintaining the cells in an incompletely reprogrammed state for 5 or more passages.

Also included in the invention are methods of producing genetically modified cell lines in which the cells include a disrupted Fel d I gene, the methods including the steps of: providing a feline somatic cell, a feline embryonic stem cell, or a feline iPS cell; (b) introducing an engineered nuclease including a programmable, sequence-specific, DNA binding module fused to a non-specific DNA cleavage domain designed to disrupt coding or non-coding sequences of the Fel d I locus, or flanking DNA sequences, into the feline somatic cell, the feline embryonic stem cell, or the feline iPS cell; screening for a cell containing a correctly targeted Fel d I locus; and expanding a targeted cell line containing a correctly targeted Fel d I locus, wherein the cell line is heterozygous or homozygous for the disrupted Fel d I gene. Optionally, the provided cell is a feline somatic cell, and the feline somatic cell is reprogrammed into an iPS cell after step (b). Further, the disrupted non-coding sequences can optionally include regulatory sequences of the Fel d I locus, which optionally include sequences of the Fel d I promoter. In these methods and the methods described below, the disruptions can be, for example, as described below in connection with the Fel d I elements and combinations thereof, which are disrupted in cells and animals of the invention (see below).

The invention further provides methods for producing genetically modified cats including a disrupted Fel d I gene, the methods including the steps of: (a) introducing an engineered nuclease including a programmable, sequence-specific, DNA-binding module fused to a non-specific DNA cleavage domain designed to disrupt coding or non-coding sequences of the Fel d I locus, or flanking DNA sequences, into a feline embryo; (b) transferring the embryo into a feline surrogate recipient; and (c) allowing the cat embryo to mature into a cat, wherein the cat is heterozygous or homozygous for the disrupted Fel d I gene. Optionally, the disrupted non-coding sequences include regulatory sequences of the Fel d I locus, which optionally include sequences of the Fel d I promoter.

Further, the invention includes methods for producing genetically modified cats including a disrupted Fel d I gene, the methods including the steps of: (a) introducing an engineered nuclease including a programmable, sequence-specific, DNA-binding module fused to a non-specific DNA cleavage domain designed to disrupt coding or non-coding sequences of the Fel d I locus, or flanking DNA sequences, into a feline embryonic stem cell, a feline somatic cell, or a feline iPS cell; (b) identifying a cell in which the Fel d I locus has been disrupted by the engineered nuclease; (c) transferring the nucleus of the cell into an enucleated embryo; (d) implanting the embryo into a feline surrogate recipient; and (e) allowing the cat embryo to mature into a cat, wherein the cat is heterozygous or homozygous for the disrupted Fel d I gene. In various embodiments, the cell of step (a) is a feline somatic cell and the method further includes reprogramming the feline somatic cell into an iPS cell after step (a). In other embodiments, the cell of step (a) is an iPS cell that was reprogrammed from a feline somatic cell prior to step (a). Further, in additional embodiments, the cell of step (a) is an embryonic stem cell, which is derived from an inner cell mass of a feline blastocyst.

The invention also provides methods for producing genetically modified cats containing a disrupted Fel d I gene, the methods including the steps of: (a) introducing an engineered nuclease including a programmable, sequence-specific, DNA-binding module fused to a non-specific DNA cleavage domain designed to disrupt coding or non-coding sequences of the Fel d I locus, or flanking DNA sequences, into a feline embryo in addition to a vector or DNA molecule exhibiting sequence homology to sequences surrounding the target site, which may or may not contain a selectable marker; (b) transferring the embryo into a feline surrogate recipient; and (c) allowing the cat embryo to mature into a cat, wherein the cat is heterozygous or homozygous for the disrupted Fel d I gene.

Also, the invention includes methods for producing genetically modified cats including a disrupted Fel d I gene, the methods including the steps of: (a) introducing an engineered nuclease including a programmable, sequence-specific, DNA-binding module fused to a non-specific DNA cleavage domain designed to disrupt coding or non-coding sequences of the Fel d I locus, or flanking DNA sequences, into a feline embryonic stem cell, a feline somatic cell, or a feline iPS cell, in addition to a vector or DNA molecule exhibiting sequence homology to sequences surrounding the target site, which may or may not contain a selectable marker; (b) identifying a cell in which the Fel d I locus has been disrupted by the engineered nuclease; (c) transferring the nucleus of the cell of (b) into an enucleated embryo; (d) transferring the embryo into a feline surrogate recipient; and (e) allowing the embryo to mature into a cat, wherein the cat is heterozygous or homozygous for the disrupted Fel d I gene. In various embodiments, the cell of step (a) is a feline somatic cell and the method further includes reprogramming the feline somatic cell into an iPS cell after step (a). In other embodiments, the cell of step (a) is an iPS cell that was reprogrammed from a feline somatic cell prior to step (a). In further embodiments, the cell of step (a) is an embryonic stem cell, which is derived from an inner cell mass of a feline blastocyst.

In any of the methods described herein, for making cats, and in which the mature cat is heterozygous for the targeted Fel d I allele, the methods can further include: (a) breeding the cat to homozygosity by breeding with another heterozygote to produce a homozygous Fel d I knock-out; or (b) breeding the cat to a wild type cat, and breeding the resulting offspring to each other or other heterozygote cats to produce a homozygous Fel d I knock-out.

In addition, in any of the methods described herein, in which a Fel d I gene is disrupted, the engineered nuclease can optionally be selected from the group consisting of: Cas9, a zinc finger nuclease, a transcription activator-like (TAL) effector nuclease, and Cpf1.

Also provided in the invention are feline somatic cells, feline embryonic stem cells, and feline iPS cells, which are heterozygous or homozygous for a disruption in Fel d I locus sequences or flanking sequences thereof. For example, the disruption can be a knock-out as described herein. The disruption of the cells can include deletion or mutation of: (a) the promoter shared by Chain 1 and Chain 2 of the Fel d I locus; (b) exon 1 of Chain 1 of the Fel d I locus; (c) exon 2 of Chain 1 of the Fel d I locus; (d) exon 3 of Chain 1 of the Fel d I locus; (e) exon 1 of Chain 2 of the Fel d I locus; (f) exon 2 of Chain 2 of the Fel d I locus; (g) exon 3 of Chain 2 of the Fel d I locus; or (h) combinations or portions thereof. The combinations can be selected from deletion or mutation of (a) and (b); (a), (b), and (c); (a), (b), (c), and (d); (a) and (e); (a), (e), and (f); (a), (e), (f), and (g); (a), (b), and (e); (a), (b), (c), and (e); (a), (b), (e), and (f); (a), (b), (c), (e), and (f); and (a), (b), (c), (d), (e), and (f); (a), (b), (e), (f), and (g); (a), (b), (c), (e), (f), and (g); (b) and (c); (b), (c), and (d); (c) and (d); (e) and (f); (e), (f), and (g); (f) and (g); or (a)-(g), or portions thereof.

In other embodiments, the disruption is due to a frameshift mutation which results in the generation of a non-sense mRNA and/or protein from the gene in which the frameshift mutation is present.

In various embodiments, the cells do not contain any integrated heterologous DNA that was used for the disruption.

The invention also provides feline embryos, kittens, and adult cats including cells that are heterozygous or homozygous for a disruption of Fel d I locus sequences or flanking sequences thereof. The disruption can be a knock-out as described herein. In various examples, the disruption in the feline embryo, kitten, or adult cat includes a deletion or mutation of: (a) the promoter shared by Chain 1 and Chain 2 of the Fel d I locus; (b) exon 1 of Chain 1 of the Fel d I locus; (c) exon 2 of Chain 1 of the Fel d I locus; (d) exon 3 of Chain 1 of the Fel d I locus; (e) exon 1 of Chain 2 of the Fel d I locus; (f) exon 2 of Chain 2 of the Fel d I locus; (g) exon 3 of Chain 2 of the Fel d I locus; or (h) combinations or portions thereof. Further, The combinations can be selected from deletion or mutation of (a) and (b); (a), (b), and (c); (a), (b), (c), and (d); (a) and (e); (a), (e), and (f); (a), (e), (f), and (g); (a), (b), and (e); (a), (b), (c), and (e); (a), (b), (e), (f); (a), (b), (e), and (f); (a), (b), (c), (e), and (f); and (a), (b), (c), (d), (e), and (f); (a), (b), (e), (f), and (g); (a), (b), (c), (e), (f), and (g); (b) and (c); (b), (c), and (d); (c) and (d); (e) and (f); (e), (f), and (g); (f) and (g); or (a)-(g), or portions thereof.

In various embodiments, in the feline embryos, kittens, or adult cats, the disruption is due to a frameshift mutation which results in the generation of a non-sense mRNA and/or protein from the gene in which the frameshift mutation is present.

In further embodiments, the feline embryos, kittens, or adult cats do not contain any integrated heterologous DNA that was used for the disruption.

In additional embodiments, all of the cells of the feline embryos, kittens, or adult cats, including germ cells, include the disruption.

The invention provides several advantages. For example, when in the presence of cats of the invention, as compared to conventional cats, cat allergy sufferers will have a decrease (e.g., a decrease of about 50%, 75%, 85%, 90%, 95%, 99%, or 100%) in one or more symptoms of cat allergy. Thus, the cat allergy sufferers may have a decrease in one or more of rhinorrhea, facial pain, sneezing, swollen eyes, itchy throats, breathing difficulties, and serum IgE antibody response against Fel d I (e.g., a decrease of about 50%, 75%, 85%, 90%, 95%, 99%, or 100%). Both heterozygous and homozygous cats are beneficial in regard to reducing the response of a person with cat allergy, although a homozygous knock-out may be preferred. Other features and advantages of the invention will be apparent from the following detailed description, the drawings, and the claims.

BRIEF DESCRIPTION OF THE DRAWINGS

FIG. 26 is the genomic sequencing of Chain 2 of the male kitten demonstrating a one nucleotide insertion, which results in a frameshift mutation.

FIG. 32 is a picture of a gel that demonstrates deletion of the entire intervening sequence of the Fel d I locus between the two DSB's introduced in chain 1 and chain 2 of the Fel d I locus, as confirmed by PCR and gene sequencing.

FIG. 33 shows the genetic sequence alignment derived from the first PCR product from the cell line targeted with one of the TALEN pairs.

DETAILED DESCRIPTION OF THE INVENTION

Derivation and Characterization of Targeted Cell Lines

Pluripotency and the ability to undergo prolonged proliferation are key considerations when choosing and deriving cell lines to be used in gene editing. There are various types of cells that can maintain these characteristics. Some of these cell lines occur naturally, such as embryos and embryonic stem cells; and others are induced from differentiated somatic cells, such as fibroblasts, through the introduction of DNA, RNA and other chemicals that de-regulate the normal cell cycle leading to prolonged proliferation. This invention considers, in one example, methods to derive pluripotent feline embryonic stem cells from the inner cell mass of cat blastocysts. It also considers methods to derive pluripotent stem cells from somatic cells that have been induced into pluripotent cells (iPS cells) through the introduction of specific DNA and/or RNA encoding transcription factors that convert adult cells into pluripotent stem cells. IPS cell formation can also be promoted or induced from somatic cell lines through the introduction of certain proteins and chemicals such as those described by Melton et al and Ding et al in 2008 and 2013[vi,vii].

Figure 1:
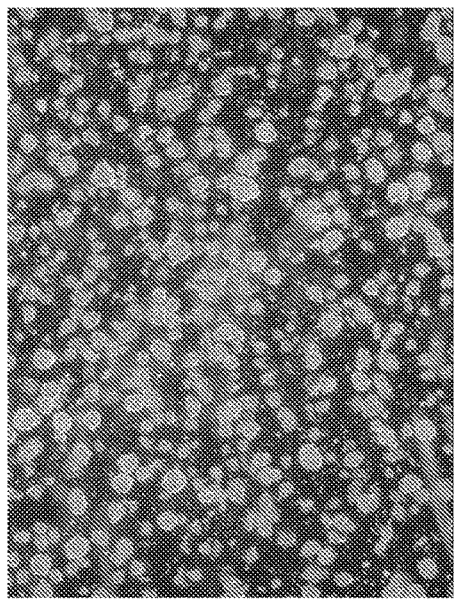
FIG. 1 depicts in vitro hatching of an IVM/IVF cat blastocyst from which is derive a feline embryonic stem cell line.
Figure 2:
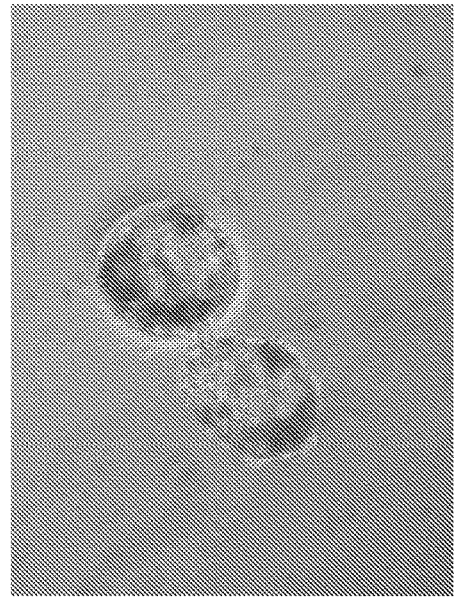
FIG. 2 shows expression of the transcription factors Oct4 and Nanog in undifferentiated feline embryonic stem cells.
Figure 3:
FIG. 3 shows robust teratomas formed from feline stem cells within 2 months of injection in immuno-compromised mice, thus demonstrating retention of pluripotency after genetic manipulation.

One method to produce feline embryonic stem cells is to begin by collecting gametes from ovaries and testes obtained from a neutering clinic. In vitro maturation and in vitro fertilization of cat oocytes were performed to generate cat blastocysts from which to isolate the inner cell mass (FIG. 1). These cat embryonic cells are propagated extensively in an undifferentiated state, while maintaining a stable karyotype. These cells express transcription factors, such as Oct4 and Nanog (FIG. 2), whose function in maintaining pluripotency is conserved in mouse and human Embryonic Stem cells. These cells maintain the ability, after extended culture, to spontaneously differentiate into multiple tissue types in vitro by forming cystic embryoid bodies, as well as in vivo by forming teratomas after grafting into immuno-compromised mice (FIG. 3).

The feline embryonic stem cell lines are maintained in culture conditions that allow them to divide well beyond 15, 20, or 25 passages. One key discovery to support the isolation of stable pluripotent feline ES cells is their independence from Leukemia Inhibitory Factor (LIF) or other cytokines of the Interleukin-6 superfamily to maintain pluripotency. Prior attempts to establish feline ES cell lines have relied upon inclusion of LIF (Yu et al. 2009)[viii]. Rather, explants from cat blastocysts grown on inactivated Mouse Embryonic Fibroblasts (MEFs) in the presence of bFGF with or without an agonist of the TGFβ superfamily including but not limited to Activin, Nodal, TGFβ1, or TGFβ3 can generate stable feline ES cell lines. Once the cell line is established, the cells are easily grown and then dissociated using Accutase in one embodiment, or alternatively collagenase or Dispase, into single cells for gene editing and nuclear transfer. Prior attempts to derive, culture and passage feline ES-like cells derived lines that proliferated slowly and could not be propagated beyond passage 12 without undergoing spontaneous differentiation (Gomez et al. 2009)[ix]. The inability to form stable cell lines may have been due to the inclusion of LIF and or the enzymatic disruption of colonies with Trypsin/EDTA.

Figure 4:
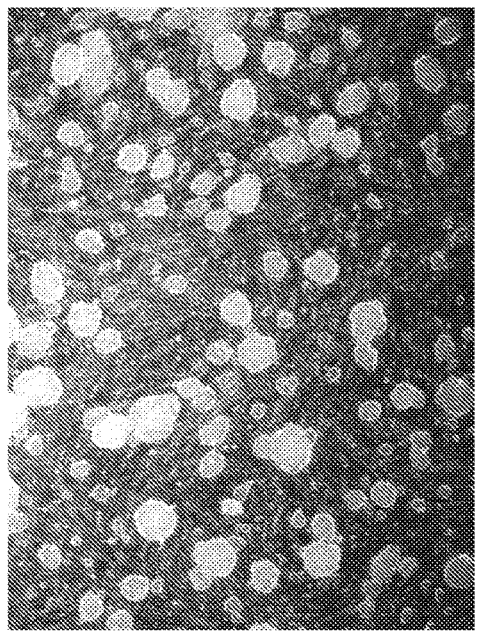
FIG. 4 shows a feline embryonic stem cell line at the appropriate density for transfection or splitting.

The feline ES cells derived by the current methods divide rapidly and grow similar to mouse ES cells in that a single feline ES cell will give rise to a large spheroid colony requiring passaging every 3 days. In brief, feline ES cells can be grown in a range of commercially available media such as DMEM with 15% Fetal Calf Serum or Knockout DMEM (Life Technologies) with 15% Knock-out Serum Replacement (Life Technologies), but unlike mouse ES cells are supplemented with 10 ng/ml of bFGF not LIF. The inclusion of bFGF in media to derive and propagate mouse ES cells would normally induce differentiation. Feline ES cell grow well on a substrate of mitotically inactivated MEFs or an extracellular matrix, such as but not limited to Matrigel, laminins or Vitronectin proteins. Unlike mouse ES cells that can be successfully passaged with trypsin, trypsin even at low concentrations (0.05%) induces death and differentiation of the feline ES cells. Instead, Feline ES rapidly are enzymatically dissociated with Accutase or Collagenase into single cells and split onto new MEF feeders every 3-4 days. A picture a of a late passage culture of feline embryonic stem cells where the colonies are at an appropriate size and density for splitting is shown in FIG. 4.

Under these conditions, the pluripotent feline embryonic stem cell lines survive single cell dissociation and manipulation, grow exponentially, and are truly clonogenic. One cell gives rise to one macroscopic spheroid colony of over 1000 thousand cells, enabling gene editing, physical isolation, and expansion.

Figure 5:
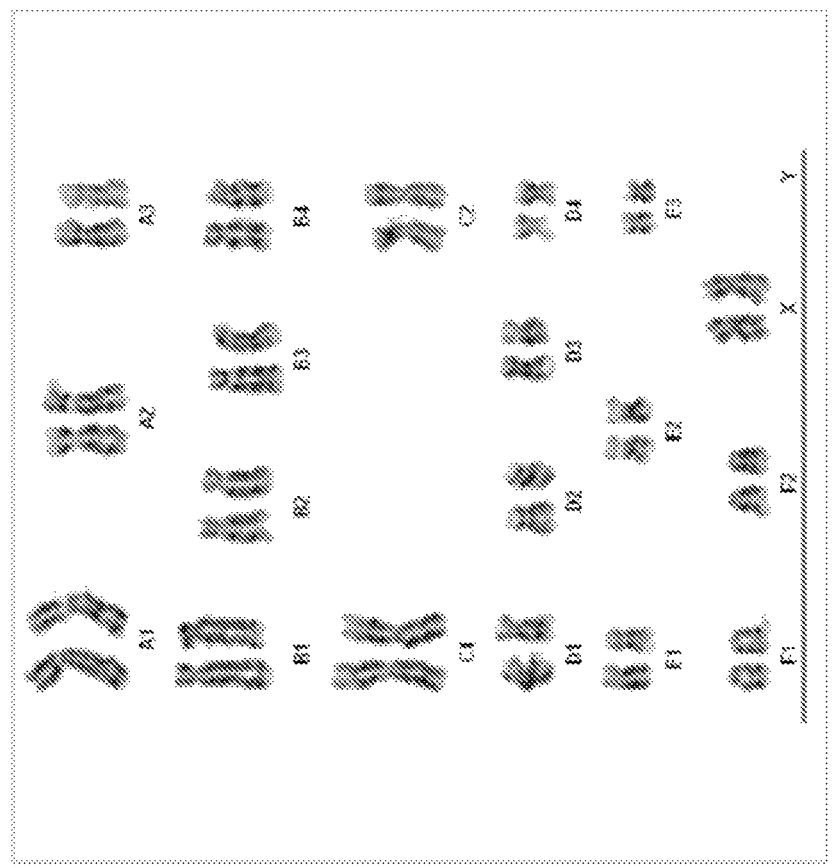
FIG. 5 demonstrates the normal diploid 38XX karyotype of a feline embryonic stem cell line derived from an in vitro fertilized cat embryo.

Following derivation and expansion of the embryonic stem cell line, vials of cells at passage 8 are frozen for use in gene editing and for karyotyping. A normal diploid 38XX karyotype of an embryonic stem cell line at passage eight is shown in FIG. 5.

Further, those familiar with mammalian cell culture can readily derive and culture embryonic and adult fibroblasts and other somatic cell lines derived from cats.[x] Multiple feline embryonic fibroblast lines can be isolated from cat fetuses obtained during a range of developmental stages from 14.5 days post coitus up until birth and used to target the Fel D I locus. In addition, dermal fibroblast lines can readily be established from skin biopsies from post-natal cats and used to directly target the Fel D I locus. Bulk cultures of fibroblasts from both sources are transfected with gene-editing tools to knock-out the FelD I locus and single cells are clonally isolated for expansion.

In addition, feline fetal and adult fibroblasts can be readily reprogrammed using exogenous mouse, feline, human or other mammalian transcription factors delivered using a variety of established methods. Feline induced pluripotent stem cell lines can be readily generated using retroviral, lentiviral, Sendai viral vectors, plasmid DNA or mini-circle DNA as well as mRNAs encoding 4 or more transcription factors; e.g., Oct4, Sox2, cMyc, and a KLF family member (e.g., Klf4) with or without Lin28. Alternatively, Oct4, or Oct4 and Sox2, in combination with a KLF family member (e.g., Klf4), can be used. Conservation of amino acid identity between the feline and mouse or human transcription factors is sufficient to support the introduction of exogenous heterospecific transcription factors to impart the epigenetic changes and transcriptional reactivation of the feline endogenous genes required to reset and maintain pluripotency in feline iPSCs.

Furthermore, cells can be incompletely reprogrammed. In particular, during reprogramming, many somatic cells will proliferate under the influence of exogenous transcription factors, but do not turn on their own endogenous genes required to maintain pluripotency independent of the ectopic factors. Upon removal of the exogenous factors (by silencing, ejection or inactivation of the vector or plasmid DNA;

or by ceasing transfection of mRNA or protein), many somatic cells will revert to their fibroblastic shape and growth characteristics. Targeting the Fel d I locus and clonal isolation of cell lines can be accomplished in fibroblasts that have been subjected to one or more of the proto-oncogenes described herein without achieving a stable, pluripotent state. These transiently transfected/transduced cells, which is neither somatic nor pluripotent, can also be used in the invention. These cells can optionally be maintained in an incompletely reprogrammed state for, e.g., at least 5, 10, 15, 20, or 25 passages.

Figure 6:
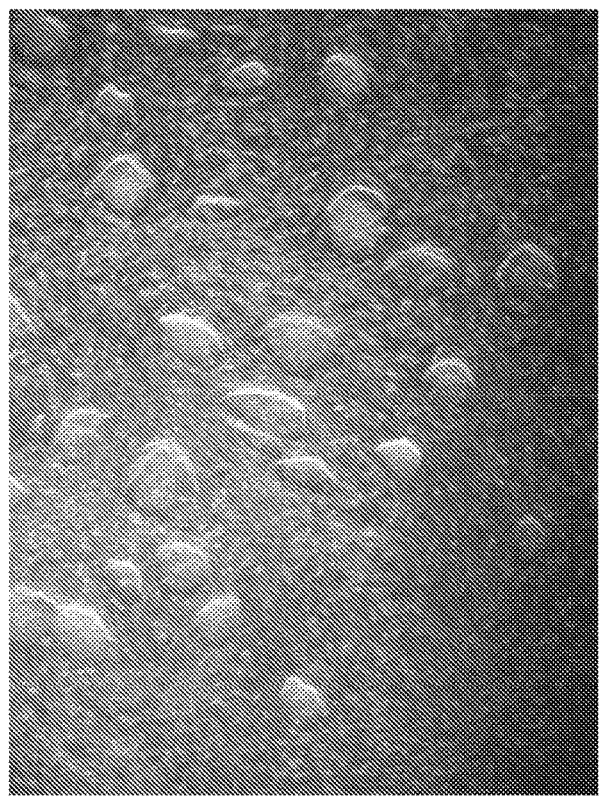
FIG. 6 depicts primary feline iPS cell colonies arising from female adult cat dermal fibroblasts two weeks after transduction with retroviral vectors.
Figure 7:
FIG. 7 demonstrates the expansion of a clonal feline iPSC line in culture conditions supportive of feline ES cells.
Figure 8:
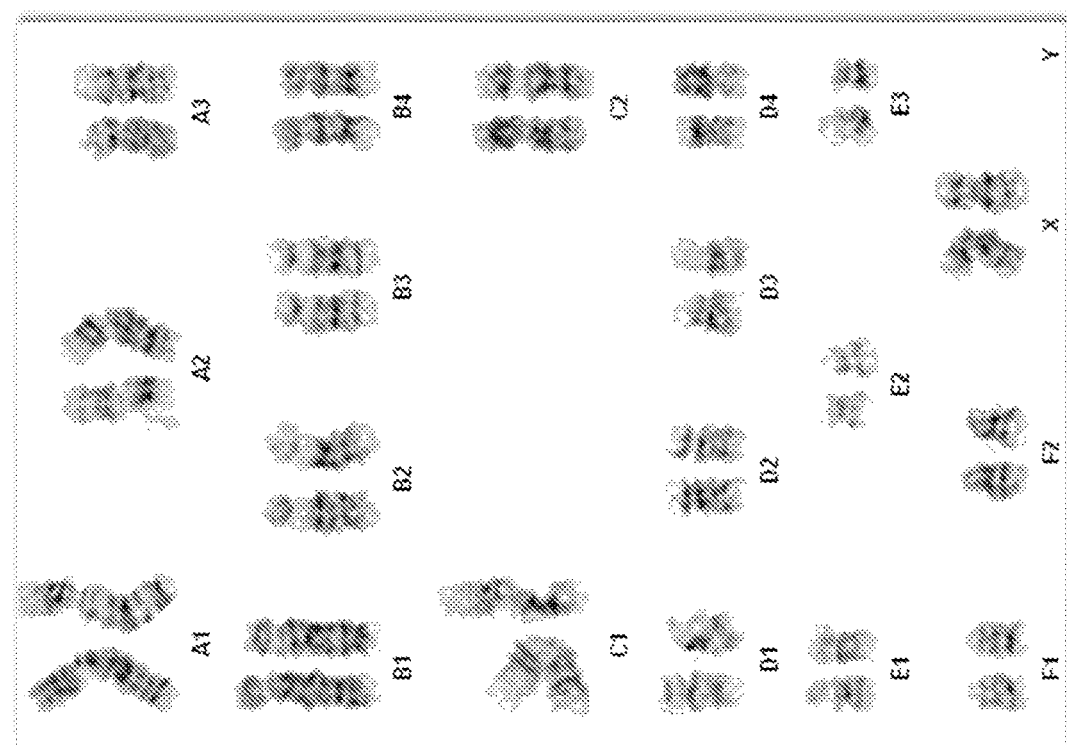
FIG. 8 demonstrates a normal diploid feline iPS cell line (2n=38) cat karyotype by Giemsa banding. The stable, iPS feline cells are used for gene targeting, selection, isolation and expansion to yield a nuclear donor with a defined genotype at the Fel d I locus.

Transduction with VSVG-pseudotyped retroviral vectors expressing the human Oct4, Sox2, Klf4 and c-Myc cDNAs is sufficient to reprogram both fetal and adult feline fibroblasts into cat iPS lines. When grown under conditions required to maintain undifferentiated feline embryonic stem (ES) cells described above, primary spheroid colonies form within 14 to 16 days after retroviral transduction (FIG. 6). These colonies survive similar enzymatic disruption with Accutase as used to passage feline ES cells, and single feline iPSCs give rise to stable clonal lines that maintain an undifferentiated morphology in conditions developed to support feline ES cells (FIG. 7). These feline iPS cell lines grow rapidly and can be cultured for over 15 passages, well beyond the point at which the parental dermal fibroblasts undergo senescence. The feline iPS cell line maintains a normal diploid (2n=38) cat karyotype by Giemsa banding (FIG. 8). These stable, iPS feline cells can subsequently be used for gene targeting, selection, isolation and expansion to yield a nuclear donor with a defined genotype at the Fel d I locus.

Alternatively, the same transcription factors can be delivered using lentiviral vectors to deliver singly or in combination the same transcription factors.

In addition, non-integrating reprogramming can be accomplished using Sendai viral vectors, plasmid DNA systems, In Vitro Transcribed mRNAs, or recombinant proteins. Delivery of the mouse, feline or human genes or gene products by the methods above could be used to successfully generate feline iPSCs from fetal or adult somatic cells in the same culture conditions established to derive and propagate feline ES cells, as demonstrated using retroviral vectors.

In various embodiments, the invention includes the cells described herein (e.g., feline embryonic stem cells, feline iPS cells, feline single-cell embryos, and feline somatic cells) that are in isolated or purified form. Also included in the invention are these cells comprising one or more components of a gene editing tool, such as those described herein (e.g., an exogenously added, heterologous zinc finger nuclease, TAL effector nuclease, guide RNA for use in the CRISPR-Cas9 method, Cas9 protein, and/or Cas9 nucleic acid molecule sequences; also see below) and these cells having one or more of the gene disruptions described herein. The invention further includes compositions comprising feline embryonic stem cells or feline iPS cells present in a growth medium characterized by one or more of the following features: (i) the absence of a cytokine of the interleukin-6 family, such as LIF; (ii) the presence of bFGF and, optionally, one or more agonist of the TGF-beta superfamily such as, activing, nodal, TGFb1 and/or TGFb3; (iii) the absence of homologous inactivated feline embryonic fibroblast layers, and (iv) the presence of mitotically inactivated mouse embryonic fibroblasts (MEFs) or an extracellular matrix, such as matrigel or laminin.

Engineered Sequence-Specific DNA-Binding Modules Fused with Targeted Nucleases

This invention describes the use of engineered, sequence-specific DNA-binding modules fused with targeted nucleases to create hypo-allergenic animals by creating null mutations of identified allergens, and specifically using this technology to create hypo-allergenic cats by knocking out the major cat allergen, Fel d I. While this invention describes the use of three popular gene-editing tools used to create Fel d I "knock-outs", these are provided as way of example. It is recognized that the field is rapidly expanding and that there will certainly be other advances and variations in gene editing tools and protocols that will be used to facilitate genetic engineering.

One of the gene editing tools used to create Fel d I "knock-outs" in cell lines, embryos, and cats is zinc fingers nucleases (ZFNs). ZFNs are fusion proteins comprising an array of site-specific DNA-binding domains attached to the endonuclease domain of the bacterial FokI restriction enzyme. Each zinc finger domain recognizes a 3- to 4-bp DNA sequence, and tandem domains bind to an extended nucleotide sequence (typically with a length that is a multiple of 3, usually 9 bp to 18 bp) that is unique within a cell's genome.

Figure 9:
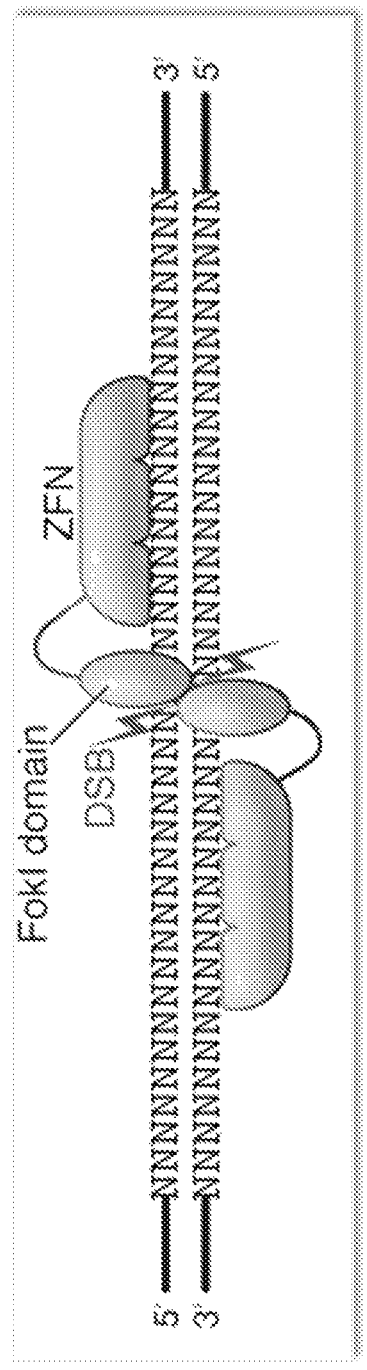
FIG. 9 illustrates how the variable length ZFN DNA-binding domains bind to flanking DNA sequences and position their FokI nuclease domains such that they dimerize and generate a DSB between the binding sites.

To cleave a specific site in the genome and specifically the Fel d I gene, ZFNs are designed as a pair that recognizes two sequences flanking the site, one on the forward strand and the other on the reverse strand. Open-source libraries of zinc finger components and protocols are available to identify ZFNs that bind with high affinity to the desired sequence[xi,xii,iii,xiv,xv,xvi,xvii]. Upon binding of the ZFNs on either side of the site, the pair of FokI domains dimerize and cleave the DNA at the site, generating a double-strand break (DSB) with 5' overhangs[xviii] (FIG. 9).

Figure 10:
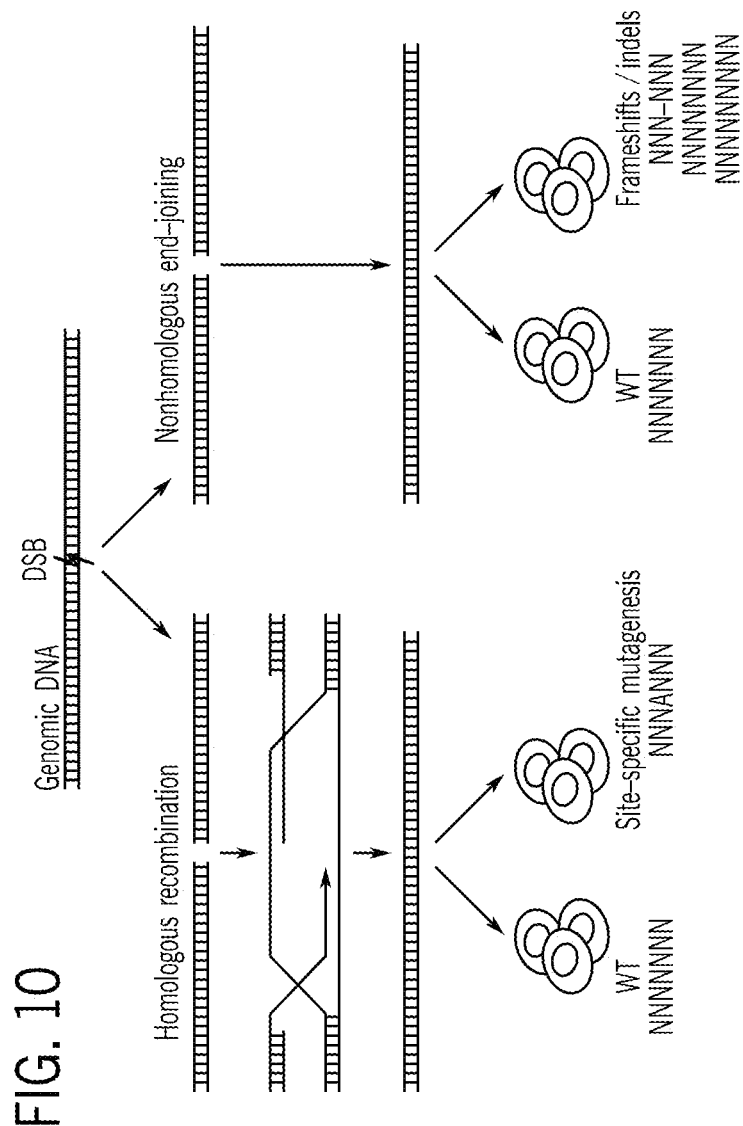
FIG. 10 depicts two repair processes that can occur after an induced double stranded break with FokI in the Fel d I locus. The figure also illustrates how an exogenous oligonucleotide sequence can be introduced to achieve site-specific mutagenesis if desired.

Cells repair DSBs using either (a) nonhomologous end joining (NHEJ), which can occur during any phase of the cell cycle, but occasionally results in erroneous repair, or (b) homology-directed repair (HDR), which typically occurs during late S phase or $G_2$ phase when a sister chromatid or engineered vector is available to serve as a repair template (FIG. 10).

Figure 11:
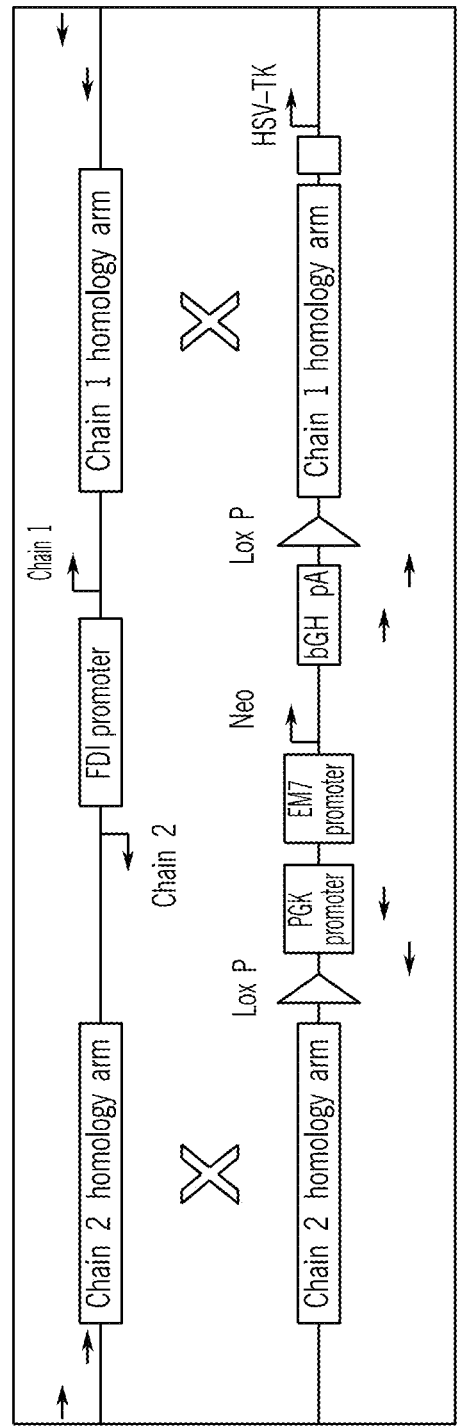
FIG. 11 illustrates how homologous recombination using an exogenous DNA vector as a repair template is used to introduce a selection marker into the disrupted Fel d I locus. After successful screening for the desired mutation, the selection marker is removed at the Lox P sites.

The error-prone nature of NHEJ is exploited to introduce frameshifts into the coding sequence of the Fel d I locus, the promoter region, and/or the sequence flanking the locus (from here on labeled homology arms), resulting in premature truncation of the coding sequence or nonsense-mediated decay of the mRNA transcript. Alternatively, HDR is utilized to insert a specific mutation, with the introduction of a repair template containing the desired mutation flanked by homology arms (Nucleic Acid Sequence and Homologous Recombination Vectors for Disruption of a Fel D I Gene, US 2012/8,119,785 B2, which is incorporated herein by reference)[xix]. In response to a DSB in DNA, HDR utilizes another closely matching DNA sequence to repair the break. Mechanistically, HDR can proceed in the same fashion as traditional homologous recombination, using an exogenous double-stranded DNA vector as a repair template[xx]. It can also use an exogenous single-stranded DNA oligonucleotide (ssODN) as a repair template. For ssODNs, homology arms of as little as 20 bp can enable introduction of mutations into the genome[xi,xxii,xxiii]. Selection markers such as antibiotic resistance, antibiotic sensitivity, or a visual marker such as green fluorescent protein (GFP) are introduced in this manner to aid in the selection of correctly targeted gene. When selection markers are used, then extra steps can be taken to remove the selection marker cassette from the genome using systems such as Cre-lox and Flp-FRT (FIG. 11).

When selection markers are not used, then extra steps to remove the selection marker cassette from the genome using systems such as Cre-lox and Flp-FRT are unnecessary[xxiv,xxv].

In order to minimize off-target events, ZFNs are created in pairs. Each pair of ZFNs is engineered to have distinct FokI domains that are obligate heterodimers[xx,xi,xviii]. This prevents a single ZFN from binding to two adjacent off-target sites and generating a DSB; rather, the only way an off-target event could occur is if both ZFNs in a pair bind adjacently and thus allow the FokI dimer to form. Another strategy that has been demonstrated to reduce off-target events is the introduction of purified ZFN proteins into cells[xxix]. The use of multiple ZFNs also allows for the precise deletion of a genomic region.

Another gene-editing tool used to create a Fel d I null mutation in cell lines, embryos, and cats makes use of a class of proteins known as Transcription activator-like effectors (TALEs). Naturally occurring TALE repeats comprise tandem arrays with 10 to 30 repeats that bind and recognize extended DNA sequences[xxx]. Each repeat is 33 to 35 amino acids in length, with two adjacent amino acids (termed the repeat-variable di-residue [RVD]) conferring specificity for one of the four DNA base pairs[xxxi,xxxii,xxxiii,xxxiv,xxxv]. Thus, there is a one-to-one correspondence between the repeats and the base pairs in the target DNA sequences. The single base recognition of TALE-DNA binding repeats affords greater design flexibility than triplet-confined zinc-finger proteins, since not all nucleotide triplets have their corresponding zinc fingers elucidated. TALEs do not show context effects on the specificities of individual fingers in the array, a current limitation of some gene-editing technologies such as ZFNs.

Figure 12:
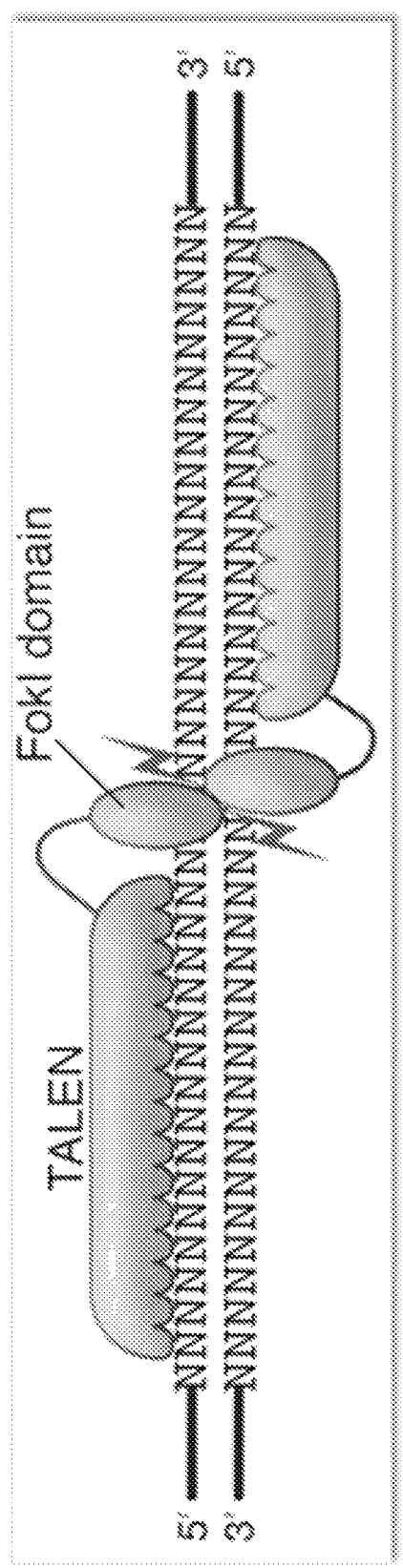
FIG. 12 illustrates the one-to-one correspondence between the repeats and the base pairs in the target DNA sequences and the heterodimeric binding of TALENS to DNA regions of variable length to generate DSB in the Fel d I locus with FokI between binding sites.

Elucidation of the RVD code makes it possible to create an engineered site-specific nuclease that fuses a domain of TALE repeats to the FokI endonuclease domain, termed TAL effector nucleases (TALENs)[xxxvi,xxxvii,xxxviii]. TALENs can efficiently generate DSBs at a desired target site in the genome and so can be used to "knock-out" genes or "knock-in" mutations (FIG. 12).

The RVD code is employed to engineer many TALE repeat arrays that bind with high affinity to desired genomic DNA sequences and in this case to the desired Fel d I genomic sequence. The engineered TALE repeat arrays bind to desired DNA sequences with affinity rates as high as 96%[17,xxix]. TALE repeat arrays are easily extended to whatever length is desired. TALENs are often built to bind 18-bp sequences or even longer.

Sites of DSBs created by TALENs are exploited to introduce frameshift mutations into the coding sequence of the Fel d I locus, the promoter region, and/or sequences flanking the locus, resulting in a Fel d I "knock-out." When multiple DNA site-specific TALEN pairs are introduced simultaneously, longer regions of the Fel d I coding sequences are deleted resulting in a null mutation (see Example 1 below for further details).

Further, a specific mutation can be inserted during the repair process following cutting with TALENs. This is accomplished by introducing a repair template containing the desired mutation, such as a selection marker, flanked by homology arms. In response to the TALEN induced DSB in DNA, HDR utilizes the closely matching DNA sequence to repair the break. Mechanistically, HDR can proceed in the same fashion as traditional homologous recombination, using the exogenous double-stranded DNA vector as a repair template. Selection markers such as antibiotic resistance, antibiotic sensitivity, or a visual marker such as green fluorescent protein (GFP) are introduced in this manner to aid in the selection of correctly targeted gene. When selection markers are used, then extra steps can be taken to remove the selection marker cassette from the genome using systems such as Cre-lox and Flp-FRT. When selection markers are not used, then extra steps to remove the selection marker cassette from the genome using systems such as Cre-lox and Flp-FRT are unnecessary.

The newest set of genome-editing tools used to create Fel d I "knock-outs" in cell lines, embryos, and cats is the CRISPR-Cas9 system. Clustered regularly interspaced short palindromic repeats (CRISPR) and the CRISPR-associated (Cas9) system use a combination of proteins and short RNAs to target specific DNA sequences for cleavage. Engineered DNA "protospacers" are used to express short guide RNAs, which are then used by a CRISPR-Cas9 system to target and cut specific DNA sequences. Because the specificity of the CRISPR-Cas9 is conferred by a simple guide RNA, and no protein engineering of a custom nuclease is necessary to target a specific site, the CRISPR-Cas9 system is extremely versatile and has rapidly become a preferred choice for genome editing.

Figure 13:
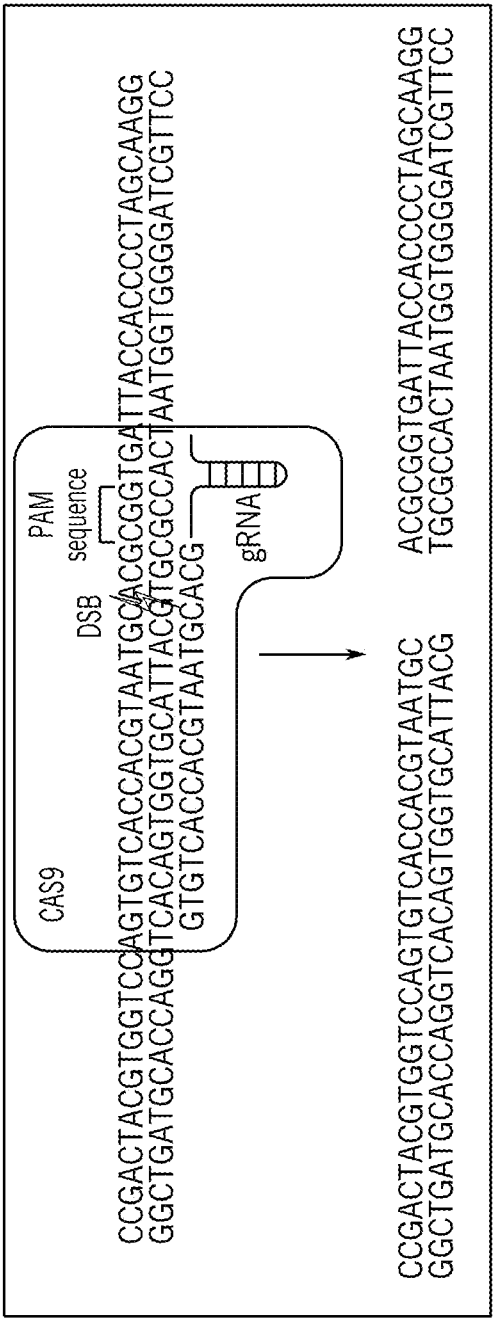
FIG. 13 illustrates the use of the CRISPR-Cas9 system in which a guide RNA recognizes and hybridizes a 20-bp protospacer in the genome. The desired DSB in the Fel d I locus occurs at a site 3-bp upstream of the PAM sequence.

The heterologous expression of a CRISPR-Cas system, comprising the Cas9 protein along with guide RNA(s) in mammalian cells results in DSBs at target sites with (a) a 20-bp sequence matching the protospacer of the guide RNA and (b) an adjacent downstream NGG nucleotide sequence (termed the protospacer-adjacent motif [PAM])[xl,xli,xlii,xliii]. This occurs via the formation of a ternary complex in which Cas9 binds to the PAM in the DNA, then binds the nonprotospacer portion of the guide RNA, upon which the protospacer of the guide RNA hybridizes with one strand of the genomic DNA. Cas9 then catalyzes the DSB in the DNA at a position 3 bp upstream of the PAM[44] (FIG. 13).

Figure 14:
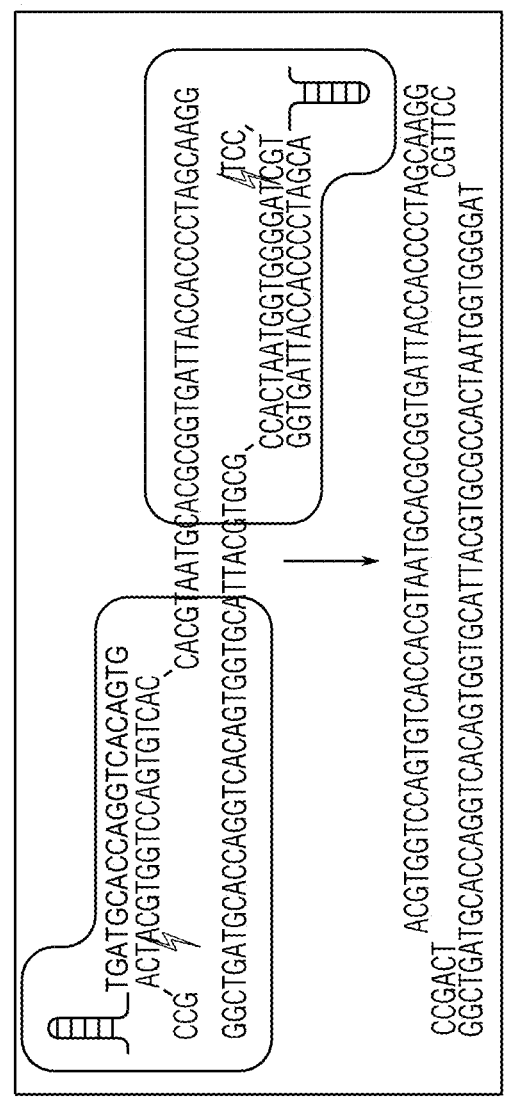
FIG. 14 illustrates how "Nickase" CRISPR-Cas9 is used to bind to flanking DNA sequences in the Fel d I locus and generate single-strand nicks that are the equivalent of a DSB.

In another variation, the "nickase" CRISPR-Cas9 binds to flanking DNA sequences. and generates single-strand nicks that are the equivalent of a DSB (FIG. 14). To reduce off-site targeting, use of a pair of "nickase" CRISPR-Cas9 complexes with binding sites on opposite strands flanking the target site can produce the equivalent of a DSB with 5' overhangs (FIG. 14), which is then repaired by NHEJ or HDR and can result in an on-target alteration. At an off-target site, a single-strand nick would be fixed by a different mechanism (base excision repair pathway) that is much less likely to result in a mutation. Because the likelihood of two nickases binding near each other elsewhere in the genome is very low, the off-target mutation rate are dramatically reduced. Another strategy to reduce off-target effects is to reduce the length of the protospacer portion of the guide RNA, which makes it less tolerant of mismatches and thus can preserve the on-target efficacy while reducing off-target mutagenesis[xliv].

Figure 15:
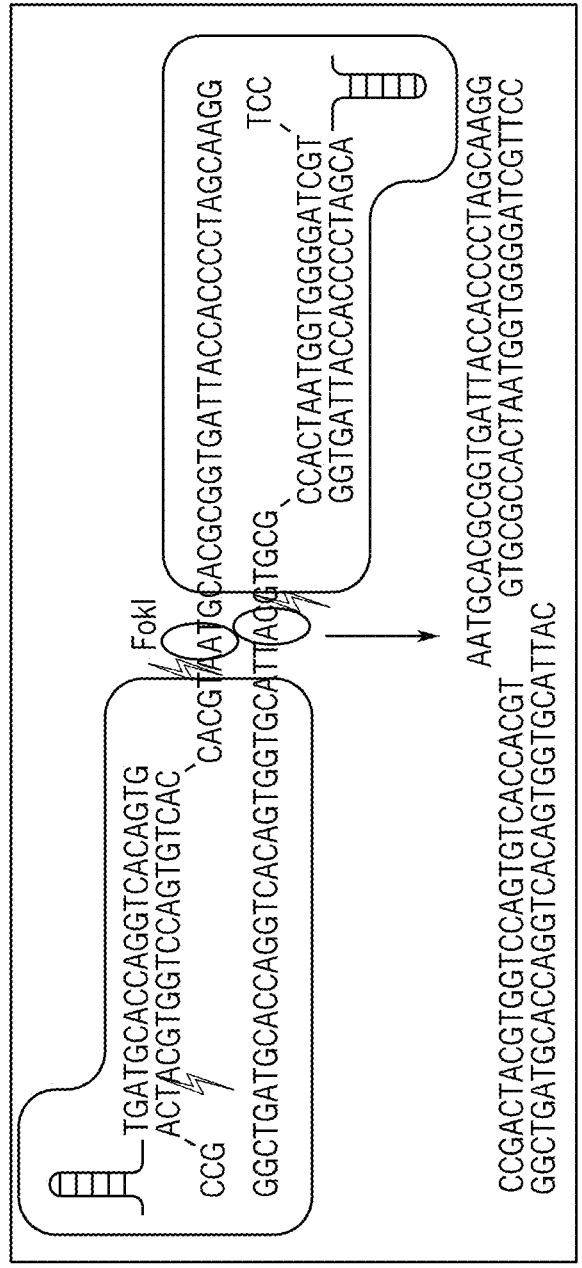
FIG. 15 illustrates how fusion proteins of catalytically dead CRISPR-Cas9 and FokI nuclease domains bind to flanking DNA sequences in the Fel d I locus and position their FokI domains such that they dimerize and generate a DSB between binding sites.

A third successful strategy is to use a pair of fusion proteins comprising catalytically dead CRISPR-Cas9 (that cannot cut DNA) fused to a FokI nuclease. The guide RNA directs the fusion proteins to flanking DNA sequences. The FokI domains are positioned such that they dimerize and generate DSB between binding sites[xlv,xlvi] (FIG. 15). These fusion proteins combine the most desirable properties of CRISPR-Cas9, TALENs and ZFNs.

CRISPR-Cas9 is engineered to target the Fel d I locus or any other genomic sequence by changing the 20-bp protospacer of the guide RNA, which can be accomplished by subcloning this nucleotide sequence into the guide RNA plasmid backbone. The Cas9 protein component remains unchanged. The ease of use of CRISPR-Cas9 allows for the generations of a large set of vectors to target numerous sites.[46] This is useful when targeting multiple allergens in an animal, such as Can f 1 and Can f 2 in canines. In practice, multiple guide RNAs can be used in parallel to target multiple sites simultaneously in the same cell[46xlvii] This makes it straightforward to mutate multiple genes at once or to engineer precise deletions in a genomic region.

As with some other gene editing technologies, sites of DSBs created by the CRISPR-Cas9 system are exploited to introduce frameshift mutations into the coding sequence of the Fel d I locus, the promoter region, and/or the homology arms flanking the locus, resulting in a Fel d I "knock-out." When multiple CRISPR-Cas9 pairs are introduced simultaneously, longer regions of the Fel d I coding sequences are deleted resulting in a null mutation (see Example 2 below for further details).

As with other gene editing tools inducing DSBs, vectors and other mutations can be inserted during the repair process following cutting with CRISPR-Cas9. This is accomplished by introducing a repair template containing the desired mutation, such as a selection marker, flanked by homology arms. In response to the CRISPR-Cas9 induced DSB in DNA, HDR utilizes the closely matching DNA sequence to repair the break. Mechanistically, HDR can proceed in the same fashion as traditional homologous recombination, using the exogenous double-stranded DNA vector as a repair template. Selection markers such as antibiotic resistance, antibiotic sensitivity, or a visual marker such as green fluorescent protein (GFP) are introduced in this manner to aid in the selection of correctly targeted gene. When selection markers are used, then extra steps can be taken to remove the selection marker cassette from the genome using systems such as Cre-lox and Flp-FRT. When selection markers are not used, then extra steps to remove the selection marker cassette from the genome using systems such as Cre-lox and Flp-FRT are unnecessary.

Variants of the CRISPR-Cas9 system have recently been identified, or are currently being characterized. Class 1 effectors utilize multi-protein complexes, whereas class 2 effectors rely on single-component effector proteins such as Cas9. One such variant is Cpf1, a class 2 CRISPR effector that shows nuclease activity but has features distinct from Cas9. It is likely that other endonucleases will be identified that will be of use for targeting specific genome sequences and could be expected to work in targeting the Fel d I locus, and use of these methods is also included in the invention.

Introduction of Gene Editing Tools into Cells

Engineered, sequence-specific DNA-binding modules fused with targeted nucleases can be introduced into cells in multiple forms and by multiple techniques. Common forms of gene-editing tools include plasmids, mRNA, and proteins. Common techniques for introducing gene-editing tools include electroporation, direct microinjection, and chemical transfection with polyethylenimine and commercial reagents such as Lipofectamine 2000. Depending on the form of the gene-editing tool, transfection can take place by multiple methods.

Figure 16:
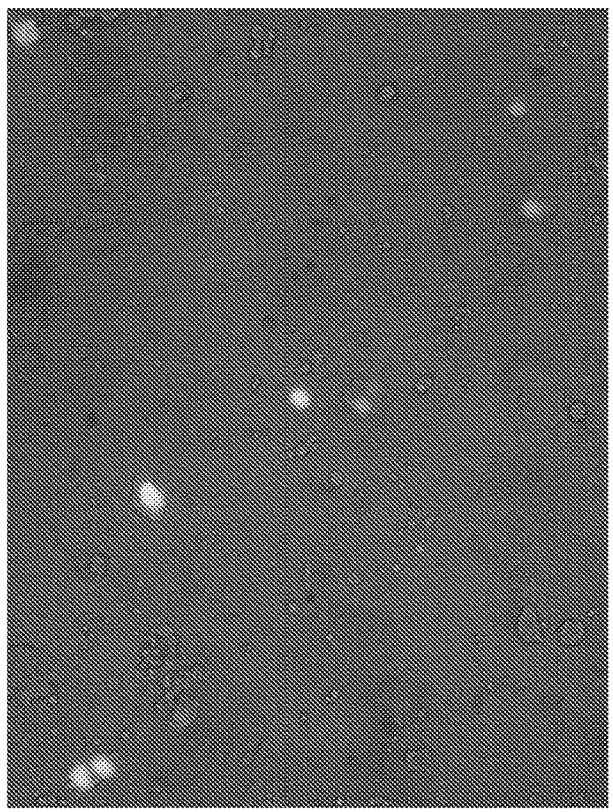
FIG. 16 depicts a parental feline stem cell line and single-cell derived sub-clones isolated after electroporation with a control GFP construct.

Gene editing constructs in the form of DNA or mRNA can readily be introduced into cat adult and fetal fibroblasts, as well as feline ES and iPS cells, using an electroporation device such as the Amaxa Nucleofector. Clonal lines of the feline parental ES line are derived after electroporation with a control GFP plasmid (FIG. 16). These cells form robust teratomas within 2 months of injection in immuno-compromised mice, demonstrating retention of proliferation and differentiation capacity, after genetic manipulation.

In an alternative approach, DNA plasmids encoding gene-editing constructs can be introduced into feline ES, iPS cells or somatic cells such as fibroblasts by transfection using polyethylenimine or a range of readily available transfection reagents such as Lipofectamine 2000 or 3000 (Life Technologies) or DNA-In Stem (MTI-GlobalStem). Both transfection and electroporation introduce the possibility of random integration of exogenous DNA as whole linearized plasmids or fragments into the cat genome. However, clonal lines isolated after electroporation or transfection can be screened for the integration of exogenous DNA to identify and expand cell lines free of artifacts.

In a one embodiment, mRNAs encoding gene-editing constructs for ZFN's, TALENS, or CRISPR/Cas9 and guideRNAs are transiently transfected into feline somatic cells such as fibroblasts, ES cells, or iPS cells. By this method there is no risk of random integration into the cat genome. Cat cells can be efficiently transfected using polyethylenimine or readily available reagents such as RNAiMax (LifeTechnologies) or mRNA-In (MTI-Global Stem).

Isolation and Expansion of Clonal Lines

After introduction of gene-editing constructs, single feline somatic cells such as fibroblasts, ES cells, and, iPS cells are cultured in individual wells to derive clonal lines for subsequent expansion and genetic characterization.

Identification of Correctly Targeted Cells

A variety of molecular techniques are available to identify correctly targeted cells. These molecular identification techniques can be performed in bulk cell cultures, consisting of a mix of targeted and wild type cells. Alternatively, the techniques are applied to monoclonal, isolated cell lines derived from single targeting events. The following describes molecular screening techniques used to identify correctly targeted cells in bulk culture or in monoclonal cell lines as well as techniques used to screen for the presence of the Fel d I protein and evaluate its immunologic effects through direct antigen challenge:

1. Genomic DNA

PCR to detect deletion by size difference: The Fel d I locus is amplified in a PCR reaction with primers on either side of chain 1, chain 2, or including both chains. A deletion of the entire locus, part of each gene, or the shared promoter is detected by identifying size differences in the PCR product when the wild type allele is compared to the targeted allele.

Sequencing to detect deletion or single base pair change: The Fel d I locus, or parts of the locus including Chain 1 coding or regulatory sequence, or Chain 2 regulatory or coding sequence, are PCR amplified. The PCR product is excised from the agarose gel after gel electrophoresis, or purified and used directly for sequencing. Sequencing methods could include Sanger sequencing or Pyrosequencing, Next Gen Sequencing, base pair sequence by mass spectrometry, microarray hybridization, or other hybridization based methods.

The resulting sequence is compared to the ICGSC Felis_catus 6.2/felCat5 assembly of the cat genome or to a wild type control. Sequence changes that would create a hypoallergenic cat are those that reduce the expression of the gene, that change splicing patterns, that remove the start coding, that create a frame shift mutation, that create sequence changes influencing protein folding, that change allergenic epitopes, or that remove the coding sequence of the gene either partially or completely.

Alternatively, quantitative methods can be used to quantify the mutant vs. wild type allele frequency without determining the exact sequence of the mutation. These include real-time PCR methods with either primer or probe sequences specific for the wild type allele, or hybridization methods like Northern or Southern blots.

Another method to identify mutants in a pool of wild type cells uses endonucleases that cut mismatched DNA heteroduplexes. Commonly used endonucleases are Cell or T7 Endonuclease I, but various other brand names are used by manufacturers for unspecified enzymes in these assays. Generally, genomic DNA from target cells is amplified by PCR. The PCR products are denatured and reannealed to allow heteroduplex formation between wild-type DNA and CRISPR/Cas9-mutated DNA. An endonuclease such as T7 Endonuclease 1, which recognizes and cleaves mismatched DNA, is used to digest heteroduplexes. The resulting cleaved and full-length PCR products are visualized by gel or capillary electrophoresis. The ratio of cleaved to full-length products is indicative of the frequency of the mutation vs. wild type sequence.

2. RNA

Messenger RNA from the targeted gene is detected and analyzed. Complete absence of the mRNA for one or both Fel D I genes implies a complete removal of the coding sequence, a frame shift mutation leading to nonsense mediated decay, or a complete lack of expression due to changes in the promoter or other regulatory regions.

Partial reduction in expression levels is indicative of a heterozygous mutation, or a mutation in only a sub population of cells. Quantifying levels of mRNA indicate the frequency of the mutation in the population of cells. mRNA quantity is determined by RT-PCR, either real-time PCR or semi-quantitative end-point PCR, by RNA-seq or other next gen sequencing techniques, or by a variety of hybridization methods including northern blotting or in-situ hybridization methods.

3. Protein

The presence or absence of the Fel d I protein is detected by Western Blot, ELISA or similar immunoassays. In general, an antibody specific to the targeted protein is bound to a detectable compound, which could be a fluorescent dye, a functional tag, or an epitope that can be detected through standard molecular biology methods. Antibodies are commercially available to detect the Fel d I allergen in the above immunoassays, and are tested on targeted cells, the tissues, or excretions such as saliva of a Fel d I "knock-out" cats.

The absence or significant reduction of Fel D I protein reflects removal of the coding sequence, a frame shift mutation leading to nonsense mediated decay, a lack of expression due to changes in the promoter or other regulatory regions, or a mutation reducing translation of the mRNA, for instance a change in the translation start sequence or start codon.

4. Protein Function

The removal or reduction of the Fel d I protein is also detected by the absence of reaction in patients with known cat allergies. Intradermal skin testing using a purified Fel d I allergen is employed as the gold standard to classify patients as having a cat allergy. Histamine-mediated inflammatory reactions against existing Fel d I standards are compared to protein extracts purified from the saliva of Fel d I knockout cats or cells or tissues.

Nuclear Transfer Followed by Implantation into Feline Surrogate Recipient

Once the Fel d I locus has been disrupted or "knocked-out" in the desired cell line, then the nucleus of the modified cell is transferred into an enucleated feline oocyte or one-cell embryo. The genetically modified embryo is allowed to divide in culture and is transferred to a feline surrogate recipient anywhere from the 2-cell stage to the blastocyst stage and allowed to develop to term. The general steps required for nuclear transfer followed by embryo/blastocyst implantation into a pseudopregnant feline surrogate include the following:

(a) Collection of Oocytes

The first step in the nuclear transfer process is to generate unfertilized donor eggs. As with the derivation of feline ES cells, immature cat oocytes are isolated from ovaries and subjected to In Vitro maturation. In addition, In Vivo Matured oocytes can be collected from donor cats that have been super-ovulated by injection of (PMSG and hCG) or through timed ovulations occurring in natural estrus. Typically, oocytes are aspirated from ovarian follicles via laparotomy or laparoscopy just prior to ovulation. These oocyte cumulus complexes are cultured for subsequent nuclear reconstruction. Alternatively, after natural or induced ovulation, a catheter is threaded under the ovarian bursa into the oviduct and the ovulated oocytes are then flushed caudally into the uterus and collected via a second catheter with an inflatable cuff introduced rostral to the uterine bifurcation.

(b) Enucleation of Oocytes

Figure 17:
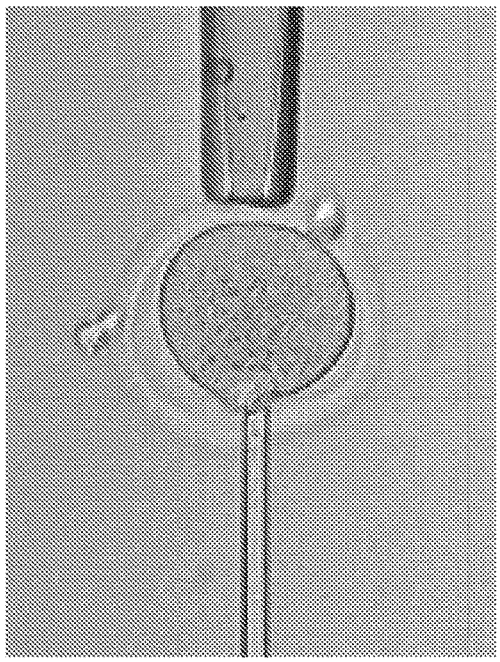
FIG. 17 demonstrates the enucleation of a donor oocyte with a beveled pipette.

Following collection of oocytes, standard techniques are used to remove the nuclei of the unfertilized oocytes. In brief, a suction pipette is used to hold the egg cell steady while a sharp, beveled, glass pipette or piezo drill is used to remove the nucleus of the egg (FIG. 17). The glass needle is pushed through the tough zona pellucida that surrounds the egg cell and the nucleus is gently removed. Enucleation is confirmed by observing the removed spindle. What remains is an "enucleated" egg that still contains protein, RNA molecules, and other important factors in the ooplasm that will help the egg grow and divide once the donor nucleus is inserted and the egg is stimulated to divide.

(c) Nuclear Transfer

Figure 18:
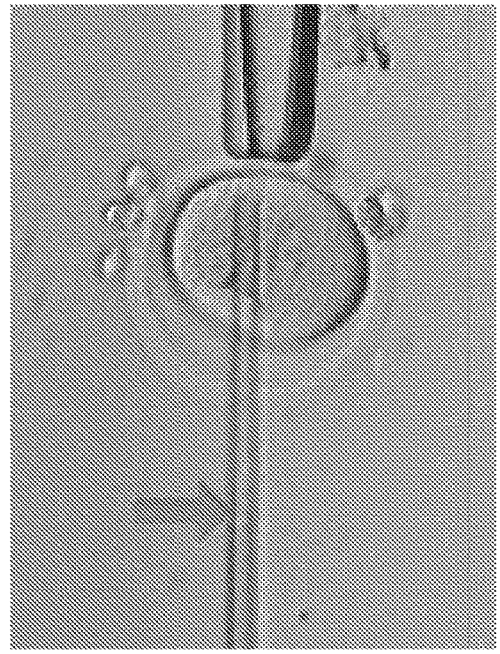
FIG. 18 depicts the tip of a beveled glass needle (see arrow) as it is eased through the zona pellucida and deep into the enucleated egg cell where the donor nucleus is deposited.

Once the nucleus is removed from the oocyte, it is replaced with the nucleus from the donor cell in which the Fel d I gene has been disrupted or removed. In order to do this, the nucleus from the donor cell is injected directly into the enucleated feline oocytes. As with the enucleation process, the tip of a beveled, glass, needle is eased through the zona pellucida and deep into the enucleated egg cell where the donor nucleus is deposited (FIG. 18).

After the nuclear transfer is complete, the unfertilized egg cell is activated using a chemical or electrical treatment that stimulates cellular division. Molecules within the embryonic environment cause the differentiated mature DNA to revert back to embryonic DNA. These cells then begin to divide as though they were a part of a newly developing embryo. The derived oocytes are cultured in vitro overnight to the 2-cell stage, when they can be surgically transferred to the oviducts of a pseudo-pregnant recipient (as described by Swanson 2012)[xlviii], or cultured for several days more until they reach the morulae or blastocyst stage at which time they are transferred into the uterus of a recipient queen.

(d) Preparation of Pseudopregnant Recipient Cats

Feline pseudopregnant surrogate recipients must be prepared to receive the embryos that have undergone nuclear transfer. There are several commonly used methods to prepare queens for embryo transfer. One method is to induce ovulation through timed matings with vasectomized toms (protocols and procedures for performing vasectomies in cats are readily available in standard textbooks of veterinary medicine). Receptors present within the queen's vulva are stimulated during copulation, which results in the release of luteinizing hormone (LH) from the anterior pituitary. The release of LH stimulates ovulation and the maturation of the endometrium of the uterus. Alternatively, a sterile swab or glass rod can be inserted into the vagina to stimulate LH release and ovulation. While natural mating with a vasectomized tom is the preferred method for inducing ovulation, hormone therapy, such as the injection of a GNRH agonist, LH or hCG, can also be used to induce ovulation and the maturation of the uterine lining. Once ovulation has been induced in the pseudopregnant recipient, embryo transfer usually takes place from 3 to 7 days later.

(e) Transfer of Embryos to Pseudopregnant Cats

It is best to transfer cleavage stage embryos and blastocysts to pseudopregnant recipients whose stage of pregnancy is a day or two behind that of the embryos. In normal pregnancy, cleavage stage embryos are found in the oviducts 2.5 to 3 days post ovulation, and pre-implantation blastocysts are found in the uteri of pregnant cats between day 5.5 and 6 post ovulation (Swanson el at. 1994)$^{xlix}$. Therefore, the manipulated embryos are transferred into the oviducts of pseudopregnant recipients 3 to 4 days later or, in the case of blastocysts, to the uteri of pseudopregnant recipients around day 7. This gives embryos time to recover in vivo from the in vitro manipulations. While on average cats give birth to 4 kittens, it is possible to transplant anywhere from 6-15 embryos per uterine horn to account for the decreased viability of IVF and micro-manipulated embryos. The surviving embryos then implant into the uterus, where they are allowed to grow and develop into kittens. Delivery occurs naturally or with surgical assistance.

Direct Embryo Injection Followed by Implantation into Feline Surrogate Recipient We described above a method to create Fel d I "knock-out" cats by performing gene editing in cultured cells, then using these cells for nuclear transfer to create cats with correctly targeted Fel d I loci. Alternatively, gene editing tools which function at high efficiency are injected directly into oocytes or embryos, and these embryos are then implanted into feline surrogate recipients. Healthy kittens born from this procedure can then be screened for successful targeting of the Fel d I locus, using methods described above.

Briefly, ovaries are removed from female cats. Cumulus oocyte complexes (COCs) are extracted from antral follicles using a needle fixed to a disposable syringe. COCs are washed in Hepes buffered Tyrodes Lactate medium containing sodium heparin and are transferred to feline oocyte maturation medium supplemented with various growth factors (Herrick et al., Biol Reprod 2007, 76(5):858-870). After 24 hours, In Vitro Fertilization is performed by adding 20,000 epididymal swim-up sperm per 50 µl culture drop containing containing mature oocytes that have extruded the first polar body. After 18 to 20 h of IVF, cumulus cells and sperm are removed by pipetting in a 0.3 mg/ml hyaluronidase solution. After washing multiple times, fertilized oocytes and one-cell embryos that have extruded the second polar body were selected for experiments.

Fertilized oocytes and one-cell embryos are transferred to a Hepes buffered medium and then subjected to a single 2-pL cytoplasmic injection of nucleases (DNA, mRNA, or protein), guide RNA when required, and an optional marker such as GFP mRNA. Injection success is confirmed by the slight oocyte cytoplasm swelling. The injected embryos are then cultured in the appropriate medium to increase their in vitro development. Cleavage and blastocyst formation are evaluated after 1 and 7 days of culture, respectively. The developing 2-4 cell embryos can be transferred to the oviducts or blastocysts to the uterine horns of pseudopregnant recipient cats to support pregnancy and development to term.

Figure 19:
FIG. 19 is a trans-abdominal ultrasound at 4 weeks gestation demonstrating an intrauterine pregnancy following transfer of gene-edited embryos into feline recipient.
Figure 20:
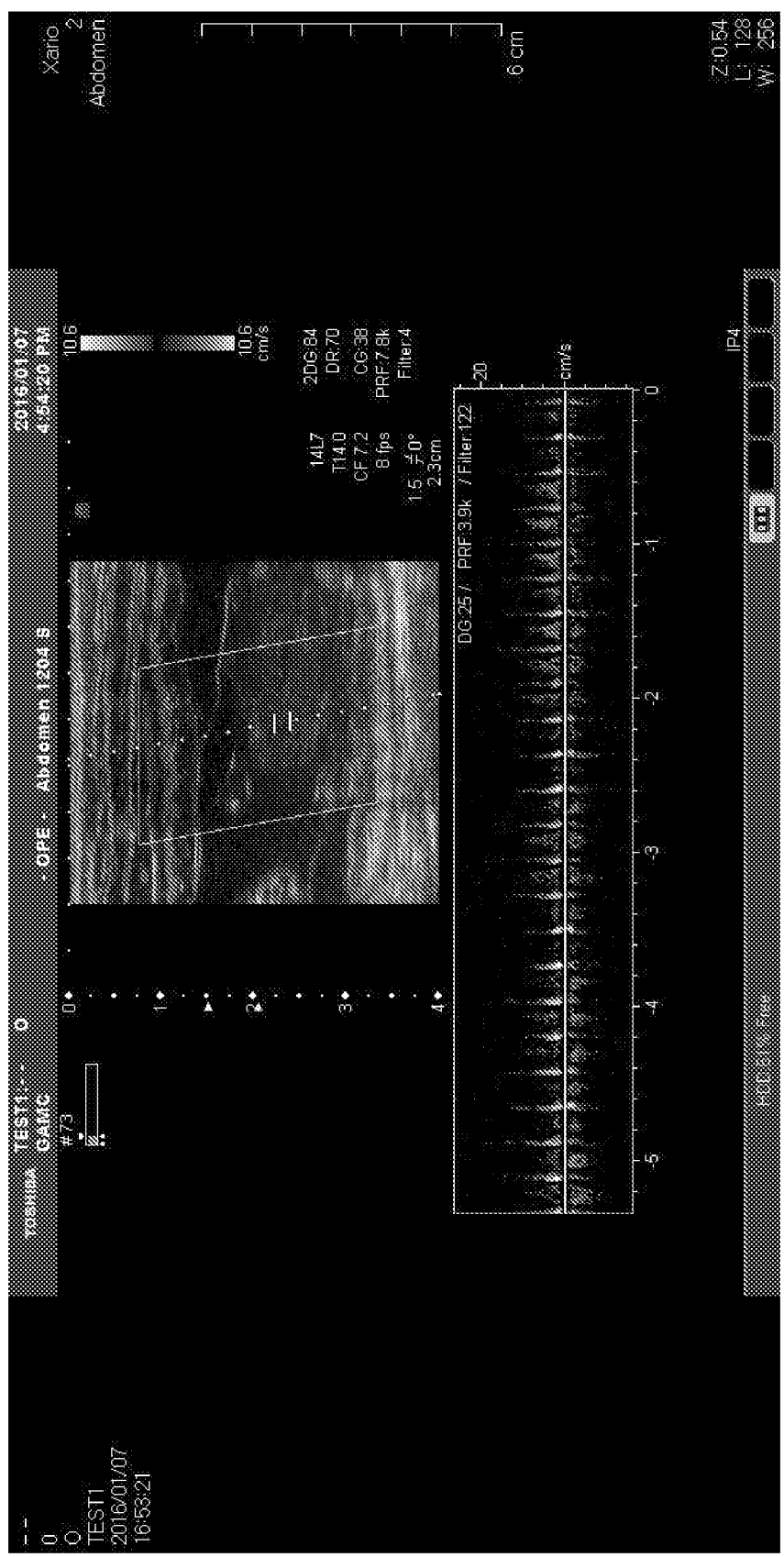
FIG. 20 demonstrates viability of intrauterine pregnancy through use of Doppler ultrasound to measure cardiac activity of fetus.

The gestation period for a cat is approximately 64 days. Intrauterine pregnancies are confirmed by trans-abdominal ultrasound at 3-4 weeks gestation. Viable intrauterine pregnancies after gene editing and embryo transfer are seen in FIG. 19 and FIG. 20.

Figure 21:
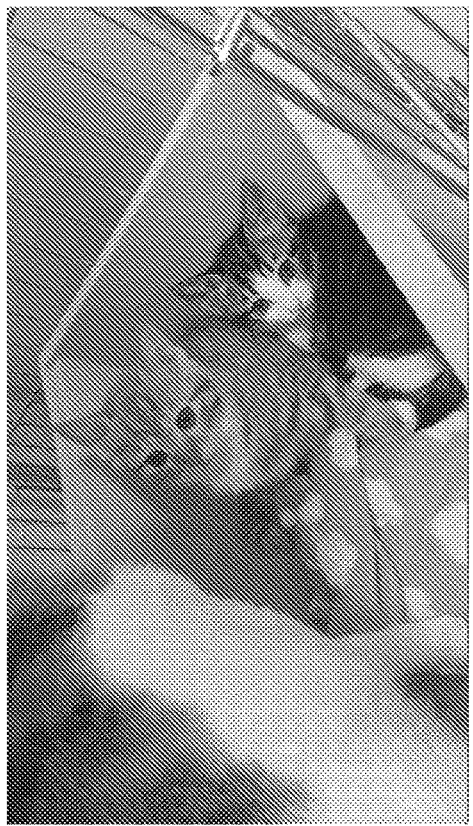
FIG. 21 shows examples of two six-week-old "knock-out" kittens that were delivered naturally at full term. The larger orange kitten is male and the smaller black and white kitten is female.
Figure 22:
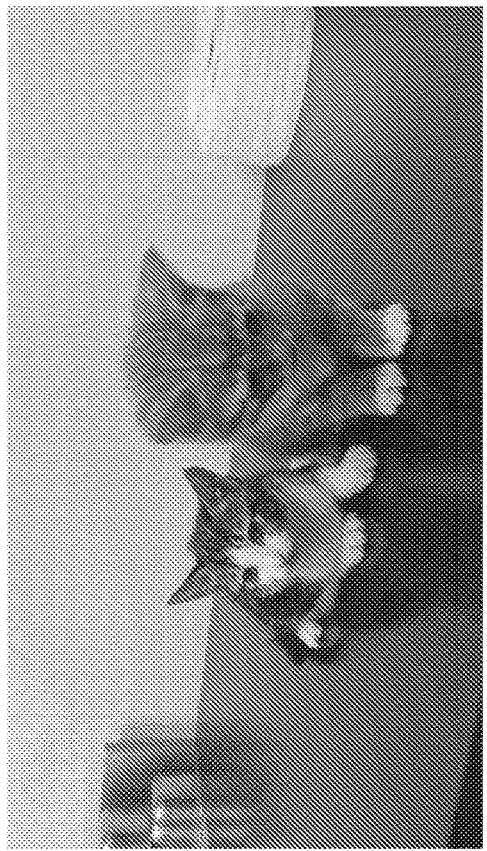
FIG. 22 is another picture of the same two Fel d I "knock-out" kittens at 6 weeks of age.

The recipients are allowed to carry the pregnancies to term. Recipients are allowed to labor and deliver naturally, or the birth can be assisted through cesarean section. FIG. 21 and FIG. 22 show examples of two six week old six-week-old "knock-out" kittens that were delivered naturally at full term and nurtured by the surrogate recipient. The larger orange kitten is male and the smaller black and white kitten is female.

Identification of Heterozygous and Homozygous "Knock-Out" Cats

Figure 23:
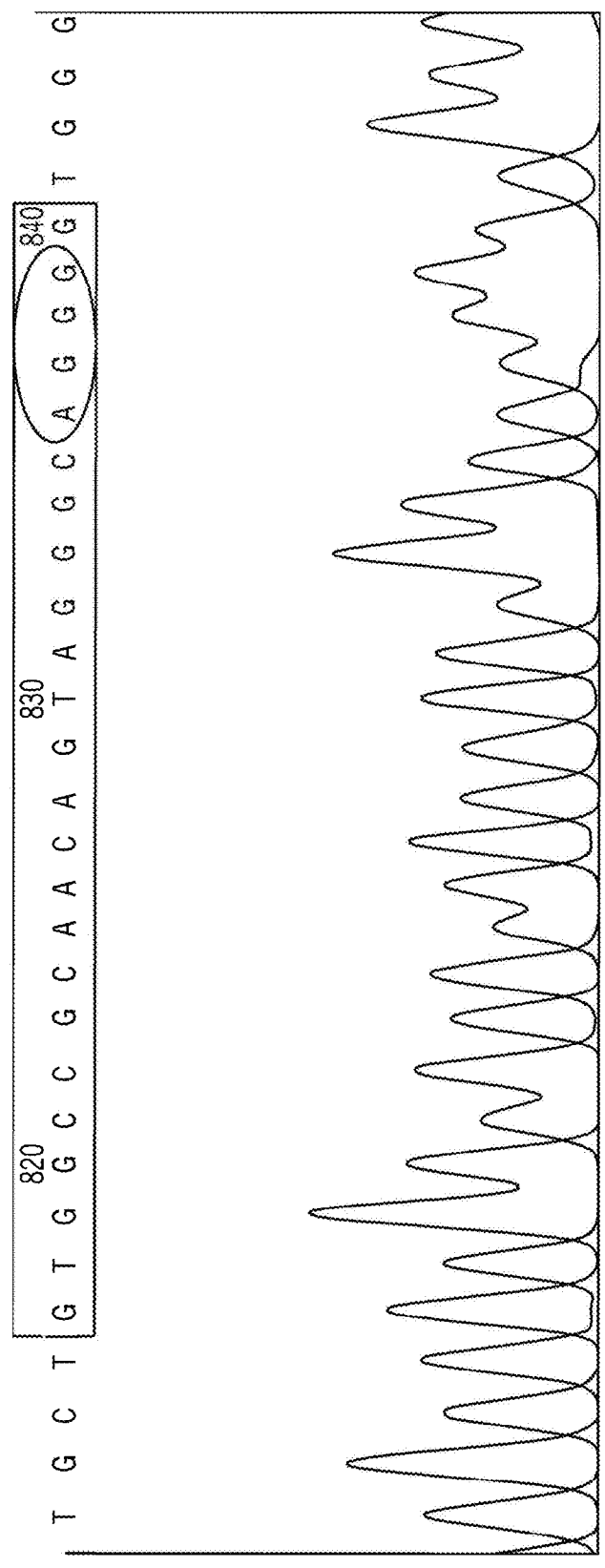
FIG. 23 is the genomic sequencing of Chain 1 of the female kitten demonstrating a one nucleotide insertion, which results in a frameshift mutation.
Figure 24:
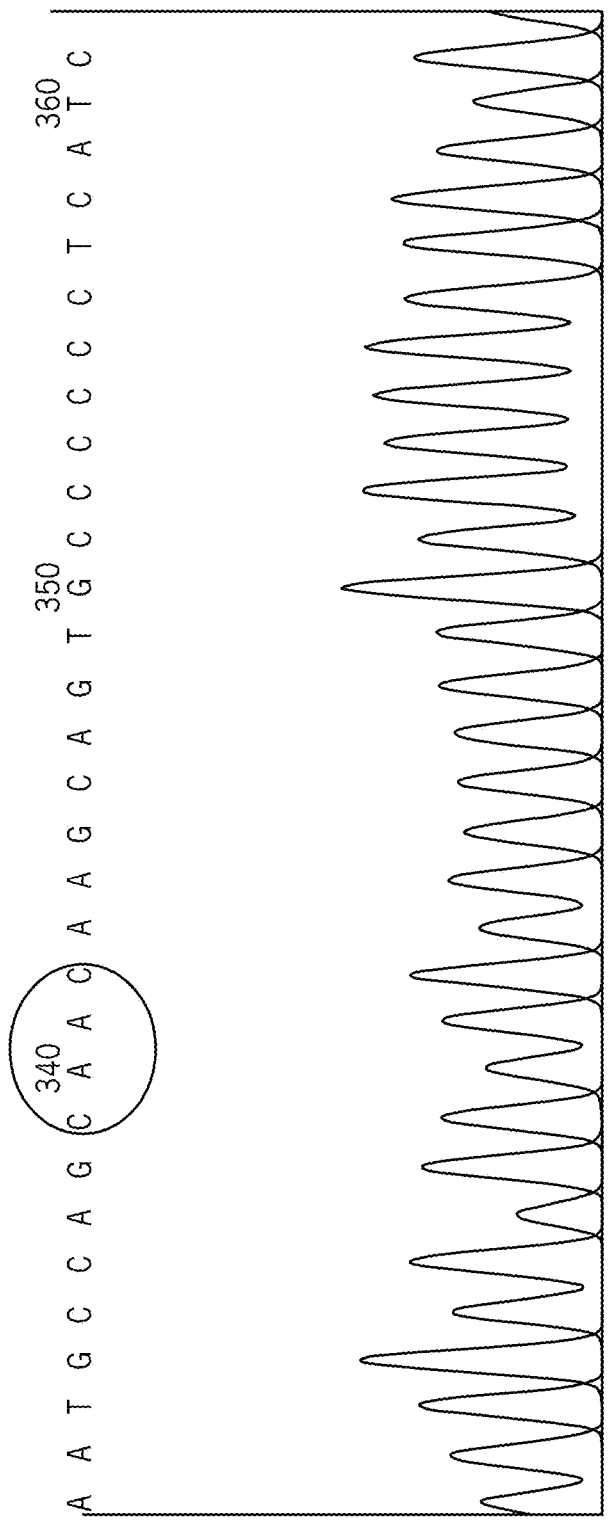
FIG. 24 is the genomic sequencing of Chain 2 of the female kitten demonstrating a one nucleotide insertion, which results in a frameshift mutation.

The molecular techniques described above that are used to confirm correctly targeted Fel d I "knock-out" cells and cell lines are employed to confirm heterozygous and homozygous Fel d I "knock-out" cats. In the case of the two kittens depicted above, tissue samples were taken at 3 weeks of age for genetic testing and to confirm the Fel d I "knock-out" genotype. DNA from the tissue samples was prepped using standard techniques well known in the field, and the Fel d I locus was then PCR amplified. The PCR product was excised from the agarose gel after gel electrophoresis, and Sanger sequenced. The resulting sequence was compared to the online reference genome. Sequencing of the female kitten demonstrates a one nucleotide insertion in chain 1 and a one nucleotide insertion in chain 2 resulting in heterozygous frameshift mutations (see FIG. 23 and FIG. 24).

Figure 25:
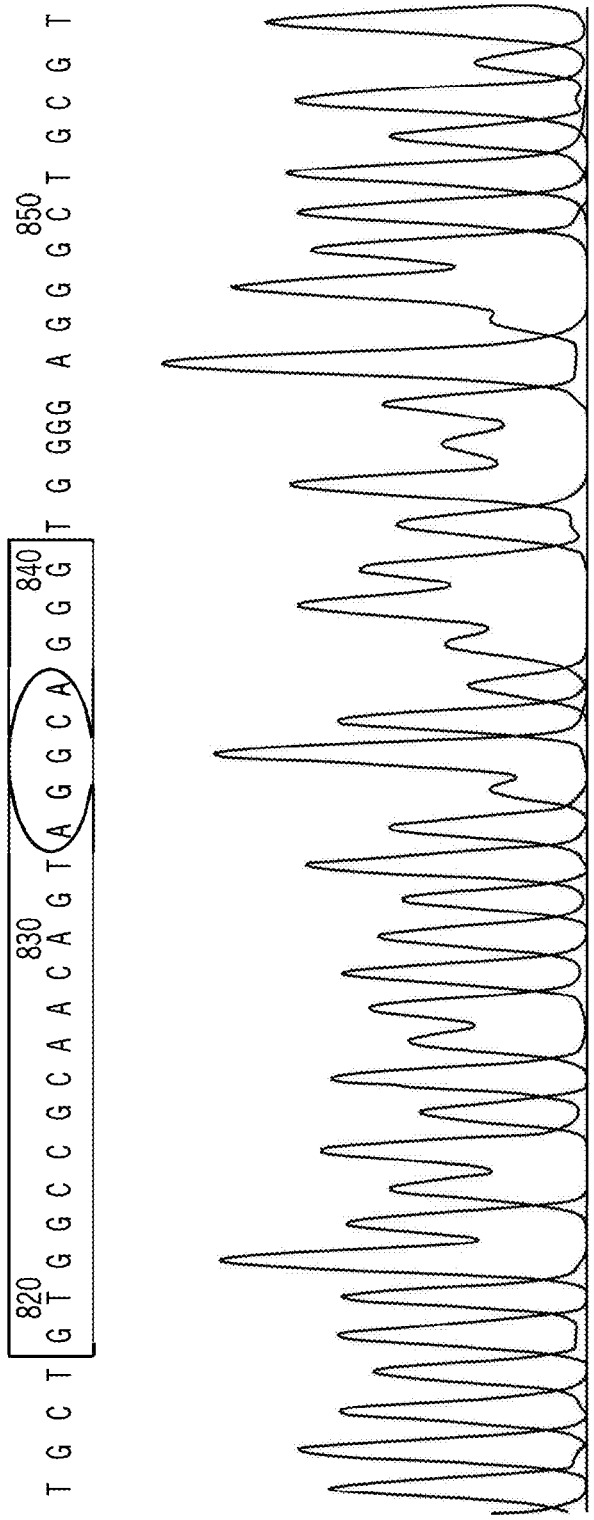
FIG. 25 is the genomic sequencing of Chain 1 of the male kitten demonstrating a one nucleotide deletion, which results in a frameshift mutation.

Sequencing of the male kitten demonstrates a one nucleotide deletion in chain 1 and a one nucleotide insertion in chain 2 resulting in a heterozygous frameshift mutation (see FIG. 25 and FIG. 26).

Sequencing results demonstrate the successful development of a Fel d l heterozygous "knock-out" male and female cat through the process of targeted gene editing.

ELISA testing was then performed on the two kittens to confirm decreased expression of the Fel d I protein. Briefly, the following steps were taken to prepare fur samples for ELISA testing:

1. Three samples of fur were collected from each test subject during routine grooming. Samples were obtained the day before bathing the kittens, the day after bathing the kittens, and seven days after bathing the kittens.
2. 0.05 gm of fur from each subject is placed into a 15 ml centrifuge tube and extracted in 3 ml of tap water or phosphate buffered saline (PBS) containing 0.05% v/v Tween 20. Any hair that rises above the surface of the liquid is pressed down beneath the surface so that the hair is completely submerged.
3. Samples are then placed in a vortex mixer for 15 minutes to facilitate penetration of extraction solution into the fur.
4. Sample tubes are then incubated at 4° C. for between 16-24 hours.
5. The hair and tap water or PBS/Tween is then centrifuged at 1900 g for 15 minutes at 4° C.
6. Samples of the supernatant are removed and stored at −20° C. prior to assaying.

Similarly, saliva samples from the test subjects were prepared using the following steps:
1. Saliva is collected from the inside cheek of the subject with a standard buccal swab.
2. The saliva coated cotton tip is then placed into a 15 ml centrifuge tube and extracted in 3 ml of tap water or phosphate buffered saline (PBS) containing 0.05% v/v Tween 20. The cotton tip must be completely submerged beneath the surface of the liquid.
3. Samples are then placed in a vortex mixer for 15 minutes to facilitate penetration of the extraction solution into the cotton.
4. Sample tubes are then incubated at 4° C. for between 16-24 hours.
5. The cotton tip and tap water or PBS/Tween is then centrifuged at 1900 g for 15 minutes at 4° C.
6. Samples of the supernatant are removed and stored at −20° C. prior to assaying.

Figure 27:
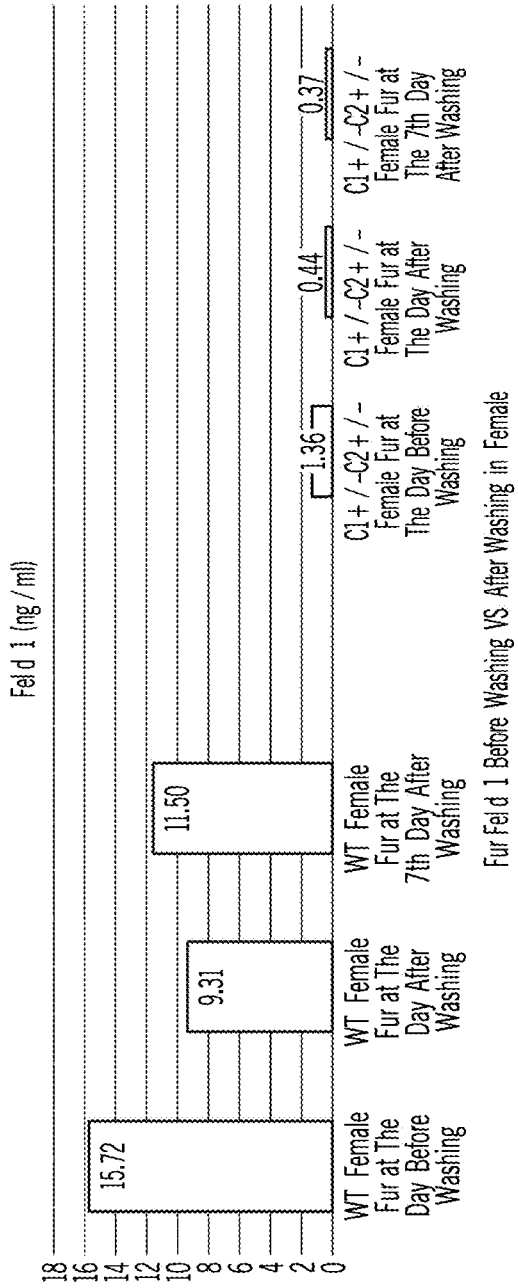
FIG. 27 is the results of Fel d I ELISA testing of fur from a female "knock-out" cat versus fur from a female wild type cat. Results demonstrate reduction in the expression of Fel d I on the cat's fur in "knock-out" female test subjects when compared to wild type.
Figure 28:
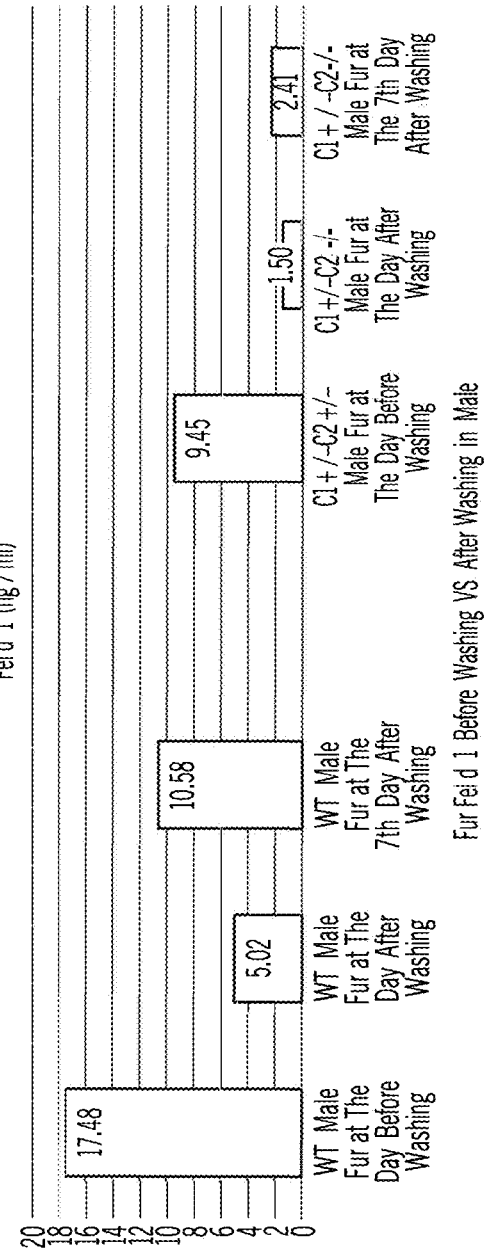
FIG. 28 is the results of Fel d I ELISA testing of fur from a male "knock-out" cat versus fur from a male wild type cat. Results demonstrate reduction in the expression of Fel d I on cat's fur in "knock-out" male test subjects when compared to wild type.
Figure 29:
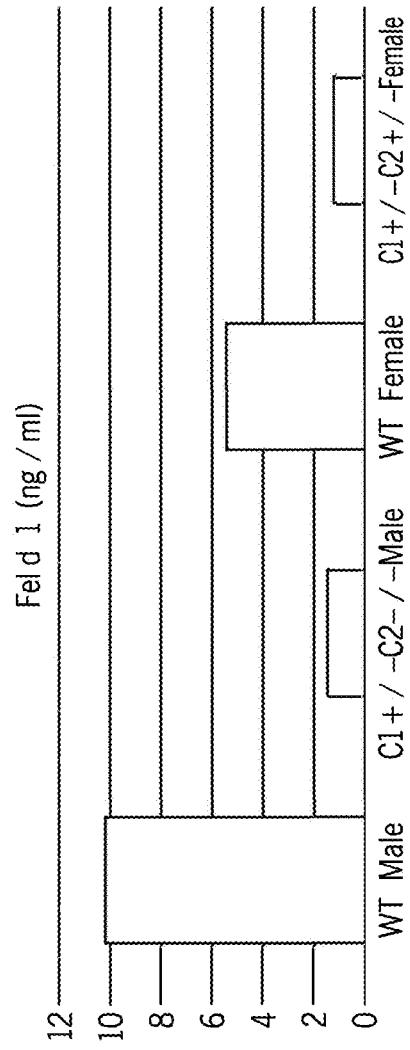
FIG. 29 is the results of Fel d I ELISA testing of saliva from male and female "knock-out" cats versus saliva from wild type male and female cats. Results demonstrate reduction in the expression of Fel d I in the saliva of male and female "knock-out" test subjects when compared to wild type.

Commercially available ELISA kits, such as those available at Indoor Biotechnologies, were used to test the expression of Fel d I in the fur and saliva samples of the test subjects and wild type cats. The results of ELISA testing on the subjects' fur compared to wild type are shown in FIG. 27 and FIG. 28. The results of ELISA testing the subjects' saliva compared to wild type are shown in FIG. 29.

The results of ELISA testing on fur and saliva successfully demonstrate a reduction in the expression of Fel d I protein in the test subjects when compared to wild type cats.

The DNA sequencing and ELISA results confirm the successful development of Fel d I heterozygous "knock-out" male and female cats through the process of targeted gene editing. The kittens produced are bred to homozygosity through traditional mating as described below.

Traditional Mating

Founding cats in which one or both alleles of the Fel d I locus has been knocked out can be mated after puberty at 8-11 months and be expected to transmit their altered Fel d 1 genotype to their progeny. Mature founders that are homozygous for the Fel d I knockout allele can be directly mated to establish stable lines of cats lacking the Fel d I allergen through conventional breeding. Alternatively, heterozygous founders can be crossed and expected to produce kittens that are homozygous for the Fel d I "knock-out" allele at a 25% Mendelian frequency. Cats produced by either route that are homozygous for a disrupted Fel d I locus, resulting in the reduction or complete elimination of the Fel d I mRNA and protein.

Example 1—Gene Editing with TALENs

Figure 30:
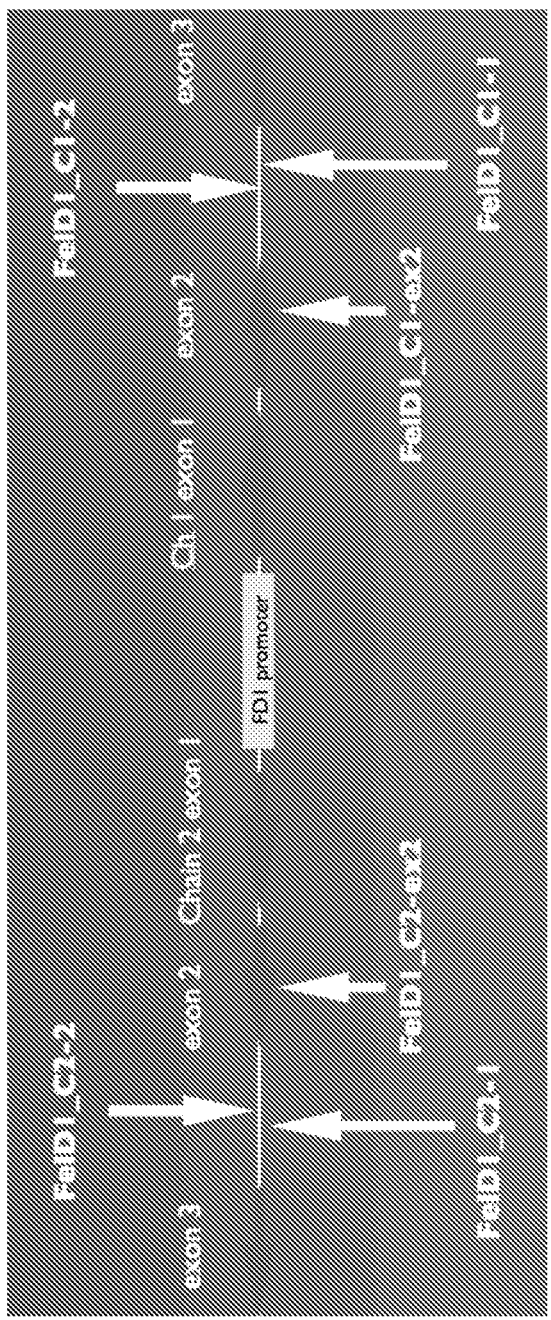
FIG. 30 is an illustration of the three sites on chain 1 of the Fel d I gene and the three sites on chain 2 of the Fel d I gene targeted by uniquely designed TALENs.

TALENs can be designed to target anywhere along the Fel d I locus and flanking sequences. Three TALEN pairs were designed for each of the Fel D I chains (FIG. 30):

```
TALE Nuclease recognition sequences
Underlined = TALE Binding sites Italicized = Cut
region
Chain 1:
FelD1_C1-1
5'TCCTGCACTGCCCTGAGcagaccccccagacaGGCGTCAGAGGCACAG
A3'

FelD1_C1-2
5'TGCCCTGAGCAGACCCCCcagacaggcgtcagaggcACAGACACAGAG
CTAGA3'

FelD1_C1-ex2
5'TCAGGGGTTCCCATCAGgaataggtcaacatccCTCTTCACGGCTGGG
CAA3'

Chain 2:
FelD1_C2-1
5'TATTCCACATACAGACcatgcagtcaggggCTACATGGCAGGTAAGA
3'

FelD1_C2-2
5'TTCACGTTGCGCGTGCAGcagattgtaatattccacATACAGACCATG
CAGTCA3'

FelD1_C2-ex2
5'TCAGCGGAAACTTGCCCCattttttatgacgtcttttTTGCGGTGGCC
AATGGA3'
```

Figure 31:
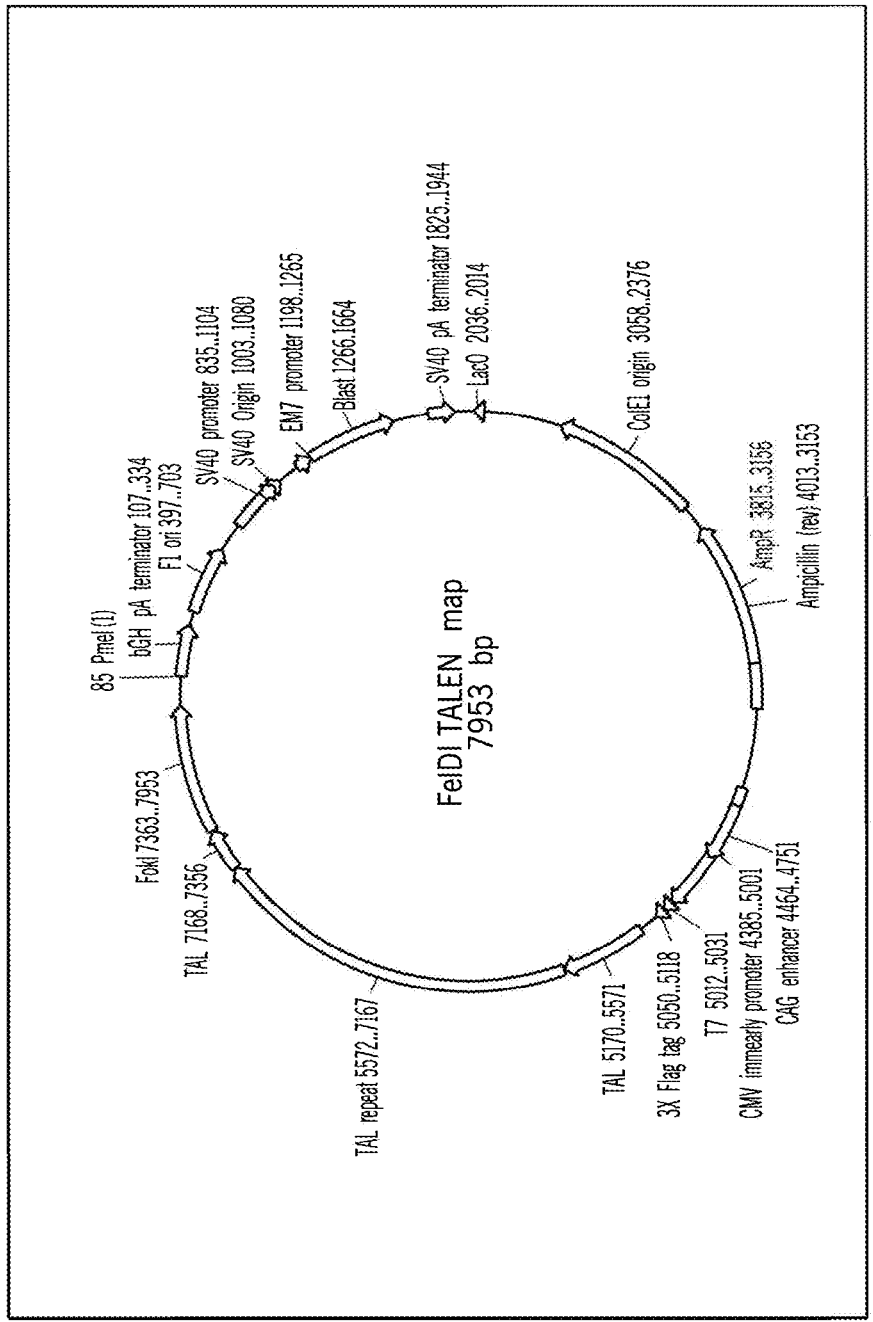
FIG. 31 is a schematic of the plasmid design for the expression of each of the TALEN pairs.

The combination of any of the Chain 1 TALEN with any of the Chain 2 TALEN can lead to a deletion of about 5000 bp of the entire Fel d I promoter region and the first and/or second exon of each chain. The TALEN were cloned in expression plasmids (FIG. 31).

Co-transfections of each of the three TALEN pairs for Chain 1 with each of the three pairs for Chain 2 were performed, for 9 combinations total. Cell lines used were feline embryonic fibroblasts. Transfections were with TALEN plasmid DNA at 2.5 ug each (so 10 ug total) using Lipofectamine 3000, and cell lysates prepared 48 hours post transfection.

Screening was performed by PCR. PCR reactions were optimized by amplifying the entire FelD1 locus (5487 bp) with F4 and R2 or F4 and R1. PCRs were performed with Bioline's MyFi Mix, 35 cycles of (30 s at 94 C, 25 s annealing at 61 C, 180 s extension time at 72 C), for the 5487 bp fragment.

```
Chain1 F4      ACTGAGGCCAAGTGATGCC

Chain2 R2      ctgacaccccgaacctagaa

Chain2 R1      Cctgtggaaggctaaaatcc
```

The extension time was reduced to 30 seconds, to stop the enzyme from amplifying the 5487 bp wild type fragment. Using F4 and R2, bands are observed in sizes between 465 and 897 bp depending on the TALEN combinations used (FIG. 32).

Lanes 1-9 are the 9 combinations of chain 1 and chain 2 TALEN. Lane 10 is negative control (untransfected cell line). The expected size of each PCR product in base pairs is shown:
1. FelD1_C1-1+FelD1_C2-1=465 bp (correct deletion confirmed by sequencing)
2. FelD1_C1-1+FelD1_C2-2=487 bp
3. FelD1_C1-1+FelD1_C2-ex2=704 bp
4. FelD1_C1-2+FelD1_C2-ex2=713 bp (correct deletion confirmed by sequencing)
5. FelD1_C1-2+FelD1_C2-2=496 bp (correct deletion confirmed by sequencing)
6. FelD1_C1-2+FelD1_C2-1=474 bp
7. FelD1_C1-ex2+FelD1_C2-ex2=897 bp (correct deletion confirmed by sequencing)
8. FelD1_C1-ex2+FelD1_C2-2=680 bp
9. FelD1_C1-ex2+FelD1_C2-1=658 bp
10. Negative control (untransfected cell line)

A semi-nested PCR with F4-R1 25 cycles followed by F4-R2 25 cycles was performed as well. This yielded bands in three additional lanes.

Those PCR products were Sanger sequenced, and sequences aligned to the cat genome using the BLAT tool of the UCSC genome browser (genome.ucsc.edu).

A total of 4/9 combinations showed the exact expected deletion of the entire locus.

Of the single PCR with F4 and R2, the bands in lane 1, 4, and 7 were of the expected size and the Sanger sequences confirmed the exact deletion of the expected sequence.

Of the semi-nested PCR with F4 and R1 followed by F4 and R2, combinations 4 and 5 produced bands of the expected size and the Sanger sequences confirmed the exact deletion of the expected sequence.

Combined, TALEN combination 1, 4, 5, and 7 produced the expected results. Other combinations failed to amplify a band in the 400-900 bp range (suggesting no large deletion was made), or showed a deletion that did not exactly match the predicted sequence.

The alignment derived from the first PCR product (lane 1, cell line transfected with FELD1_C1-1+FELD1_C2-1) is shown in FIG. 33.

Forward sequence from transfection with FELD1_C1-1+ FELD1_C2-1, amplification with F4 and R2 and sequenced with F4. The underlined sequence aligns with the intron between Chain 2 exon 2 and 3, the italicized sequence aligns with the intron between Chain 1 exon 2 and 3.

Figure 34:
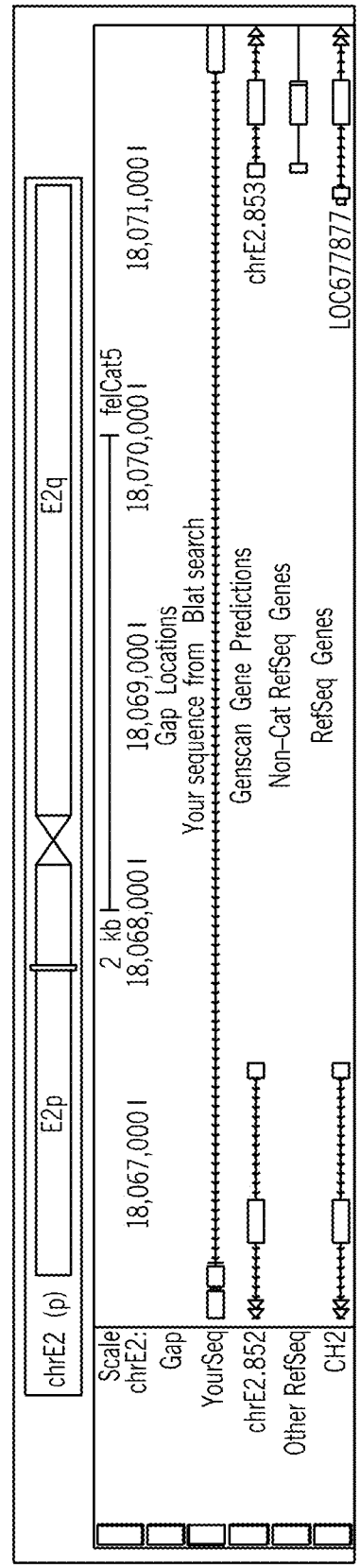
FIG. 34 shows the alignment of sequencing product at the Fel d I locus post "knock-out" compared with the UCSC genome browser and confirms that the entire Fel d I locus is deleted including the promoter region.

FIG. 34 shows the alignment of this sequencing product with the UCSC genome browser, using the ICGSC Felis_catus 6.2/felCat5 assembly of the cat genome. "YourSeq" is the alignment of the sequence of the PCR product, aligning with the introns between exon 2 and 3 of each Fel d I genes (labeled "chrE2.852" for Chain 2 and "chrE2.853" for Chain 1 in the figure). The arrow sequence connecting both ends of "YourSeq" represents ~4 kb of sequence that has been deleted by the TALENs, which contains exon 1 and 2 of each chain and the entire promoter region.

The six combinations that removed the locus were combinations of each of the 6 TALEN pairs. That means that FelD1_C1-1, FelD1_C1-2, FelD1_C1-ex2 all cut the expected genomic location, as well as FelD1_C2-1, FelD1_C2-2, FelD1_C2-ex2.

The combination of TALENs cutting Chain 1 and Chain 2 is able to remove the complete coding sequence of exon 1 and 2 of Fel d I Chain 1 and Chain 2 genes and the joint promoter region, thereby creating a successful "knock-out" of the Fel d I locus. The remaining nucleotide sequences at the locus are not transcribed due to the lack of canonical and non-canonical transcription start sites. The "knock-out" Fel d I locus does not produce translatable mRNAs.

Example 2—Gene Editing with CRISPR/Cas9

Figure 35:
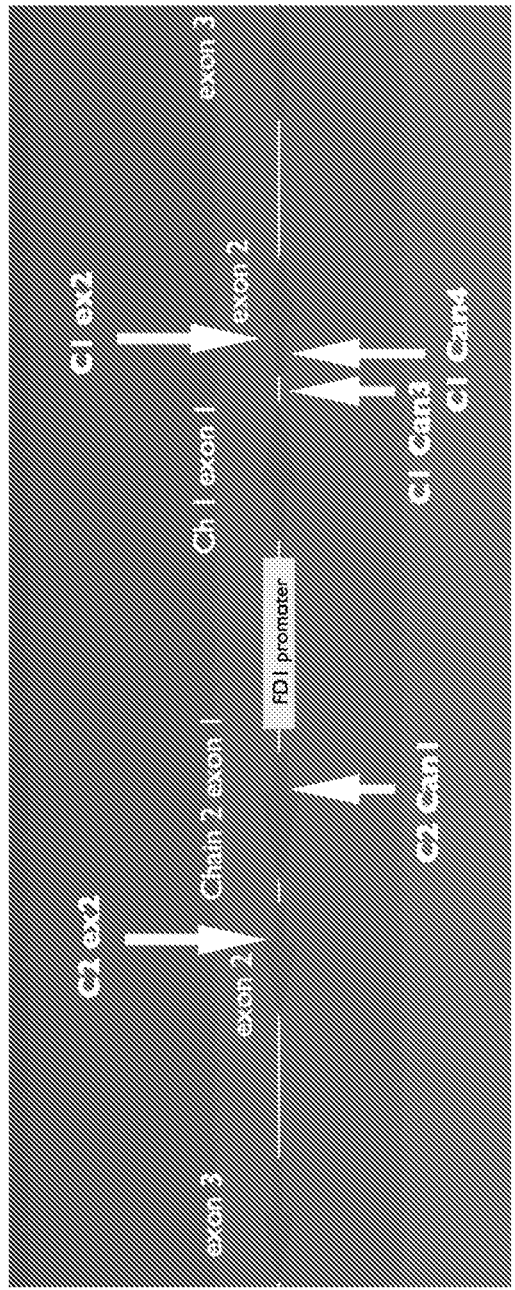
FIG. 35 is an illustration of the three sites on chain 1 of the Fel d I gene and the three sites on chain 2 of the Fel d I gene targeted by uniquely designed CRISPR/Cas9 guide RNAs.

CRISPR/Cas9 can be designed to target anywhere along the Fel d I locus and flanking sequences. Guide RNA is designed to target unique DNA sequence within the Fel d I locus and flanking sequences. These unique sequences can be identified in publically available genomic libraries like the ICGSC Felis_catus 6.2/felCat5 assembly of the cat genome. Using information from these genome assemblies we designed multiple CRISPR/Cas9 pairs for each of the Fel d1 chains (FIG. 35).

The following are examples of guide crRNAs that can be identified by searching the genomic library and used to target Chain 1 and Chain 2 of the Fel d I locus:

```
Chain 1:
C1 can3:       GGCTGCCTTGCTCTTGATCT

C1 can4:       GATGTTGACCTATTCCTGAC

C1 ex2:        CCATCAGGAATAGGTCAACATCC

Chain 2:
C2 can1:       GAGGGGGCACTGCTTGTGC

C2 ex2:        GTCTTTTTTGCGGTGGCCAATGGA
```

Feline embryonic stem cells and iPS cell lines reprogrammed from feline fibroblasts were co-transfected in micro-tubes with a combination of CRISPR/Cas9 candidates targeting Chain 1 and Chain 2. Cells were co-transfected with Lipofectamine 3000, and approximately 125 ng of a CRISPR/Cas9 candidate targeting Chain 1 and 125 ng of the CRISPR/Cas9 candidate targeting Chain 2. Cell lysates were prepared 48 hours post transfection.

Screening was performed by PCR. PCR reactions were optimized by amplifying the entire FelD1 locus (5487 bp) with F4 and R2 or F4 and R1. PCRs were performed with Bioline's MyFi Mix, 35 cycles of (30 s at 94 C, 25 s annealing at 61 C, 180 s extension time at 72 C), for the 5487 bp fragment.

```
Chain1 F4      ACTGAGGCCAAGTGATGCC

Chain2 R2      ctgacaccccgaacctagaa

Chain2 R1      Cctgtggaaggctaaaatcc
```

The extension time was reduced to stop the enzyme from amplifying the 5487 bp wild type fragment. Using F4 and R2, bands are observed in sizes between approximately 500-1600 bp depending on the guide RNA combinations used.

Figure 36:
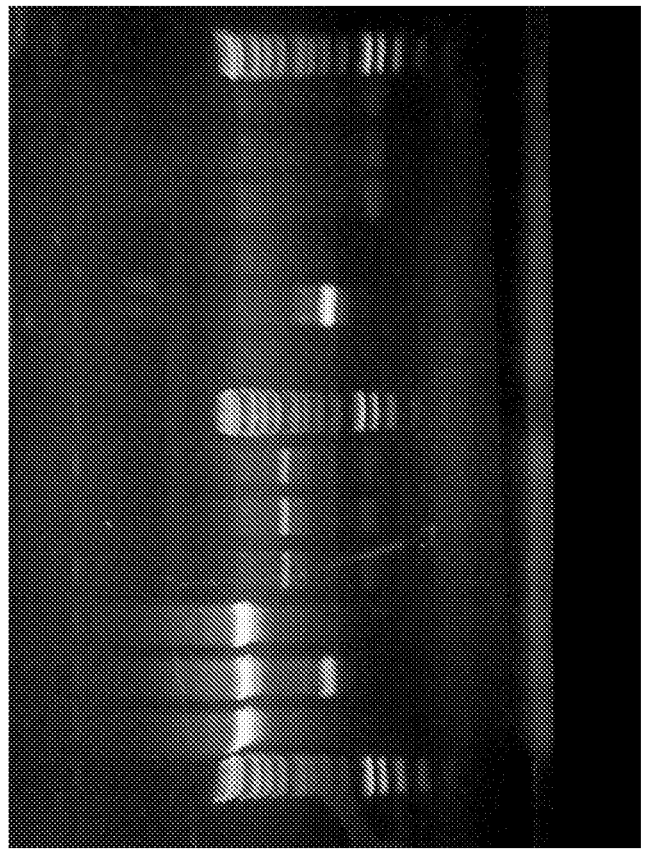
FIG. 36 is a picture of a gel that demonstrates deletions of the Fel d I locus using various combinations of CRISPR/Cas9 guide RNA candidates targeted against iPS cells and ES cells.

The following is the key for the combination of CRISPR/Cas9 candidates and cell types transfected in micro-vials, and for reading the gel PCR lanes (FIG. 36):

From left to right, starting after the left ladder lane:
Lane 1: C1 Can 3-C2 Can 1 in iPSCs
Lane 2: C1 Can 4-C2 Can 1 in iPSCs
Lane 3: C1 Ex 2-C2 Ex 2 in iPSCs
Lane 4: C1 Can 3-C2 Can 1 in ES cells
Lane 5: C1 Can4-C2 Can 1 in ES cells
Lane 6: C1 Ex 2-C2 Ex 2 in ES cells The PCR gel shows three DNA ladders; one of the far left, one in the middle, and one on the far right. The six lanes on the left were run with the 3-minute extension time to allow for the amplification of the wild type locus. The six lanes on the right are the same 6 samples run with a shorter extension time so the wild type locus does not amplify and the signal of the shorter fragments are stronger.

Figure 37:
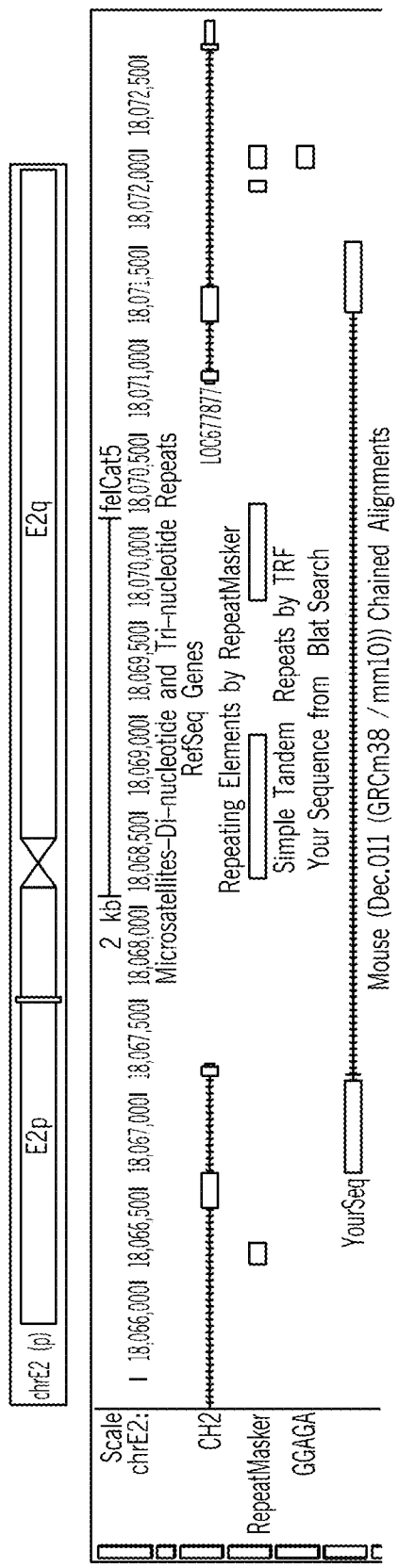
FIG. 37 is a comparison of the genetic sequence of the residual nucleotides at the Fel d I locus after a large section of the Fel d I gene was removed and repaired through end-to-end anastomosis to the cat genome using the BLAST tool from the UCSC genome browser. Comparison demonstrates that exon 1 from Chain 1, exon 1 from Chain 2, and the entire Fel d I promoter region in between the two chains has been deleted resulting in a Fel d I "knock-out."

The bright bands at the top of the gel in lanes 1, 2, and 3 demonstrate the wild type locus of 5487 base pairs. The WT locus does not amplify in 4, 5, and 6. Shorter bands can clearly be seen in lane 2 and in the second lane after the middle DNA ladder, which has the same sample ran with shorter extension times. These bands represent the residual nucleotides at the Fel d I locus after large sections of the Fel d I gene were removed and the ends repaired through end-to-end anastomosis. For confirmation, the PCR product from the small band in lane 2 was Sanger sequenced. The sequence was then aligned to the cat genome using the BLAST tool of the UCSC genome browser (genome.ucsc.edu), using the ICGSC Felis_catus 6.2/felCat5 assembly of the cat genome. The results are shown in FIG. 37.

On the left is exon 2 and 1 (in that order) for CH2. On the right is exon 1 and 2 for CH1. Below, is "YourSeq", which is the sequence of the PCR product from lane 2. Half of "YourSeq" aligns with the intron on the left and the other half with exon 2 and intron 2 on the right. This demonstrates that exon 1 from Chain 1, exon 1 from Chain 2, and the entire Fel d I promoter region in between the two chains has been deleted resulting in a Fel d I "knock-out."

Similar testing demonstrates that the combination of either of the Chain 1 CRISPR/Cas9 candidates with the Chain 2 CRISPR/Cas9 candidate leads to a deletion of about 4000 bp which includes the entire Fel d I promoter region and the first and/or second exon of each chain.

Individual iPS cells from the bulk culture in micro-tube 2 were plated into a 96-well plate. Clones in each well were expanded, split, and prepped for PCR analysis as previously described. Sub-clones with heterozygous and homozygous Fel d I "knock-out" were identified by PCR.

Figure 38:
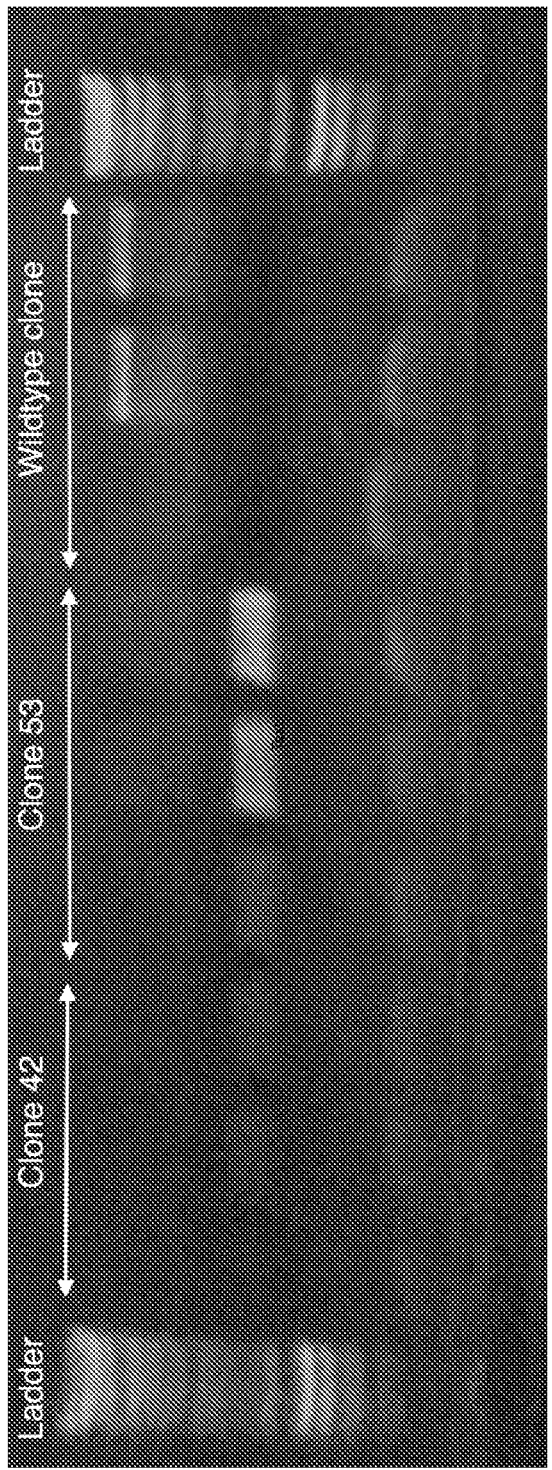
FIG. 38 is a picture of a gel showing homozygous Fel d I "knock-outs" that were sub-cloned from iPS cells in bulk cultures that contained wild type cells, heterozygous "knock-outs," and homozygous "knock-outs."

PCR amplification of DNA prepared from individual clones is shown in FIG. 38. The left three lanes between DNA ladders are PCR product of Clone 42 at three different DNA concentrations. Middle 3 lanes are PCR product of Clone 53 at three different DNA concentrations. Right 3 lanes are PCR product of a wildtype clone at three different DNA concentrations.

Figure 39:
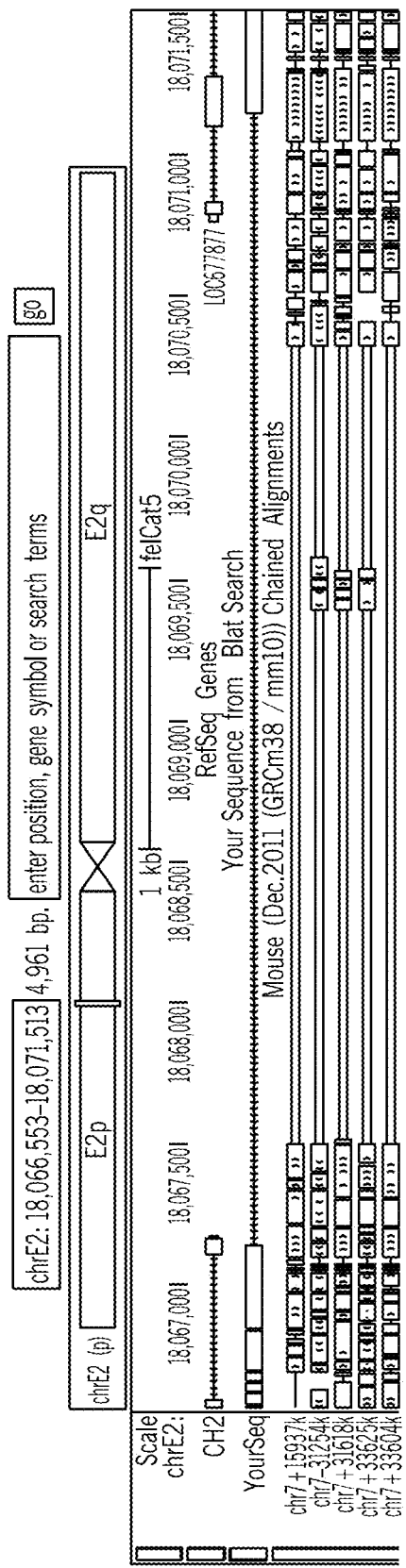
FIG. 39 compares the DNA sequences of homozygous "knock-out" sub-clone 53 that was identified by PCR with the cat genome using the BLAST tool of the UCSC genome browser. Comparison confirms that part of exon 2 and all of exon 1 is deleted is deleted in Chain 1. In Chain 2, part of exon 1 is deleted. In addition, the entire promotor region between Chain 2 and Chain 1 is deleted.
Figure 40:
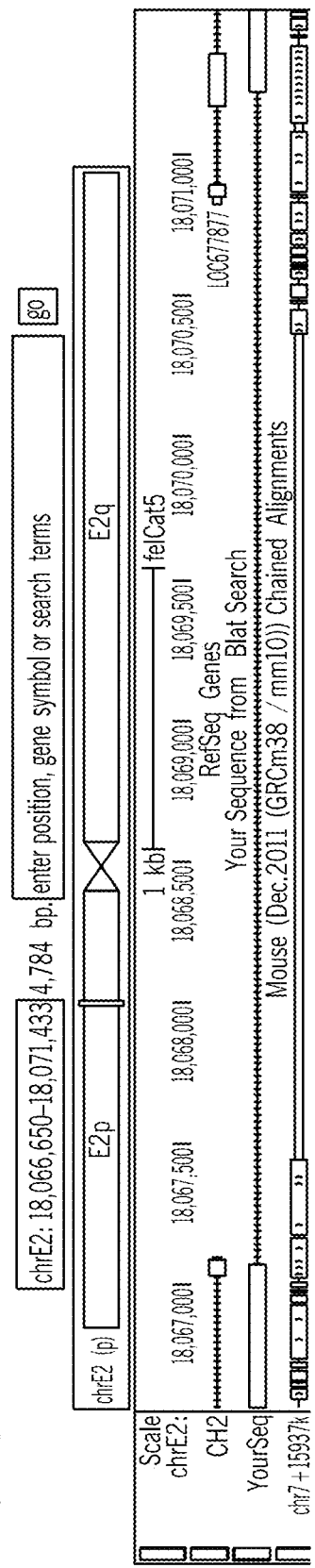
FIG. 40 compares the DNA sequences of homozygous "knock-out" sub-clone 42 that was identified by PCR with the cat genome using the BLAST tool of the UCSC genome browser. Comparison confirms that part of exon 2 and all of exon 1 is deleted is deleted in Chain 1. In Chain 2, part of exon 1 is deleted. In addition, the entire promotor region between Chain 2 and Chain 1 is deleted.

Those sub-clones that appeared to have a homozygous "knock-out" by PCR were Sanger sequenced and compared to the cat genome using the BLAST tool of the UCSC genome browser (genome.ucsc.edu) using the ICGSC Felis_catus 6.2/felCat5 assembly of the cat genome. The results from Clone 53 are shown in FIG. 39. The results from Clone 42 are shown in FIG. 40.

The sequence listed as "YourSeq" aligns with the first intron from ch2 on the left and the second intron of ch1 on the right. This confirms that part of exon 1 is deleted in Chain 2. In Chain 1 part of exon 2 and all of exon 1 is deleted. In addition, the entire promotor region between Chain 2 and Chain 1 is deleted. Further, sequencing demonstrates that the chromosome was repaired through end-to-end anastomosis at the CRISPR/Cas9 cut sites without insertion or deletion of any additional base pairs. These results clearly demonstrate the creation and isolated of a feline, homozygous, Fel d I "knock-out" cell line. This cell line and similar cell lines are used to create homozygous Fel d I "knock-out" cats.

Fel d I sequences are known in the art. For example, see "UCSC Genome Browser on Cat Sep. 2011 (ICGSC Felis_catus 6.2/felCat5) Assembly." Chain 1 is located on the +strand of chromosome E2, position chrE2:18070762-18072692 on ICGSC Felis_catus 6.2/felCat5, while chain 2 is located on the—strand of chromosome E2, position chrE2:18064803-18067167 on ICGSC Felis_catus 6.2/felCat5. As such, the combined gene sequence spans position chrE2:18064803-18072692 for a total size of 7889 bp. Additional sequence information can be found as follows, and in references cited therein:

Chain 1 reference: www.ncbi.nlm.nih.gov/nuccore/NM 001048153?report=GenBank

Chain 2 reference: www.ncbi.nlm.nih.gov/nuccore/NM 001048154?report=GenBank

Reference sequences are provided below. Exon sequences are in capital letters and underlined, with the addition of bold face type indicating coding sequences. Chain 2, exon 1, starts with sequence #18067169, and everything upstream of it is regulatory sequence from 18067218 and below. Chain 1, exon 1, starts with sequence #18070762, and everything upstream of it is regulatory sequence from 18070761 and below.

Chain 2: exon sequences are in capital letters and underlined, with bold face type indicating coding sequences

```
gcctttggag cttctggggg gggggtgtg ggctgggctt aaggtgctag    18067218 tagtttataa agcagcagaa atcctgtcct gagcagagca ttctagcagc    18067168

TGACACGATG AGGGGGGCAC TGCTTGTGCT GGCATTGCTG GTGACCCAAG    18067118

AGCTGGGCGT CAAGATGGgt gagagcagat ggagggacag aggaccttcc    18067068 tgatccttgc cctgctctat ctcactcctt tacctcccat ggtgatctcc    18067018 aaacaggttc tagccacaaa gttaagcggc agctgggaga tcattgtcca    18066968 ggagtcctgc agaaccccc tggtgttttt agtcgtagaa tggagggaga    18066918 ggtttggaga tggagggatc attagttgtg cacacaatag gggagagtta    18066868 gttggggta gtggtgctta tttgaaaggc cgaaacaggc aggctggggt     18066818 gcccggaggc accggtcagg ggtctctccg gctgctctct tctgctgaga    18066768 gtgcctcata gaaatgttc cgtctgtctg ggatgtaagc agtcctggga     18066718 gtgggcaggt ctctgcggaa ggtgagtcag aagaccctgg atatatgtga    18066668 gttgctctca agtggcgggc aaacaggaac ctcctgctct gctgattctt    18066618 ttgtgaaggt gttttctgtt tgtgtcttca gCGGAAACTT GCCCCATTTT    18066568

TTATGACGTC TTTTTTGCGG TGGCCAATGG AAATGAATTA CTGTTGGACT    18066518

TGTCCCTCAC AAAAGTCAAT GCTACTGAAC CAGAGAGAAC AGCCATGAAA    18066468

AAAATCCAGG ATTGCTACGT GGAGAACGGA CTCTTATCCA GGGTCTTGGA    18066418
```

-continued

| | |
|---|---|
| TGGACTAGTC ATGgtaattt cctttccttc cccgcctccc caaccttcac | 18066368 |
| gttgcgcgtg cagcagattg taatattcca catacagacc atgcagtcag | 18066318 |
| gggctacatg gcaggtaaga gctataaaca atcgagcaca taaacctttg | 18066268 |
| ctccgctcta cagcacatag aatacgcaac ctcacgccat gtgcacaccc | 18066218 |
| agcctgttct tctaccacac gtgtcccttg tgtgcgaatt accttacgca | 18066168 |
| cagttggaaa ataggggact aatatcggtg tggcatagaa agcgtgttga | 18066118 |
| ctcgtaggat ttttttcttt ctaggttcgg ggtgtcagaa ttgcaggagt | 18066068 |
| aggattttag ccttccacag gaaagagaaa gttcttcatt cagctcctgc | 18066018 |
| acatgtagga gccttgtcag ttctggtgga ggaatattga aactaaggca | 18065968 |
| cctgccctca gactctcttc ccaggaaggg actccctggc tttgggaagc | 18065918 |
| ttctggtttt tggcttctgt tttacttccc cttgtgccca ccttgatggc | 18065868 |
| tgctattcct ttggttcaga gtctcacttc cttctgtatc aattcagggt | 18065818 |
| ctaaagtcag attttccact ctgttgttct ggtgcctgag gccctcgagg | 18065768 |
| cagctcctag ctacgtgcag ctgcacccca gggctggtca gtgtatttct | 18065718 |
| ggtgaactat cttttctgt tattttcttt gttgcacagt taggtcgatt | 18065668 |
| ttggttagtc tgtctcttac ctctacttgc cgttaagtgc tgattctgta | 18065618 |
| aaatgagagc tttgtgaaga agtggaattt cttgcatgac tacgggcacc | 18065568 |
| cagggcacat gggattgttc acaacacaca catacacatt ccatacatcc | 18065518 |
| agtacacctg acagatgagt ctcaggtgag ggagacatcg catggaccca | 18065468 |
| gactcagcta ccttgcccct cacccaggcc cagccccnn nnnnnnnnn | 18065418 |
| nnnnnnnnnn nnnnnnnnnn nnnnnnnnnn nnnnnnnnnn nnnnnnnnnn | 18065368 |
| nnnnnnnnnn nnnnnnnnnn nnnnnnnnnn nnnnnnnnnn nnnnnnnnnn | 18065318 |
| nnnnnnnnnn nnnnnnnnnn nnnnnnnnnn nnnnnnnnnn nnnnnnnnnn | 18065268 |
| nnnnnnnnnn nnnnnnnnnn nnnnnnnnnn nnnnnnnnnn nnnnnnnnnn | 18065218 |
| nnnnnnnnnn nnnnnnnnnn nnnnnnnnnn nnnnnnnnnn nnnnnnnnnn | 18065168 |
| nnnnnnnnnn nnnnnnnnnn nnnnnnnnnn nnnnnnnnnn nnnnnnnnnn | 18065118 |
| nnnnnnnnnn nnnnnnnnnn nnnnnnnnnn nnnnnnnnnn nnnnnnnnnn | 18065068 |
| nnnnnnnnnn nnnnnnnnnn nnnnnnnnnn nnnnnnnnnn nnnnnnnnnn | 18065018 |
| nnnnnnnnnn nnnnnnnnnn nnnnnnnnnn nnnnnnnnnn nnnnnnnnnn | 18064968 |
| nnnnnnnnnn nnnnnnnnnn nnnnnnnnnn nnnnnnnnnn nnnnnnnnnn | 18064918 |
| nnnnnnnnnn nnnnnnnnnn nnnnnnnnnn nnnnnnnnnn nn<u>GCTGGATC</u> | 18064868 |
| <u>CAGACACCTG TCCTCACCTA ATTCACTCTC AATCAGGCTG ACTAGAATAA</u> | 18064818 |
| <u>AATAACTGCA TCTTA</u>gcacc cccgggtgcc ccgtgtctgt gttctgtgcg | 18064768 |
| ggaagcgtgg gaggcctggc aggagatcct gggacatggc aaagggaggt | 18064718 |
| gacatgtgct cattg | |

Chain 1: exon sequences are in capital letters and under-
lined, with bold face type indicating coding sequences

| | |
|---|---|
| aaggtagcgt catctgttga ctcggggact taggatcctg cccacacata | 18070711 |
| catctcctcc ctccacagcc cccaggcagt tctgagaagc agcccagaga | 18070761 |
| <u>GGCCTGGCGG TGCCTCCTGG AAAAGGATGT TAGACGCAGC CCTCCCACCC</u> | 18070811 |

-continued

| | |
|---|---|
| TGCCCTACTG TTGCAGCCAC AGCAGgtata aaagggttcc aggctggggga | 18070861 |
| gggagcacct gccactgcat catgaagggg gctcgtgttc tcgtgcttct | 18070911 |
| ctgggctgcc ttgctcttga tctcgggtgg aagtaggtgt ctgggacatg | 18070961 |
| agtgtctggg gacacagatt ctccaggggt tctaacacct tcccagggca | 18071011 |
| cttctgagca tggcgggaag gggaagggaa gaatgtgtcc tgatgaaggt | 18071061 |
| cttttcaaaag ggagggtcag cttgtctttg tgttccagAT TGTGAAATTT | 18071111 |
| GCCCAGCCGT GAAGAGGGAT GTTGACCTAT TCCTGATGGG AACCCCTGAC | 18071161 |
| AAATATGTTG AGCAAGTGGC ACAATACAAT GCACGACCTG TAGTATTGGC | 18071211 |
| AAATGCCAGA AACCTGAAGA ACTGCGTTGA TGCAAAAATG ACAGAAGAGG | 18071261 |
| ATAAGGAGAA TGCTCTCAGC gtgctggtgg gtctagctct gtgtctgtgc | 18071311 |
| ctctgacgcc tgtctggggg gtctgctcag ggcagtgcag gagggggggtt | 18071361 |
| gctcatgttt gttctccacc atggcccttc cctgggaatc tgggaggaga | 18071411 |
| aagacgccat ggctggggaa gtagaggggga tcatgtgggg aagactcagc | 18071461 |
| ctacccctca agctttgggg ctggcccagg ctgctcaacg ctgcttggcc | 18071511 |
| accggcttgg gggtctgcag gccctcctgt gtccctggca tcacttggcc | 18071561 |
| tcagtgtcag gccctcagct ctggccttcc tgactccagc ctctccagca | 18071611 |
| cgtgagactg gatcttcaaa ctgtttgcac taggtgcttc ctatctccaa | 18071661 |
| acgtcagttc cttttctctt aactcctcaa gttccatatt ccaccccccc | 18071711 |
| cccaaaaaaa aaccctcatt tgtcttcatt ccctgggtcc cagagggcca | 18071761 |
| ttctgtgcct caaatactga gagagaggag gaggggaggg gagaagaggg | 18071811 |
| gcggggcagg gagggacgag gggaggtgag atggggcagc ttccaaaagc | 18071861 |
| cctccccctg ccctgccatt ctgtgcctca cataccaaga gagaggatga | 18071911 |
| tggaagggga ggggagggga gggagggga gggaggggga ggggaggga | 18071961 |
| ggggagagga gaggagagga gaggagagga gaggagagga gaggagagga | 18072011 |
| gaggagagga gaggagaggc agcttccaaa aagttctcct gccctgccca | 18072061 |
| ggcctgggat gccctgagtg gagaattcca gtgaatcctc tctctgctgt | 18072111 |
| cccaaaagta ggaacaagct actgcttcag caacaagtgt tcaaaggaca | 18072161 |
| gaaggaggaa gcaggctgga ccagctcatt cctggagtct cccagatgcc | 18072211 |
| cacaggtgca tctggagccc tgccaggacc ttcttgccag cctctttcta | 18072261 |
| tccaagtcta ccacttctat ccgagactgc cctccatccc atcatagtca | 18072311 |
| cccctcttct tcactctgtt tcattggagg aagcttctag gcacaccctg | 18072361 |
| ggattctctt gttgtgcagt agattgggaa gaaccacctt ggcctgctca | 18072411 |
| gatccagaag ccaccctcca aacaagcctg caggctcctc cccacaaagt | 18072461 |
| gtccagtgcg tgctcagtag agcttgatgt ctcgcgtacc cctcaaggtc | 18072511 |
| tcaccaggtc tcctgacttt ctctTTGCAG GACAAAATAT ACACAAGTCC | 18072561 |
| TCTGTGTTAA TGGAGCCATC ACTGCCAGGA GCCCTAAGGA AGCCACTGAA | 18072611 |
| CTGATTACTA AGTAGTCTCA GCAGCCTGCC ATGTCCAGGT GTCTTACTAG | 18072661 |
| AGGATTCCAG CAATAAAAGC CTTGCAATTC Atggagagtg cttgctcctt | 18072711 |
| gggctgggct tggggggggg ggtggagggg tgttgcagca ggggggaccac | 18072761 |
| cagtgtgcct tccaaccgtg gctagatttg a | |

The invention is further described in the following numbered paragraphs.

1. A feline embryonic stem cell or a feline induced pluripotent stem cell (iPSC) that can be maintained in culture in a pluripotent state for more than 5 passages.

2. The cell of paragraph 1, wherein the cell can be maintained in culture in a pluripotent state for more than 15, 20, or 25 passages.

3. The cell of paragraph 1 or 2, wherein the cell is maintained in a pluripotent state independently from a cytokine of the interleukin-6 family.

4. The cell of paragraph 3, wherein the cytokine of the interleukin-6 family is leukemia inhibitory factor (LIF).

5. The cell of any one of paragraphs 1 to 4, which is cultured in the presence of basic fibroblast growth factor (bFGF) and, optionally, an agonist of the transforming growth factor-beta (TGF-beta) superfamily.

6. The cell of paragraph 5, wherein the agonist of the TGF-beta superfamily is selected from the group consisting of activin, nodal, TGFb1, and TGFb3.

7. The cell of any one of paragraphs 1 to 6, wherein the cell expresses transcription factors Oct4 and Nanog.

8. The cell of any one of paragraphs 1 to 7, wherein the cell can differentiate into multiple tissue types of neurectodermal, mesodermal, and endodermal lineages in vitro by forming cystic embryoid bodies or form teratomas after grafting into immunocompromised mice.

9. A method of generating a feline embryonic stem cell, the method comprising:
    (a) isolating stem cells from the inner cell mass of a cat blastocyst;
    (b) culturing cells isolated in step (a) in an undifferentiated state using one or more condition selected from the group consisting of:
        (i) the absence of a cytokine of the interleukin-6 family, such as LIF,
        (ii) the presence of bFGF and, optionally, one or more agonist of the TGF-beta superfamily, such as activin, nodal, TGFb1, and/or TGFb3,
        (iii) the absence of homologous inactivated feline embryonic fibroblast layers, and
        (iv) the presence of mitotically inactivated mouse embryonic fibroblasts (MEFs) or an extracellular matrix, such as matrigel or laminin.

10. The method of paragraph 9, further comprising passaging said cells by the use of accutase, collagenase, or dispase, but not trypsin.

11. A method of maintaining a feline pluripotent stem cell or a feline iPSC in an undifferentiated state in culture, the method comprising culturing the cell in one or more condition selected from the group consisting of:
    (a) the absence of a cytokine of the interleukin-6 family, such as LIF,
    (b) the presence of bFGF and, optionally, one or more agonist of the TGF-beta superfamily, such as activin, nodal, TGFb1, and/or TGFb3,
    (c) the absence of homologous inactivated feline embryonic fibroblast layers, and
    (d) the presence of mitotically inactivated MEFs or an extracellular matrix such as matrigel or laminin.

12. The method of any one of paragraphs 9 to 11, wherein the cells are passaged every three-four days, and/or the cells are or can be passaged at least 5, 10, 15, 20, or 25 times.

13. A method of generating and maintaining a feline iPSC, the method comprising the steps of:
    (a) expressing transcription factors Oct4, Sox2, cMyc, and Klf4, optionally in combination with Lin28, in a feline fetal or adult somatic cell, and
    (b) maintaining the cells in one or more condition selected from the group consisting of:
        (i) the absence of a cytokine of the interleukin-6 family, such as LIF,
        (ii) the presence of bFGF and, optionally, one or more agonist of the TGF-beta superfamily, such as activin, nodal, TGFb1, and/or TGFb3,
        (iii) the absence of homologous inactivated feline embryonic fibroblast layers, and
        (iv) the presence of mitotically inactivated MEFs or an extracellular matrix, such as matrigel or laminin.

14. The method of paragraph 13, wherein the feline fetal or adult somatic cell is a fibroblast.

15. The method of paragraph 13 or 14, wherein expression of the transcription factors in the cell is achieved by the use of a retroviral vector, a lentiviral vector, a Sendai viral vector, plasmid DNA, mini-circle DNA, mRNA, or protein.

16. The method of any one of paragraphs 13 to 15, further comprising maintaining the cells in an incompletely reprogrammed state for 5 or more passages.

17. A method of producing a genetically modified cell line in which the cells comprise a disrupted Fel d I gene, the method comprising the steps of:
    (a) providing a feline somatic cell, a feline embryonic stem cell, or a feline iPS cell;
    (b) introducing an engineered nuclease comprising a programmable, sequence-specific, DNA binding module fused to a non-specific DNA cleavage domain designed to disrupt coding or non-coding sequences of the Fel d I locus, or flanking DNA sequences, into the feline somatic cell, the feline embryonic stem cell, or the feline iPS cell;
    (b) screening for a cell comprising a correctly targeted Fel d I locus; and
    (c) expanding a targeted cell line comprising a correctly targeted Fel d I locus, wherein the cell line is heterozygous or homozygous for the disrupted Fel d I gene.

18. The method of paragraph 17, wherein said provided cell is a feline somatic cell, and said feline somatic cell is reprogrammed into an iPS cell after step (b).

19. The method of paragraph 17 or 18, wherein the disrupted non-coding sequences comprise regulatory sequences of the Fel d I locus, which optionally comprise sequences of the Fel d I promoter.

20. A method for producing a genetically modified cat comprising a disrupted Fel d I gene, the method comprising the steps of:
    (a) introducing an engineered nuclease comprising a programmable, sequence-specific, DNA-binding module fused to a non-specific DNA cleavage domain designed to disrupt coding or non-coding sequences of the Fel d I locus, or flanking DNA sequences, into a feline embryo;
    (b) transferring said embryo into a feline surrogate recipient; and
    (c) allowing said cat embryo to mature into a cat, wherein the cat is heterozygous or homozygous for the disrupted Fel d I gene.

21. The method of paragraph 20, wherein the disrupted non-coding sequences comprise regulatory sequences of the Fel d I locus, which optionally comprise sequences of the Fel d I promoter.

22. A method for producing a genetically modified cat comprising a disrupted Fel d 1 gene, the method comprising the steps of:

(a) introducing an engineered nuclease comprising a programmable, sequence-specific, DNA-binding module fused to a non-specific DNA cleavage domain designed to disrupt coding or non-coding sequences of the Fel d I locus, or flanking DNA sequences, into a feline embryonic stem cell, a feline somatic cell, or a feline iPS cell;

(b) identifying a cell in which the Fel d I locus has been disrupted by the engineered nuclease;

(c) transferring the nucleus of said cell into an enucleated embryo;

(d) implanting said embryo into a feline surrogate recipient; and (e) allowing said cat embryo to mature into a cat, wherein the cat is heterozygous or homozygous for the disrupted Fel d I gene.

23. The method of paragraph 22, wherein said cell of step (a) is a feline somatic cell and said method further comprises reprogramming said feline somatic cell into an iPS cell after step (a).

24. The method of paragraph 22, wherein said cell of step (a) is an iPS cell that was reprogrammed from a feline somatic cell prior to step (a).

25. The method of paragraph 22, wherein said cell of step (a) is an embryonic stem cell, which is derived from an inner cell mass of a feline blastocyst.

26. A method for producing a genetically modified cat comprising a disrupted Fel d 1 gene, the method comprising the steps of:

(a) introducing an engineered nuclease comprising a programmable, sequence-specific, DNA-binding module fused to a non-specific DNA cleavage domain designed to disrupt coding or non-coding sequences of the Fel d I locus, or flanking DNA sequences, into a feline embryo in addition to a vector or DNA molecule exhibiting sequence homology to sequences surrounding the target site, which may or may not contain a selectable marker;

(b) transferring said embryo into a feline surrogate recipient; and (c) allowing said cat embryo to mature into a cat, wherein the cat is heterozygous or homozygous for the disrupted Fel d I gene.

27. A method for producing a genetically modified cat comprising a disrupted Fel d 1 gene, the method comprising the steps of:

(a) introducing an engineered nuclease comprising a programmable, sequence-specific, DNA-binding module fused to a non-specific DNA cleavage domain designed to disrupt coding or non-coding sequences of the Fel d I locus, or flanking DNA sequences, into a feline embryonic stem cell, a feline somatic cell, or a feline iPS cell, in addition to a vector or DNA molecule exhibiting sequence homology to sequences surrounding the target site, which may or may not contain a selectable marker;

(b) identifying a cell in which the Fel d I locus has been disrupted by the engineered nuclease;

(c) transferring the nucleus of said cell of (b) into an enucleated embryo;

(d) transferring said embryo into a feline surrogate recipient; and (e) allowing said embryo to mature into a cat, wherein the cat is heterozygous or homozygous for the disrupted Fel d I gene.

28. The method of paragraph 27, wherein said cell of step (a) is a feline somatic cell and said method further comprises reprogramming said feline somatic cell into an iPS cell after step (a).

29. The method of paragraph 27, wherein said cell of step (a) is an iPS cell that was reprogrammed from a feline somatic cell prior to step (a).

30. The method of paragraph 27, wherein said cell of step (a) is an embryonic stem cell, which is derived from an inner cell mass of a feline blastocyst.

31. The method of any one of paragraphs 20 to 30, wherein the mature cat is heterozygous for the targeted Fel d I allele and the method further comprises:

(a) breeding the cat to homozygosity by breeding with another heterozygote to produce a homozygous Fel d I knock-out; or (b) breeding the cat to a wild type cat, and breeding the resulting offspring to each other or other heterozygote cats to produce a homozygous Fel d I knock-out.

32. The method of any one of paragraphs 17 to 31, wherein the engineered nuclease is selected from the group consisting of: Cas9, a zinc finger nuclease, a transcription activator-like (TAL) effector nuclease, and Cpf1.

33. A feline somatic cell, embryonic stem cell, or iPS cell, wherein said cell is heterozygous or homozygous for a disruption in Fel d I locus sequences or flanking sequences thereof.

34. The cell of paragraph 33, wherein the disruption is a knock-out.

35. The cell of paragraph 33 or 34, wherein the disruption comprises deletion or mutation of:

(a) the promoter shared by Chain 1 and Chain 2 of the Fel d I locus;

(b) exon 1 of Chain 1 of the Fel d I locus;

(c) exon 2 of Chain 1 of the Fel d I locus;

(d) exon 3 of Chain 1 of the Fel d I locus;

(e) exon 1 of Chain 2 of the Fel d I locus;

(f) exon 2 of Chain 2 of the Fel d I locus;

(g) exon 3 of Chain 2 of the Fel d I locus; or (h) combinations or portions thereof.

36. The cell of paragraph 35, wherein said combination comprises deletion or mutation of (a) and (b); (a), (b), and (c); (a), (b), (c), and (d); (a) and (e); (a), (e), and (f); (a), (e), (f), and (g); (a), (b), and (e); (a), (b), (c), and (e); (a), (b), (c), (d), and (e); (a), (b), (e), and (f); (a), (b), (c), (e), and (f); and (a), (b), (c), (d), (e), and (f); (a), (b), (e), (f), and (g); (a), (b), (c), (e), (f), and (g); (b) and (c); (b), (c), and (d); (c) and (d); (e) and (f); (e), (f), and (g); (f) and (g); or (a)-(g), or portions thereof.

37. The cell of any one of paragraphs 33 to 36, wherein the disruption is due to a frameshift mutation which results in the generation of a non-sense mRNA and/or protein from the gene in which the frameshift mutation is present.

38. The cell of any one of paragraphs 33 to 37, wherein said cell does not comprise any integrated heterologous DNA that was used for said disruption.

39. A feline embryo, kitten, or adult cat comprising cells that are heterozygous or homozygous for a disruption of Fel d I locus sequences or flanking sequences thereof.

40. The feline embryo, kitten, or adult cat of paragraph 39, wherein the disruption is a knock-out.

41. The feline embryo, kitten, or adult cat of paragraph 39 or 40, wherein the disruption comprises deletion or mutation of:

(a) the promoter shared by Chain 1 and Chain 2 of the Fel d I locus;

(b) exon 1 of Chain 1 of the Fel d I locus;

(c) exon 2 of Chain 1 of the Fel d I locus;

(d) exon 3 of Chain 1 of the Fel d I locus;

(e) exon 1 of Chain 2 of the Fel d I locus;

(f) exon 2 of Chain 2 of the Fel d I locus;

(g) exon 3 of Chain 2 of the Fel d I locus; or (h) combinations or portions thereof.

42. The feline embryo, kitten, or adult cat of paragraph 41, wherein said combination comprises deletion or mutation of (a) and (b); (a), (b), and (c); (a), (b), (c), and (d); (a) and (e); (a), (e), and (f); (a), (e), (f), and (g); (a), (b), and (e); (a), (b), (c), and (e); (a), (b), (c), (d), and (e); (a), (b), (e), and (f); (a), (b), (c), (e), and (f); and (a), (b), (c), (d), (e), and (f); (a), (b), (e), (f), and (g); (a), (b), (c), (e), (f), and (g); (b) and (c); (b), (c), and (d); (c) and (d); (e) and (f); (e), (f), and (g); (f) and (g); or (a)-(g), or portions thereof.

43. The feline embryo, kitten, or adult cat of any one of paragraphs 39 to 42, wherein the disruption is due to a frameshift mutation which results in the generation of a non-sense mRNA and/or protein from the gene in which the frameshift mutation is present.

44. The feline embryo, kitten, or adult cat of any one of paragraphs 39 to 43, wherein said feline embryo, kitten, or adult cat does not comprise any integrated heterologous DNA that was used for said disruption.

45. The feline embryo, kitten, or adult cat of any one of paragraphs 39 to 44, wherein all of the cells of the feline embryo, kitten, or adult cat, including germ cells, comprises said disruption.

46. The method of any one of paragraphs 17 to 32, wherein the disruption is as defined in any one of paragraphs 33 to 45.

SEQUENCE LISTING

The application includes the sequence listing in computer readable form. This sequence listing is incorporated by reference herein.

All publications mentioned herein are incorporated herein by reference for the purpose of describing and disclosing the chemicals, cell lines, vectors, animals, instruments, statistical analysis and methodologies which are reported in the publications which might be used in connection with the invention.

ENDNOTES

[i] American College of Allergy, Asthma & Immunology, 2014. ACAAI.org

[ii] Luczynsak C M, JACI, August 1989.

[iii] Avner D B, Perzanowski, M, Platts-Mills T A E, Woodfolk J A. Evaluation of different techniques for washing cats; Quantitation of allergen removed from the cat and the effect on airborne Fel d 1. J Allergy Clin Immunology. Sept 1997: 307-312.

[iv] Clinical efficacy of specific immunotherapy to cat dander: a double-blind placebo-controlled trial. J Allergy Clin Immunology.

[v] Cat Allergies, WebMD, http://www.webmd.com/allergies/cat-allergies.

[vi] Huangfu D, Maehr R, Guo W, Eijkelenboom A, Snitow M, Chen A E, Melton D A. Induction of pluripotent stem cells by defined factors is greatly improved by small-molecule compounds. Nat Biotechnol. 2008 July; 26(7):795-7.doi: 10.1038/nbt1418

[vii] Shi Y, Desponts C, Do I T, Hahm H S, Schöler H R, Ding S. Induction of pluripotent stem cells from mouse embryonic fibroblasts by Oct4 and Klf4 with small-molecule compounds. Cell Stem Cell. 2008 Nov. 6; 3(5):568-74.doi: 10.1016/j.stem.2008.10.004.

[viii] Xian-Feng YU$_1$)*, Jae-Hwan KIM$_2$)*, Eun-Ji JUNG$_1$), Jin-Tae JEON$_1$) and Il-Keun KONG. Cloning and Characterization of Cat POU5F1 and NANOG for Identification of Embryonic Stem-like Cells. Journal of Reproductions and Development, Vol. 55, No. 4, 2009

[ix] Gómez MC1, Serrano M A, Pope C E, Jenkins J A, Biancardi M N, López M, Dumas C, Galiguis J, Dresser B L. Derivation of cat embryonic stem-like cells from in vitro-produced blastocysts on homologous and heterologous feeder cells. Theriogenology. 2010 Sep. 1; 74(4): 498-515. doi: 10.1016/j.theriogenology.2010.05.023.

[x] Takahashi, K. & Yamanaka, S. Induction of pluripotent stem cells from mouse embryonic and adult fibroblast cultures by defined factors. Cell 126, 663-676 (2006).

[xi] Maeder M L, et al. Rapid "open-source" engineering of customized zinc-finger nucleases for highly efficient gene modification. Mol Cell. 2008; 31(2):294-301.

[xii] Maeder M L, Thibodeau-Beganny S, Sander J D, Voytas D F, Joung J K. Oligomerized pool engineering (OPEN): an 'open-source' protocol for making customized zinc-finger arrays. Nat Protoc. 2009; 4(10):1471-1501.

[xiii] Sander J D, et al. Selection-free zinc-finger-nuclease engineering by context-dependent assembly (CoDA). Nat Methods. 2011; 8(1):67-69.

[xiv] Gupta A, Christensen R G, Rayla A L, Lakshmanan A, Stormo G D, Wolfe S A. An optimized two-finger archive for ZFN-mediated gene targeting. Nat Methods. 2012; 9(6):588-590.

[xv] Bhakta M S, et al. Highly active zinc-finger nucleases by extended modular assembly. Genome Res. 2013; 23(3): 530-538.

[xvi] Gaj T, Guo J, Kato Y, Sirk S J, Barbas C F. Targeted gene knockout by direct delivery of zinc-finger nuclease proteins. Nat Methods. 2012; 9(8):805-807.

[xvii] Kim H J, Lee H J, Kim H, Cho S W, Kim J S. Targeted genome editing in human cells with zinc finger nucleases constructed via modular assembly. Genome Res. 2009; 19(7):1279-1288

[xviii] Urnov F D, Rebar E J, Holmes M C, Zhang H S, Gregory P D. Genome editing with engineered zinc finger nucleases. Nat Rev Genet. 2010; 11(9):636-646.

[xix] Avner D B, Bocklandt S, Kehler J. Nucleic Acid Sequence and Homologous Recombination Vectors for Disruption of a Fel D I Gene, USPTO 2012/8,119,785 B2

[xx] Rouet P, Smih F, Jasin M. Expression of a site-specific endonuclease stimulates homologous recombination in mammalian cells. Proc Natl Acad Sci USA. 1994; 91(13):6064-6068.

[xxi] Radecke S, Radecke F, Cathomen T, Schwarz K. Zinc-finger nuclease-induced gene repair with oligodeoxynucleotides: wanted and unwanted target locus modifications. Mol Ther. 2010; 18(4):743-753.

[xxii] Soldner F, et al. Generation of isogenic pluripotent stem cells differing exclusively at two early onset Parkinson point mutations. Cell. 2011; 146(2):318-331.

[xxiii] Chen F, et al. High-frequency genome editing using ssDNA oligonucleotides with zinc-finger nucleases. Nat Methods. 2011; 8(9):753-755.

[xxiv] Soldner F, et al. Generation of isogenic pluripotent stem cells differing exclusively at two early onset Parkinson point mutations. Cell. 2011; 146(2):318-331.

[xxv] Urnov F D, et al. Highly efficient endogenous human gene correction using designed zinc-finger nucleases. Nature. 2005; 435(7042):646-651.

[xxvi] Doyon Y, et al. Enhancing zinc-finger-nuclease activity with improved obligate heterodimeric architectures. Nat Methods. 2011; 8(1):74-79.

[xxvii] Szczepek M, Brondani V, Buchel J, Serrano L, Segal D J, Cathomen T. Structure-based redesign of the dimeriza-

[xxvii] tion interface reduces the toxicity of zinc-finger nucleases. *Nat Biotechnol.* 2007; 25(7):786-793.

[xxviii] Miller J C, et al. An improved zinc-finger nuclease architecture for highly specific genome editing. *Nat Biotechnol.* 2007; 25(7):778-785.

[xxix] Gaj T, Guo J, Kato Y, Sirk S J, Barbas C F. Targeted gene knockout by direct delivery of zinc-finger nuclease proteins. *Nat Methods.* 2012; 9(8):805-807.

[xxx] Bogdanove A J, Voytas D F. TAL effectors: customizable proteins for DNA targeting. *Science.* 2011; 333(6051): 1843-1846.

[xxxi] Moscou M J, Bogdanove A J. A simple cipher governs DNA recognition by TAL effectors. *Science.* 2009; 326 (5959):1501.

[xxxii] Boch J, et al. Breaking the code of DNA binding specificity of TAL-type III effectors. *Science.* 2009; 326 (5959):1509-1512.

[xxxiii] Morbitzer R, Romer P, Boch J, Lahaye T. Regulation of selected genome loci using de novo-engineered transcription activator-like effector (TALE)-type transcription factors. *Proc Natl Acad Sci USA.* 2010; 107(50):21617-21622.

[xxxiv] Streubel J, Blucher C, Landgraf A, Boch J. TAL effector RVD specificities and efficiencies. *Nat Biotechnol.* 2012; 30(7):593-595.

[xxxv] Cong L, Zhou R, Kuo Y C, Cunniff M, Zhang F. Comprehensive interrogation of natural TALE DNA-binding modules and transcriptional repressor domains. *Nat Commun.* 2012; 3:968.

[xxxvi] Christian M, et al. Targeting DNA double-strand breaks with TAL effector nucleases. *Genetics.* 2010; 186(2):757-761.

[xxxvii] Miller J C, et al. A TALE nuclease architecture for efficient genome editing. *Nat Biotechnol.* 2011; 29(2): 143-148.

[xxxviii] Li T, et al. TAL nucleases (TALNs): hybrid proteins composed of TAL effectors and FokI DNA-cleavage domain. *Nucleic Acids Res.* 2011; 39(1):359-372.

[xxxix] Reyon D, Tsai S Q, Khayter C, Foden J A, Sander J D, Joung J K. FLASH assembly of TALENs for high-throughput genome editing. *Nat Biotechnol.* 2012; 30(5): 460-465.

[xl] Cong L, et al. Multiplex genome engineering using CRISPR/Cas systems. *Science.* 2013; 339 (6121):819-823.

[xli] Mali P, et al. RNA-guided human genome engineering via Cas9. *Science.* 2013; 339 (6121):823-826.

[xlii] Jinek M, Chylinski K, Fonfara I, Hauer M, Doudna J A, Charpentier E. A programmable dual-RNA-guided DNA endonuclease in adaptive bacterial immunity. *Science.* 2012; 337(6096):816-821.

[xliii] Cho S W, Kim S, Kim J M, Kim J S. Targeted genome engineering in human cells with the Cas9 RNA-guided endonuclease. *Nat Biotechnol.* 2013; 31(3):230-232.

[xliv] Fu Y, Sander J D, Reyon D, Cascio V M, Joung J K. Improving CRISPR-Cas nuclease specificity using truncated guide RNAs. *Nat Biotechnol.* 2014; 32 (3):279-284.

[xlv] Tsai S Q, et al. Dimeric CRISPR RNA-guided FokI nucleases for highly specific genome editing. *Nat Biotechnol.* 2014; 32(6):569-576.

[xlvi] Guilinger J P, Thompson D B, Liu D R. Fusion of catalytically inactive Cas9 to FokI nuclease improves the specificity of genome modification. *Nat Biotechnol.* 2014; 32 (6):577-582.

[xlvii] Verstegen, Journals of Reproduction and Fertility, 1993.

[xlviii] Swanson, W F, Going LO (laparoscopic oviductal) for ET and AI in Felids—Challenges, Strategies and Successes. *Reprod Domest Anim.* 2012 December; 47(Suppl 6): 136-140.

[xlix] William F. Swanson, Terri L. Roth, and David E. Wildt. In Vivo Embryogenesis, Embryo Migration, and Embryonic Mortality in the Domestic Cat. Biology of Reproduction 51, 452-464 (1994)

What is claimed is:

1. A method of producing a genetically modified cell, the method comprising the steps of:
 (a) providing a feline somatic cell, a feline embryonic stem cell, or a feline iPS cell; and
 (b) introducing into the cell of (a) two nucleases designed to disrupt a region of the *felis domesticus* 1 (Fel d I) locus, each nuclease comprising a programmable, sequence-specific, DNA binding module fused to a non-specific DNA cleavage domain; and
 (c) screening for a cell in which the region of the Fel d I locus is disrupted;
 wherein the nucleases are selected from Cas9, a transcription activator-like (TAL) effector nuclease, and Cpf1;
 wherein the region of the Fel d I locus comprises:
  the promoter shared by Chain 1 and Chain 2 of the Fel d I locus or a portion thereof;
  and at least one of a coding sequence of Chain 1 of the Fel d I locus and a coding sequence of Chain 2 of the Fel d I locus;
  wherein when the nuclease is Cas9, one of the two DNA binding modules are designed to target a first recognition site of Fel d I having a sequence selected from SEQ ID NOs: 43, 44, and 45; and the other of the two DNA binding modules are designed to target a second recognition site of Fel d I having a sequence selected from SEQ ID NOs: 46 and 47; and
  wherein when the nuclease is TAL, one of the two DNA binding modules is designed to target a recognition site of Fel d I having a sequence selected from SEQ ID NOs: 34, 35, and 36; and the other of the two DNA binding modules is designed to target a recognition site of Fel d I having a sequence selected from SEQ ID NOs: 37, 38, and 39.

2. The method of claim 1, wherein the provided cell is a feline somatic cell, and the feline somatic cell is reprogrammed into an iPS cell after step (b).

3. A cell produced by the method of claim 1, wherein the cell is heterozygous or homozygous for the disrupted region of the Fel d I locus; and wherein the cell is a feline somatic cell, an embryonic stem cell, or an iPS cell.

4. The cell of claim 3, wherein the cell is homozygous for disrupted region of the Fel d I locus.

5. The cell of claim 3, wherein the coding sequence of Chain 1 of the Fel d I locus comprises:
 (i) exon 1 of Chain 1 of the Fel d I locus, or a portion thereof;
 (ii) exon 2 of Chain 1 of the Fel d I locus, or a portion thereof; or
 (iii) both (i) and (ii); and
 wherein the coding sequence of Chain 2 of the Fel d I locus is selected from:
 (iv) exon 1 of Chain 2 of the Fel d I locus, or a portion thereof;
 (v) exon 2 of Chain 2 of the Fel d I locus, or a portion thereof; or
 (vi) both (iv) and (v).

6. The cell of claim 5, wherein the coding sequence of Chain 1 and the coding sequence of Chain 2 comprise: (i) and (iv); (i) and (vi); (iii) and (iv); or (iii), and (vi).

7. The cell of claim 3, wherein the disruption is due to a frameshift mutation which results in the generation of at least one of a non-sense mRNA and a protein from the gene in which the frameshift mutation is present.

8. The cell of claim 3, wherein the cell does not comprise any integrated heterologous DNA.

9. The method of claim 1;
 wherein step (b) further comprises introducing into the feline embryonic stem cell, the feline somatic cell, or the feline iPS cell, a vector or a DNA molecule comprising sequences that are homologous to sequences surrounding the sequences that the DNA cleavage domain is designed to disrupt; and wherein the method further comprises:
 (d) identifying a cell in which the region of the Fel d I locus has been disrupted by the nucleases; and
 (e) transferring the nucleus of the cell of step (d) into an enucleated embryo; and
 (f) culturing the embryo.

10. The method of claim 9, wherein the cell of step (a) is a feline somatic cell and the method further comprises reprogramming the feline somatic cell into an iPS cell after step (a).

11. The method of claim 9, wherein the cell of step (a) is an iPS cell that was reprogrammed from a feline somatic cell prior to step (a).

12. The method of claim 9, wherein the cell of step (a) is an embryonic stem cell, which is derived from an inner cell mass of a feline blastocyst.

13. The method of claim 1, further comprising:
 (d) expanding the cell of (c) into a cell line, wherein the cell line is heterozygous or homozygous for the disrupted region of the Fel d I locus.

14. The method of claim 1, wherein the coding sequence of Chain 1 of the Fel d I locus comprises:
 (i) exon 1 of Chain 1 of the Fel d I locus, or a portion thereof;
 (ii) exon 2 of Chain 1 of the Fel d I locus, or a portion thereof; or
 (iii) both (i) and (ii); and
 wherein the coding sequence of Chain 2 of the Fel d I locus comprises:
 (iv) exon 1 of Chain 2 of the Fel d I locus, or a portion thereof;
 (v) exon 2 of Chain 2 of the Fel d I locus, or a portion thereof; or
 (vi) both (iv) and (v).

15. The method of claim 14, wherein the coding sequence of Chain 1 and the coding sequence of Chain 2 comprise: (i) and (iv); (i) and (vi); (iii) and (iv); or (iii), and (vi).

16. The method of claim 1, wherein the DNA binding modules are designed to target a pair of recognition sites selected from:

(a) SEQ ID NO: 34 and SEQ ID NO: 37;
(b) SEQ ID NO: 35 and SEQ ID NO: 39;
(c) SEQ ID NO: 35 and SEQ ID NO: 38; and
(d) SEQ ID NO: 36 and SEQ ID NO: 39.

17. The method of claim 9, wherein the vector or DNA molecule further comprises a sequence encoding a selectable marker.

\* \* \* \* \*